(12) United States Patent
Costa et al.

(10) Patent No.: US 11,464,440 B2
(45) Date of Patent: Oct. 11, 2022

(54) SYSTEM FOR PROGNOSTICATING PATIENT OUTCOMES AND METHODS OF USING THE SAME

(71) Applicant: AUTEM MEDICAL, LLC, Hanover, NH (US)

(72) Inventors: Frederico Perego Costa, São Paulo (BR); Flavio Soares Correa Da Silva, São Paulo (BR); Antonio Francisco Iemma, São Paulo (BR)

(73) Assignee: AUTEM MEDICAL, LLC, Hanover, NH (US)

( * ) Notice: Subject to any disclaimer, the term of this patent is extended or adjusted under 35 U.S.C. 154(b) by 0 days.

(21) Appl. No.: 17/603,068

(22) PCT Filed: Apr. 10, 2020

(86) PCT No.: PCT/US2020/027757
§ 371 (c)(1),
(2) Date: Oct. 12, 2021

(87) PCT Pub. No.: WO2020/210693
PCT Pub. Date: Oct. 15, 2020

(65) Prior Publication Data
US 2022/0087591 A1 Mar. 24, 2022

Related U.S. Application Data

(60) Provisional application No. 62/831,837, filed on Apr. 10, 2019.

(51) Int. Cl.
*A61B 5/352* (2021.01)
*A61B 5/00* (2006.01)
*A61B 5/256* (2021.01)

(52) U.S. Cl.
CPC .............. *A61B 5/352* (2021.01); *A61B 5/256* (2021.01); *A61B 5/7275* (2013.01); *A61B 5/7285* (2013.01)

(58) Field of Classification Search
CPC ....... A61B 5/352; A61B 5/256; A61B 5/7275; A61B 5/7285
See application file for complete search history.

(56) References Cited

U.S. PATENT DOCUMENTS

| 5,441,528 | A | 8/1995 | Chang et al. |
| 5,501,704 | A | 3/1996 | Chang et al. |

(Continued)

FOREIGN PATENT DOCUMENTS

| EP | 0592851 A2 | 4/1994 |
| EP | 0592851 B1 | 4/1994 |

(Continued)

OTHER PUBLICATIONS

International Search Report and Written Opinion for PCT/US2020/027757 dated Jul. 17, 2020.

(Continued)

*Primary Examiner* — Lindsey G Wehrheim
(74) *Attorney, Agent, or Firm* — DLA Piper LLP (US)

(57) ABSTRACT

Systems and Methods for prognosticating an outcome in a patient by integrating a hemodynamic parameter (Hdp) monitoring system and a Radio Frequency generator synchronized by a processing system is disclosed. The system is capable of identifying health condition-specific Hdp variation values changes in a patient upon the exposure of low-energy amplitude modulated electromagnetic field frequencies. The construction of a library of frequencies can be used to more efficiently and effectively predict or treat an outcome in a patient by auto-tuning a treatment regimen specifically to the patient.

6 Claims, 50 Drawing Sheets

(56) References Cited

U.S. PATENT DOCUMENTS

| | | | |
|---|---|---|---|
| 5,634,939 | A | 6/1997 | Kuster et al. |
| 5,690,692 | A | 11/1997 | Fleming |
| 8,977,365 | B2 | 3/2015 | Pasche et al. |
| 2003/0139678 | A1 | 7/2003 | Hoium et al. |
| 2004/0127944 | A1 | 7/2004 | Casset |
| 2004/0230130 | A1 | 11/2004 | Kuo et al. |
| 2005/0143779 | A1 | 6/2005 | Libbus |
| 2006/0106323 | A1 | 5/2006 | Bischoff et al. |
| 2006/0106353 | A1 | 5/2006 | Bischoff et al. |
| 2007/0032733 | A1 | 2/2007 | Burton |
| 2007/0173908 | A1 | 7/2007 | Begnaud |
| 2008/0221419 | A1 | 9/2008 | Furman |
| 2010/0004517 | A1 | 1/2010 | Breyton |
| 2011/0130800 | A1 | 6/2011 | Weinstein et al. |
| 2011/0190598 | A1* | 8/2011 | Shusterman ........... G16H 50/20 705/2 |
| 2011/0224565 | A1 | 9/2011 | Ong et al. |
| 2012/0116149 | A1 | 5/2012 | Pilla et al. |
| 2013/0041235 | A1 | 2/2013 | Rogers et al. |
| 2013/0079853 | A1 | 3/2013 | Pasche et al. |
| 2013/0218021 | A1 | 8/2013 | Messano, Jr. et al. |
| 2014/0046674 | A1 | 2/2014 | Rosenfeld et al. |
| 2014/0303457 | A1 | 10/2014 | Pipke |
| 2015/0045686 | A1 | 2/2015 | Lynn |
| 2015/0126883 | A1 | 5/2015 | An et al. |
| 2016/0116366 | A1 | 4/2016 | Da Silva et al. |
| 2016/0317050 | A1 | 11/2016 | Costa |
| 2018/0296099 | A1* | 10/2018 | Costa ...................... A61N 1/40 |

FOREIGN PATENT DOCUMENTS

| | | | |
|---|---|---|---|
| EP | 2139557 | B1 | 6/2010 |
| WO | 2006031331 | A1 | 3/2006 |
| WO | 2008116640 | A2 | 10/2008 |
| WO | 2009138881 | A2 | 11/2009 |
| WO | 2011135297 | A1 | 11/2011 |
| WO | 2016176117 | A1 | 11/2011 |
| WO | 2018112413 | A1 | 6/2018 |

OTHER PUBLICATIONS

Anonymous: "Radionics—Wikipedia", Apr. 17, 2020.
Barbault et al., Amplitude-Modulated Electromagnetic Fields for the Treatment of Cancer: Discovery of Tumor-Specific Frequencies and Assessment of a Novel Therapeutic Approach (Apr. 14, 2009) J. Exp. Clin. Cancer Res. 28:51-60.
Costa et al., Treatment of Advanced Hepatocellular Carcinoma with Very Low Levels of Amplitude-Modulated Electromagnetic Fields (Aug. 9, 2011) Br. J. Cancer 105:640-648.
Costa, et al., Identification and characterization of specific hemodynamic patterns during exposure to radiofrequency electromagnetic fields amplitude-modulated at tumor-specific frequencies, BioEM2015 Jun. 14-19, Asiolmar Conference Center California USA, The Annual Meeting of Bioelectromagnetics Society, European Bioelectromagnetics Association Program, p. 39 (2015).
Extended European Search Report for EP No. 17880281.5 dated May 8, 2020.
Fortin et al., Non-Invasive Beat-to-Beat Cardiac Output Monitoring by an Improved Method of Transthoracic Bioimpedance Measurement (Nov. 2006) Computers in Biology and Medicine 36(11):1185-1203.
International Search Report and Written Opinion for PCT/US2016/028880 dated Aug. 24, 2016.
International Search Report and Written Opinion for PCT/US2017/066825 dated Feb. 15, 2018.
International Search Report and Written Opinion for PCT/US2018/055699 dated Feb. 8, 2019.
Janis Smith: "Questionable methods of cancer management: Electronic devices", A Cancer Journal for Clinicians, Jan. 1, 1994, pp. 115-127.
Jimenez et al., The anti-proliferative effects of RF EMF amplitude-modulated at tumor specific frequencies are mediated by calcium, BioEM2015 Jun. 14-19, Asiolmar Conference Center California USA, The Annual Meeting of Bioelectromagnetics Society, European Bioelectromagnetics Association Program, pp. 67-68 (2015).
Zimmerman et al., Cancer Cell Proliferation is Inhibited by Specific Modulation Frequencies (Dec. 1, 2012) Br. J. Cancer 106:307-313.
Zimmerman et al., Targeted treatment of cancer with radiofrequency electromagnetic fields amplitude-modulated at tumor-specific frequencies, Chin J. Cancer; 2013; vol. 32, Issue 11, pp. 573-581.
Masi et al. "Spontaneous Hemodynamic Oscillations during Human Sleep and Sleep Stage Transitions Characterized with Near-Infrared Spectroscopy" PLOS One, 2011;6(10):e25415. doi: 10.1371/journal.pone.0025415. Epub Oct. 17, 2011. PMID: 22043284; Pmcid PMC3197192. (Year: 2011).

* cited by examiner

Autem gEM™ Feasibility Prototype Trial

| Demographics | | |
|---|---|---|
| Male | 37 | 88.0% |
| Age (median) | 66.1 | |
| Group | | |
| Advanced HCC | 42 | 49.4% |
| Healthy controls | 43 | 50.6% |
| Histology | | |
| HCC | 39 | 92.9% |
| Hepatocholangio | 3 | 7.1% |
| Tumor characteristics | | |
| Pathology confirmation | 25 | 59.5% |
| Cirrhosis | 37 | 88.0% |
| Extra-hepatic metastasis | 12 | 28.5% |
| Child-Pugh B | 15 | 35.7% |
| Tumor progression | 22 | 52.3% |
| Previous treatment | | |
| Best support of care | 9 | 21.4% |
| RFA | 25 | 59.5% |
| Systemic | 31 | 73.8% |
| Combination with EMF | | |
| Chemotherapy | 6 | 14.2% |
| Sorafenib | 19 | 45.2% |
| Regorafenib | 1 | 2.3% |
| Levantinib | 1 | 2.3% |
| Nivolumab | 1 | 2.3% |
| Best support of care | 14 | 33.3% |

Procedure

- The current Autem gEM trial accrued 87 individuals:
  - advanced HCC
  - healthy controls
- Outpatient exposure procedure last 120 min with median interval between exposures of 39 days.
- EORTC C30 v3.0 questionnaire used for QoL assessment.
- EORTC QLQ-C30 is widely used in oncology clinical trials.[1]
- QoL assessment was collected just before every exposure procedure.
- A total of 194 exposure procedures were performed.
- From 5.820 planned data set, only 6 missing data points (0.1%).
- There was no reported treatment related limiting toxicity.

FIG. 1B

QoL assesment

Procedure

- EORTC C30 v3.0 questionnaire used for QoL assessment from 42 patients with advanced HCC.
- QoL assessment was analyzed for each exposure according to:

Score = Σ[Physical functioning + Role functioning + Emotional functioning + Cognitive functioning + Social functioning + global QOL]/6 - Σ[Fatigue + Nausea + Pain + Dyspnea + Insomnia + Appetite loss + Constipation + Diarrhea + Financial Difficulty]/9

- The median QoL score baseline was 66 for 42 advanced HCC patients.
- A total of 27 (64.2%) patients were submitted to re-exposure procedure.
  - 4 (9.5%) patients refused re-exposure
  - 3 (7.1%) patients were too early for re-exposure
  - 8 (19.0%) patients died before second exposure
- QoL score from first exposure to second exposure procedure showed:

| | | |
|---|---|---|
| Improvement | 18 patients | 66.7% |
| No changed | 0 | 0 |
| Decrease | 9 patients | 33.3% |

FIG. 1C

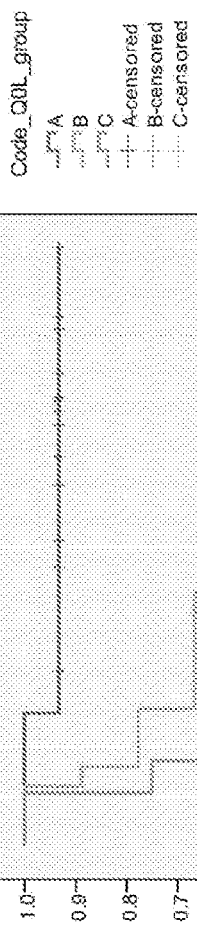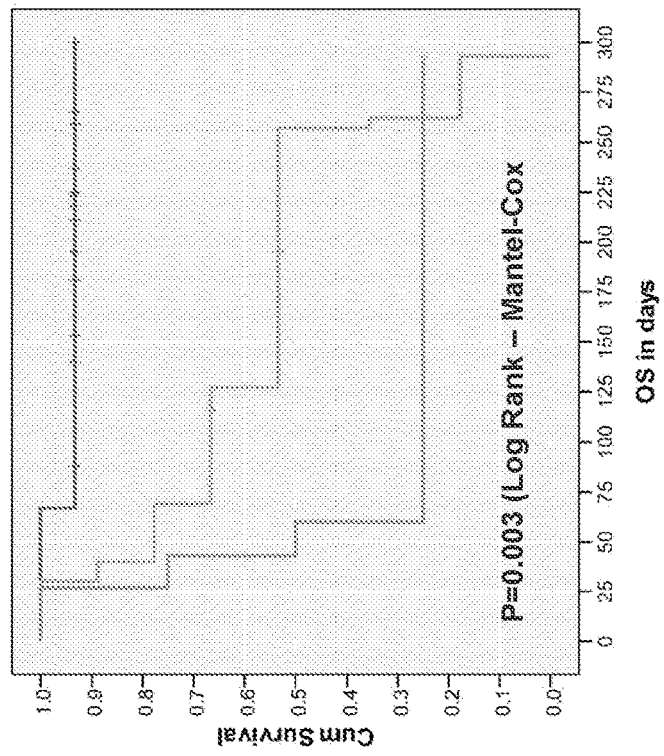
FIG. 4

| Time (sec) | Beat No. | Freq. (Hz) | RRI (ms) | dBP (mmHg) | SV (ml) | Geometric transformation | | | |
|---|---|---|---|---|---|---|---|---|---|
| | | | | | | 1 | 2 | 3 | 4 |
| 1072,43 | 1181 | 2522,328 | 885 | 65,3283 | 111,59 | 0,854 | 0,2095 | 0,516 | 2,43401277 |
| 1073,31 | 1182 | 2522,328 | 878,333 | 65,5562 | 110,888 | 0,646 | 0,41495 | 0,5145 | 2,2546169 |
| 1074,19 | 1183 | 2522,328 | 865,083 | 67,428 | 104,636 | 3,2915 | 0,82195 | 2,775 | 10,5919301 |
| 1075,06 | 1184 | 2522,328 | 913,417 | 67,688 | 102,466 | 30,792 | 0,8059 | 2,041 | 63,8564588 |
| 1075,97 | 1185 | 2522,328 | 891,042 | 67,8975 | 104,609 | 35,3545 | 0,02525 | 2,1565 | 72,9313652 |
| 1076,86 | 1186 | 2522,328 | 719,375 | 72,0519 | 104,404 | 74,646 | 1,97245 | 1,174 | 151,622681 |
| 1077,58 | 1187 | 2522,328 | 1060 | 58,9216 | 95,8814 | 256,146 | 8,64235 | 4,1588 | 522,062438 |
| 1078,64 | 1188 | 2522,328 | 889,667 | 65,3403 | 98,842 | 255,479 | 9,7745 | 5,7416 | 522,54551 |
| 1079,53 | 1189 | 2522,328 | 894,042 | 66,0173 | 104,737 | 87,354 | 2,87085 | 1,4672 | 177,991526 |
| 1080,42 | 1190 | 2522,328 | 864,708 | 65,3261 | 107,884 | 16,8545 | 0,6841 | 1,374 | 35,3136739 |
| 1081,29 | 1191 | 2522,328 | 837,75 | 69,408 | 110,254 | 1,188 | 2,38655 | 0,3885 | 6,33376431 |
| 1082,13 | 1192 | 2743,995 | 902,333 | 69,9201 | 112,295 | 45,7705 | 1,7849 | 0,1645 | 93,3685493 |
| 1083,03 | 1193 | 2743,995 | 888,417 | 71,2033 | 111,404 | 39,2495 | 0,38555 | 1,466 | 80,0441134 |
| 1083,92 | 1194 | 2743,995 | 889,042 | 70,4496 | 111,67 | 7,2705 | 1,01845 | 0,5785 | 15,8062468 |

FIG. 5

| | Mean[a] | | | | Median | | | |
|---|---|---|---|---|---|---|---|---|
| | | | 95% Confidence Interval | | | | 95% Confidence Interval | |
| Estimate | Std. Error | Lower Bound | Upper Bound | Estimate | Std. Error | Lower Bound | Upper Bound |
| 318.402 | 21.988 | 275.305 | 361.500 | . | . | . | . |

| Mean[a] | | | | Median | | | |
|---|---|---|---|---|---|---|---|
| | | 95% Confidence Interval | | | | 95% Confidence Interval | |
| Estimate | Std. Error | Lower Bound | Upper Bound | Estimate | Std. Error | Lower Bound | Upper Bound |
| 350.500 | 13.071 | 324.880 | 376.120 | . | . | . | . |

| Mean[a] | | | | Median | | | |
|---|---|---|---|---|---|---|---|
| | | 95% Confidence Interval | | | | 95% Confidence Interval | |
| Estimate | Std. Error | Lower Bound | Upper Bound | Estimate | Std. Error | Lower Bound | Upper Bound |
| 258.222 | 47.830 | 164.475 | 351.969 | 293.000 | 53.666 | 187.815 | 398.185 |

| | Chi-Square | df | Sig. |
|---|---|---|---|
| Log Rank (Mantel-Cox) | 11.148 | 1 | 0.0008 |

FIG. 7B

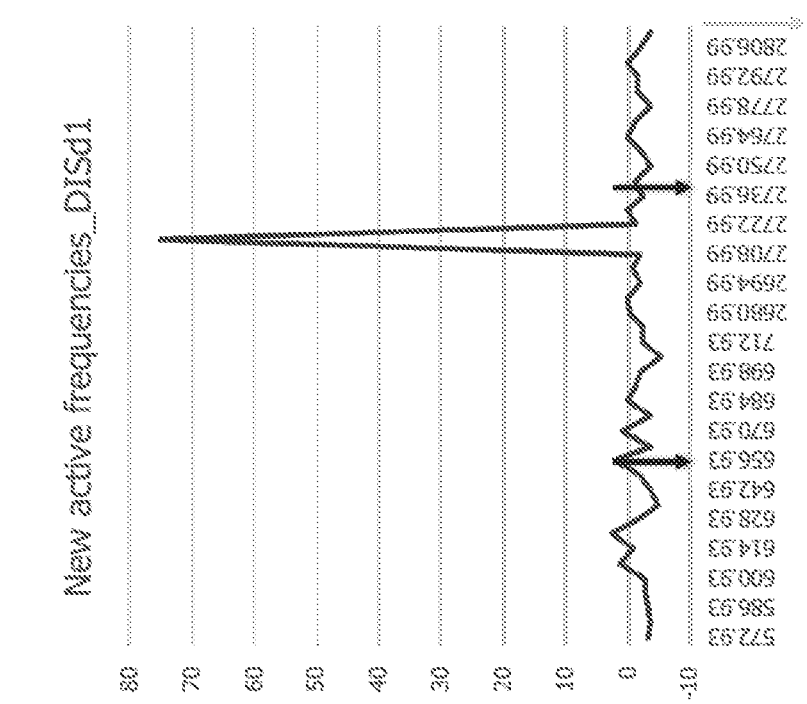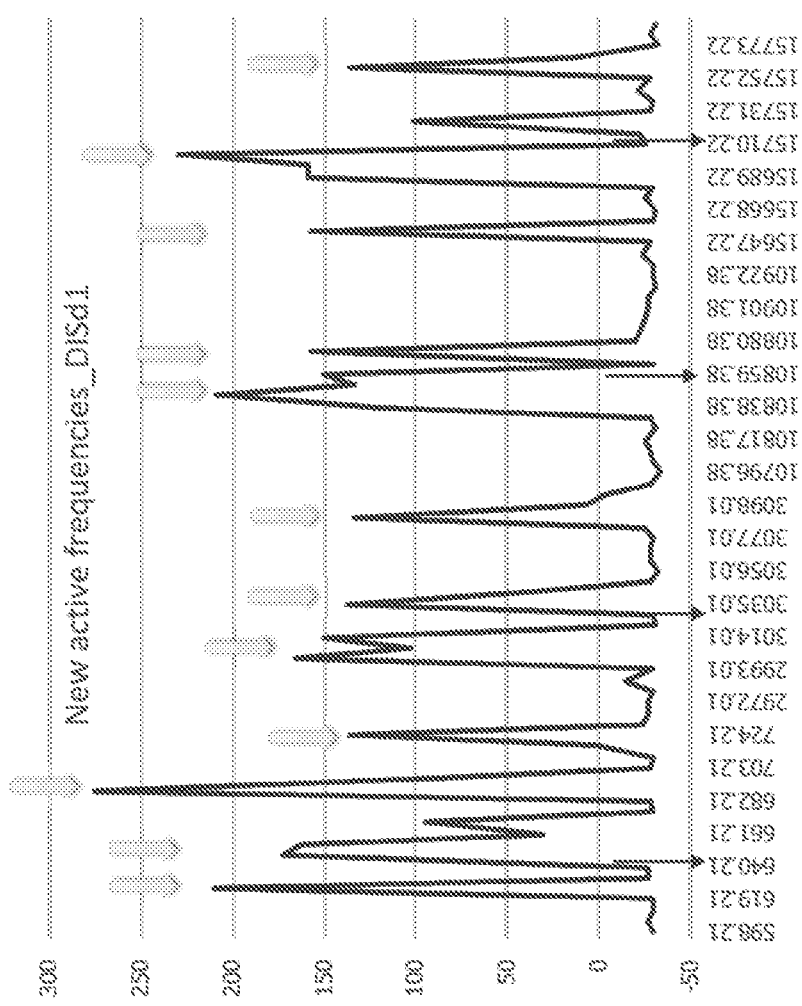
FIG. 27B

| Delineadas | | Padronizadas | |
|---|---|---|---|
| Freq_Hz | DISD1 | Z(Freq) | Z(DISD1) |
| 572.93 | -3.16 | -1.61 | -0.54 |
| 579.93 | -3.84 | -1.45 | -0.85 |
| 586.93 | -3.23 | -1.29 | -0.57 |
| 593.93 | -2.88 | -1.13 | -0.41 |
| 600.93 | -3.01 | -0.97 | -0.47 |
| 607.93 | 1.21 | -0.81 | 1.44 |
| 614.93 | -1.00 | -0.64 | 0.44 |
| 621.93 | 2.66 | -0.48 | 2.09 |
| 628.93 | -2.08 | -0.32 | -0.05 |
| 635.93 | -4.84 | -0.16 | -1.30 |
| 642.93 | -3.75 | 0.00 | -0.80 |
| 649.93 | -2.11 | 0.16 | -0.06 |
| 656.93 | 2.01 | 0.32 | 1.80 |
| 663.93 | -3.83 | 0.48 | -0.84 |
| 670.93 | 0.73 | 0.64 | 1.22 |
| 677.93 | -3.67 | 0.81 | -0.77 |
| 684.93 | 0.02 | 0.97 | 0.90 |
| 691.93 | -1.06 | 1.13 | 0.41 |
| 698.93 | -1.91 | 1.29 | 0.03 |
| 705.93 | -5.30 | 1.45 | -1.51 |
| 712.93 | -2.33 | 1.61 | -0.16 |
| Mean | -1.97 | 0.00 | 0.00 |
| Std. Dev. | 2.21 | 1.00 | 1.00 |

FIG. 28

SYSTEM FOR PROGNOSTICATING PATIENT OUTCOMES AND METHODS OF USING THE SAME

PRIORITY

This patent application claims priority to International Application No. PCT/US2020/027757, titled "SYSTEM FOR PROGNOSTICATING PATIENT OUTCOMES AND METHODS OF USING THE SAME," filed on Apr. 10, 2020, which claims priority to U.S. Provisional Patent Application No. 62/831,837, titled "SYSTEM FOR PROGNOSTICATING PATIENT OUTCOMES AND METHODS OF USING THE SAME," filed on Apr. 10, 2019, the contents of which are hereby incorporated by reference herein in their entireties.

BACKGROUND

Prediction is central to medicine as preventive and therapeutic interventions are prescribed or recommended on implicit or explicit expectations about future health outcomes. Prediction aims to quantify the probability of these future health outcomes based on a set of predictor variables.

Cancer development follows a pathway dependent on characteristics of a microenvironment and specific genetic mutations of an individual. The direct products of mutant genes and the resulting microenvironmental changes induced by the cancer proliferation provoke significant alterations in the body homeostasis. The development of non-invasive and objective techniques designed to detect and measure homeostatic alterations induced by cancerous cells may provide prognostic and predictive information to guide more effective treatment strategies for cancers in patients.

Homeostasis is the ability or tendency of a living organism, cell, or group to keep internal conditions the same despite changes to external conditions or this state of internal balance. Allostasis is the process of achieving stability, or homeostasis, through physiological or behavioral change. Homeostatic regulation reflects the stability of constants, while allostatic regulation means stability through change. Homeostatic systems must be maintained within a narrow range. This means that deviations in a homeostatic system trigger a restorative response to correct the changes. In contrast, the regulation of allostatic systems can operate in a relatively broad range of regulation.

Stress is a physical and/or emotional stimulus that may alter the homeostatic control of an organism. Stress can be thought of as an input, processing, and outcome reaction. Stimuli may affect the homeostasis of a system. The organism may process the stimuli and determine whether the stimuli are stressors or not, which may result in a stress response. This process can be cyclical because allostasis involves the regulation of internal conditions through dynamic alterations in hormonal and physical parameters that may increase or decrease vital functions to a new steady state. Allostatic load may be considered the cost of chronic exposure to elevated or fluctuating allostatic responses resulting from chronic or repeated stimuli. Cancer cell proliferation and its central role of oxygen supply, for example, may be a source of mechanical and metabolic stress to the body.

Allostatic load has been studied as a multisystem approach to the assessment of physical health status. Allostatic load may be described as the activation of the neuroendocrine stress responses mediated by the autonomic nervous system (ANS) and the endocrine system that may lead to a physiological response. Analysis of the fluctuation of heart rate variability (HRV) over a period of time can be used as a measure of ANS status and flexibility. The heart is under tonic inhibitory control by parasympathetic influences. Thus, resting cardiac autonomic balance favors energy conservation by way of parasympathetic dominance over sympathetic influences. In addition, heart rate over time can be characterized by beat-to-beat variability, which also implicates vagal dominance, as the sympathetic influence on the heart is too slow to produce rapid beat-to-beat changes. As a result, low HRV may be associated with increased risk of all-cause mortality, and low HRV can be a marker for disease.

Allostatic load scores and HRV may be used as an indicator of stress-related health risk. Analysis of allostatic load and HRV suggest that allostatic load may increase and HRV may decrease with stress and stress-related diseases. This negative correlation between allostatic load and HRV can be mediated by vagal tone and may suggest a correlation with health risk assessments.

Hemodynamic parameter (Hdp) monitors, or any other device capable of registering hemodynamic or cardiac electrical activities, are used to sense and monitor various Hdp values. Various Hdp values can be used to diagnose cardiovascular conditions of a patient. Hdp measurements, generally performed in conjunction with an electrocardiogram (ECG), can include measurements of stroke volume (SV), stroke index (SI) and cardiac output (CO). Such measurements are indicated for the diagnosis and therapy of patients suffering from cardiac conditions, such as heart failure, hypertension, coronary artery disease, and pericardial disease, as well as obstructive lung and pleural disease and renal insufficiency.

HRV is the physiological phenomenon of variation in the time interval between heartbeats. It is measured by the variation in the beat-to-beat interval. Other terms have also been used to described oscillation in consecutive cardiac cycles, such as heart, period variability, R-wave R-wave variability, and R-wave R-wave interval (RR interval or RRI) tachogram. Sample processes for identifying HRV variables include recording RRI values, computer digitizing, artifact identification, HRV data editing, HRV interval rejection, HRV data sequencing and interpolation, and sampling for time domain HRV and frequency domain HRV.

SUMMARY

In an embodiment, a system for diagnosing or prognosticating a health condition of a patient, or the quality of life, survival, or hospital admission of a patient, may include an Hdp monitoring system configured to detect, measure and store a plurality of first values for RRI values exhibited by the patient during a basal or non-exposure period and a plurality of second values for RRI values exhibited by the patient prior to, during, or after an exposure period in which the patient is exposed to low-energy electromagnetic carrier output signals. The system may further include an electrically powered generator adapted to be actuated to generate the low-energy electromagnetic carrier output signals for exposing or applying the low-energy electromagnetic carrier output signals to the patient during the exposure period, and a processing system that may be configured to synchronize the Hdp monitoring system and the electrically powered generator. In some embodiments, the processing system can be internal or external to the Hdp monitoring system. In some embodiments, the processing system can be configured to sense and identify one or more of an amplitude-modulated electromagnetic frequency. The system may further comprise an interface controller that can be in operable communication with the Hdp monitoring system and the electrically powered generator. In some embodiments, the Hdp monitoring system may measure one or more RRI values, calculate one or more HRV values, record one or more HRV variation values, identify one or more amplitude-modulated electromagnetic frequencies, or a combination thereof. In some embodiments, the processing system may integrate the one or more HRV values with a library and the electrically powered generator. In some embodiments, the low-energy electromagnetic carrier output signals of the system may comprise an amplitude modulation frequency in a range from about 0.01 Hz to about 150 kHz.

In some embodiments, a Hdp monitoring system may be configured to detect, measure and store a plurality of first values for RRI values exhibited by one or more surrogate patients during a basal or non-exposure period and a plurality of second values for RRI values exhibited by the one or more surrogate patients during or after an exposure period in which the one or more surrogate patients are exposed to low-energy electromagnetic output signals. In some embodiments, the system may interface with an electrically powered generator adapted to be actuated to generate the low-energy electromagnetic carrier output signals for exposing or applying the low-energy electromagnetic carrier output signals to the surrogate patients during the exposure period. The system may further comprise a processing system configured to synchronize the Hdp monitoring system and the electrically powered generator. The processing system can be internal or external to the Hdp monitoring system. In some embodiments, the processing system can be configured to sense and identify one or more amplitude-modulated electromagnetic frequencies. In further embodiments, the system may comprise an interface controller in operable communication with the Hdp monitoring system and the electrically powered generator. In some embodiments, the Hdp monitoring system can be configured to measure one or more RRI values, calculate one or more HRV values, record one or more HRV variation values, identify one or more amplitude-modulated electromagnetic frequencies, or a combination thereof. The processing system may integrate the one or more HRV values with a library and the electrically powered generator. In some embodiments, the low-energy electromagnetic carrier output signals may comprise an amplitude modulation frequency in a range from about 0.01 Hz to about 150 kHz.

In some embodiments, a system for diagnosing or prognosticating a health condition of a patient, or the quality of life, survival, or hospital admission of a patient, may comprise a Hdp monitoring system that may be configured to detect, measure, and record a plurality of first values for each of a plurality of hemodynamic parameters exhibited by a patient during an exposure period. The exposure period may comprise a time period in which the patient is exposed to one or more electromagnetic frequency signals. The system may further comprise an electrically powered frequency generator adapted to generate the one or more electromagnetic frequency signals during the exposure period. The one or more electromagnetic frequency signals can be configured to influence a cellular function. The system may further include a processing system that can be configured to synchronize the Hdp monitoring system and the frequency generator, auto-tune a carrier signal to adjust forward energy delivered to the patient, and instruct the frequency generator to expose the patient to each of the one or more electromagnetic frequency signals by modulating an amplitude of the carrier signal to produce an amplitude-modulated electromagnetic frequency. In some embodiments, the amplitude-modulated electromagnetic frequency can be selected from within a range of 10 Hz to 1,000 Hz. In further embodiments, the plurality of hemodynamic parameters may comprise one or more of RR interval, heart rate, systolic blood pressure, diastolic blood pressure, median blood pressure, pulse pressure, stroke volume, cardiac output, and total peripheral resistance. In some embodiments, the processing system may be configured to actuate the frequency generator to generate one or more radio frequency (RF) carrier signals having highly specific frequencies based on at least the plurality of first values for each of the plurality of hemodynamic parameters. In some embodiments, the frequency generator may comprise a programmable generator. In further embodiments, the programmable generator may comprise one or more controllable generator circuits, wherein each controllable generator circuit can be configured to generate one or more RF carrier signals. In some embodiments, each controllable generator circuit may comprise an amplitude modulation (AM) frequency control signal generator that can be configured to control amplitude-modulated variations of the one or more RF carrier signals. In further embodiments, the RF carrier signal can be a 27.12 MHz signal. In some embodiments, the system may further comprise a computing device operably connected to the processing system and configured to store at least one computational statistics algorithm configured to output one or more variables for use in auto-tuning the carrier signal.

In some embodiments, a system for prognising the quality of life, survival, or hospital admission of a patient may comprise a Hdp monitoring system that can be configured to detect, measure, and record a plurality of first values for each of a plurality of hemodynamic parameters exhibited by a patient during an exposure period. The exposure period may comprise a time period in which the patient is exposed to a plurality of electromagnetic frequency signals. In some embodiments, the system may further include an electrically powered frequency generator adapted to generate the one or more electromagnetic signals during the exposure period. In some embodiments, the system may further include a processing system configured to synchronize the Hdp monitoring system and the frequency generator, auto-tune a carrier signal to adjust forward energy delivered to the patient, and instruct the frequency generator to expose the patient to each of the plurality of electromagnetic frequency signals by modulating an amplitude of the carrier signal to produce a desired electromagnetic frequency signal. In some embodiments, the amplitude-modulated electromagnetic frequency can be selected from within a range of 10 Hz to 1,000 Hz.

In some embodiments, a method for diagnosing or prognosticating a health condition of a patient may include measuring, by a Hdp monitoring system, a plurality of first values for RRI values, calculating HRV values exhibited by a patient during exposure of the patient to a RF carrier signal, processing HRV values and exposure of the patient to one or more RF carrier signal having highly specific frequencies, recording representative HRV variation values exhibited by one or more surrogate patients during exposure of the one or more surrogate patients to the one or more RF carrier signals, storing the plurality of first values and a plurality of second values of representative HRV variation values, and transferring the representative HRV variation values from a pre-diagnosis or diagnosed patient to a library for further processing. In some embodiments, the one or more RF carrier signals may comprise an amplitude modulation electromagnetic frequency in a range from about 0.01 Hz to about 150 kHz.

In some embodiments, a method of diagnosing or prognosticating a health condition of a patient may include determining, by a processing system, a plurality of electromagnetic frequency signals to apply to the patient, auto-tuning, by the processing system, a carrier wave to balance forward energy delivered to the patient, exposing, by a frequency generator operably connected to the processing system, the patient to each of the plurality of electromagnetic frequency signals by modulating an amplitude of the carrier signal to produce a desired electromagnetic frequency signal that can be configured to influence a cellular function of the patient, measuring, by a hemodynamic parameter (Hdp) monitoring system, a plurality of first values for a plurality of hemodynamic parameters exhibited by a patient during exposure of the patient to the plurality of electromagnetic frequency signals, and analyzing the plurality of first values to provide for a diagnosis of a health condition of the patient. In some embodiments, the amplitude modulated signal can be selected from within a range of 10 Hz to 1,000 Hz. In some embodiments, the method may further comprise identifying a frequency response to a single frequency exposure of an amplitude-modulated electromagnetic frequency as non-reactive, reactive, or post-reactive. In further embodiments, the plurality of hemodynamic parameters may comprise one or more of RR interval, heart rate, systolic blood pressure, diastolic blood pressure, median blood pressure, pulse pressure, stroke volume, cardiac output, and total peripheral resistance. In some embodiments, the method may comprise determining a RF carrier signal that causes Hdp value changes in the patient. In further embodiments, the carrier signal may comprise a 27.12 MHz signal. In some embodiments, auto-tuning may comprise adjusting the forward energy of the carrier signal based upon an output of a computational statistics algorithm.

In some embodiments, a method of prognosticating the quality of life, survival, or hospital admission of a patient may include determining, by a processing system, a plurality of amplitude-modulated electromagnetic frequencies to apply to the patient, auto-tuning, by the processing system, a carrier wave to balance forward energy delivered to the patient, exposing, by a frequency generator operably connected to the processing system, the patient to each of the plurality of amplitude-modulated electromagnetic frequencies by modulating an amplitude of the carrier signal to produce a desired amplitude-modulated electromagnetic frequency that can be configured to influence a cellular function of the patient, measuring, by a Hdp monitoring system, a plurality of first values for a plurality of hemodynamic parameters exhibited by a patient during exposure of the patient to the plurality of amplitude-modulated electromagnetic frequencies, and analyzing the plurality of first values to provide for a diagnosis or a prognosis of the quality of life, survival, or hospital admission of the patient. In some embodiments, the amplitude-modulated electromagnetic frequency can be selected from within a range of 10 Hz to 1,000 Hz. In some embodiments, the method may further comprise identifying a specific frequency response to a single frequency exposure of an amplitude-modulated electromagnetic frequency as non-reactive, reactive, or post-reactive. In further embodiments, the plurality of hemodynamic parameters may comprise one or more of RR interval, heart rate, systolic blood pressure, diastolic blood pressure, median blood pressure, pulse pressure, stroke volume, cardiac output, and total peripheral resistance. In some embodiments, the method may comprise determining an amplitude-modulated electromagnetic frequency that causes significant Hdp value changes in the patient. In some embodiments, auto-tuning may comprise adjusting the forward energy of the carrier signal based upon an output of a computational statistics algorithm. In further embodiments, the cellular function can be microtubule conductivity.

In some embodiments, a programmable generator can be activatable by electrical power and structured to influence cellular functions or malfunctions in a warm-blooded mammalian subject. In some embodiments, the programmable generator may comprise at least one controllable low-energy electromagnetic energy generator circuit for generating one or more high frequency carrier signals. The at least one generator circuit may include at least one amplitude modulation control signal generator for controlling amplitude-modulated variations of the one or more carrier signals, and at least one programmable amplitude modulation frequency control signal generator for controlling frequencies at which amplitude modulations are generated. In some embodiments, each programmable amplitude modulation frequency control signal generator can be adapted to accurately control the frequencies at which the amplitude modulations are generated to within an accuracy of at least 1000 parts per million relative to a reference amplitude modulation frequency selected from within a range of 0.01 Hz to 150 kHz. In some embodiments, the programmable generator may further include at least one data processor constructed and arranged for communication with the at least one generator circuit and for receiving control information from a source of control information, and a connection position configured to connect to an electrically conductive applicator that may be configured to apply one or more amplitude-modulated low-energy emissions at a program-controlled frequency to the warm-blooded mammalian subject. The reference amplitude modulation frequencies can be selected dependent on a health condition of the warm-blooded mammalian subject.

BRIEF DESCRIPTION OF THE DRAWINGS

FIGS. 1A-C illustrate a quality of life analysis in accordance with an embodiment.

FIG. 4 illustrates survival curves according to prognostication groups in accordance with an embodiment.

FIG. 5 illustrates a digitally synchronized hemodynamic time series merged with data in accordance with an embodiment. The data were processed by a mathematical algorithm to identify a specific hemodynamic stress response to amplitude modulated electromagnetic frequencies shown in the box [columns left to right: time (s), beat number, frequency (Hz), RR (ms), dBP (mmHg), SV (ml), and geometric transformations 1 to 4].

FIGS. 7A-E illustrate survival curves for one or more patient populations in accordance with some embodiments. The overall survival curve for the patient population had a median overall survival (mOS) not reached at +9.0 months (95% CI 7.4-10.3). The low-risk group population (blue curve) had mOS not reached and high-risk group population (red curve) had mOS=7.1 months (95% CI 4.8-9.4) (FIG. 99B).

FIG. 27B illustrates the determination of new active frequencies in comparison with a first frequency exposure protocol in accordance with an embodiment.

FIG. 28 illustrates the distribution of active frequencies in accordance with an embodiment.

DETAILED DESCRIPTION

Figure 1A:
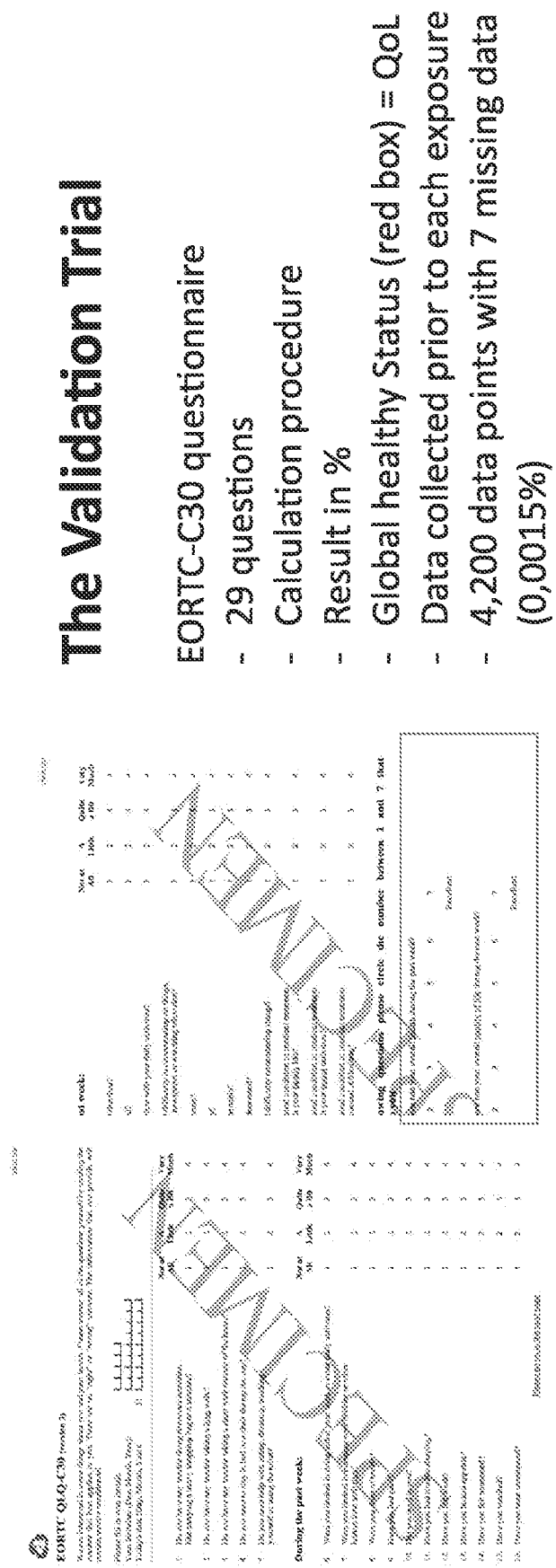

This disclosure relates to a Hdp monitoring system for characterization, diagnosing or prognosticating the quality of life, survival, or hospital admission of a patient or a warm-blooded mammalian subject. This disclosure more particularly involves an integrated Hdp system capable of measuring, monitoring and recording electrical activity of the heart by RR interval (RRI) values and computing those values in order to identify specific heart rate variability (HRV) values resulting from exposure of the warm-blooded mammalian subject to amplitude modulated electromagnetic frequencies (AM EMF) thereof in order to diagnose or provide a prognosis of the quality of life, survival, or hospital admission of a patient.

In some embodiments, the health condition may include, without limitation, hepatocellular carcinoma, colorectal cancer, breast cancer, ovarian cancer, pancreatic cancer, head and neck cancer, bladder cancer, liver cancer, renal cancer, melanoma, gastrointestinal cancer, prostate cancer, small cell lung cancer, non-small cell lung cancer, sarcoma, glioblastoma, T- and B-cell lymphoma, endometrial cancer, or cervical cancer.

A frequency synthesizer can be used to generate a specific frequency or a series of such frequencies. A user can use a keyboard or other input device to select such frequencies, which in turn can cause a circuit to turn the generated signal ON or OFF within well-defined time intervals.

In an embodiment, a processing system can calculate hemodynamic parameters from measured and recorded RRI values using an ECG monitoring system connected to a patient or a warm-blooded mammalian subject when exposing the subject to one or more radio frequency carrier signals emitted by a programmable generator. The Hdp monitoring system measures and records RRI values for further processing. A processing system that is either internal or external to the portable medical device can execute a series of computing processes intended to calculate HRV values. HRV values are organized, synchronized, aggregated, recorded and stored as representative HRV variation values for further computational statistics procedures to be performed in a library of frequencies (ILf). The processing system provides the sensing capability of the Hdp monitoring system by using various measured and recorded HRV values of the patient and identifies amplitude modulated electromagnetic frequencies (AM EMF), characterized by recognizable patterns of HRV value changes. The AM EMF is a subset of signals that influence cellular functions or malfunctions in a warm-blooded mammalian subject (i.e., the patient). The Hdp monitoring system exposes the patient to radio frequency carrier signals using a probe (more broadly described as an electrically conductive applicator) for applying the emissions to the patient via a topical contact at one or more determined parts of the body. The Hdp monitoring system measures and records RRI values from the patient using electrodes placed in topical contact with one or more determined parts of the body.

In an embodiment, the Hdp monitoring system can calculate and identify representative HRV variation values that can be stored in an internal temporary storage device for asynchronous transmission to the ILf. In an alternate embodiment, the Hdp monitoring system can simultaneously transmit the representative HRV variation values to the ILf by a wireless connection to an encrypted network. In an alternate embodiment, the portable medical device can transmit the RRI values and the information related to the patient's exposure to highly specific frequency radio frequency carrier signals to an external device with a processing system in order to calculate and identify the representative HRV variation values before transmission to the ILf.

In an embodiment, the Hdp monitoring system or an external device with a processing system can be connected to an encrypted network. The representative HRV variation values can be transmitted to the ILf via a synchronous or asynchronous connection to an encrypted web platform for further computational statistics computing procedures.

In an embodiment, the processing system can include a device synchronizer, a data aggregator, a storage device and/or a storage interface, and an interface controller. The interface controller can be configured to match the calculated HRV values and the exposure to one or more amplitude modulated electromagnetic frequencies (synchronization). Additionally or alternatively, the interface controller can be configured to consolidate the records (data aggregation) to be stored (storage) for further processing and transmission such that HRV values are linked to an exposure to one or more highly specific frequency radio frequency carrier signals from which such HRV values were measured. The Hdp monitoring system and the programmable generator can be connected via the interface controller. The modules corresponding to synchronization and data aggregation and the storage interface can be arranged in a portable medical device integrated hardware solution or in an external device with computing capabilities as an integrated hardware solution.

In another embodiment, the Hdp monitoring system can diagnose or prognose a health condition, quality of life, survival, or hospital admission of a patient by exposing the patient to one or more radio frequency carrier signals. The programmable generators can be loaded with instructions configured to produce a health condition-specific group of AM EMF for warm-blooded mammalian subjects with a specific health condition. In an embodiment, the group of AM EMF can be accurately controlled. In an embodiment, each AM EMF can have a resolution of about 0.5 Hz from the intended modulation frequency. In another embodiment, each AM EMF can have a resolution of about 0.1 Hz from the intended modulation frequency. In yet another embodiment, the group of AM EMF can have a resolution of about 0.01 Hz from the intended modulation frequency. In still another embodiment, each AM EMF can have a resolution of about 0.001 Hz from the intended modulation frequency.

In an embodiment, the patient may be exposed to AM EMF emissions at a relatively low and safe energy level that results in low levels of absorption by the patient. It is believed that physiological exchanges or the flow of electrical impulses within warm-blooded animals (which are to be affected by application of the emissions of the disclosed system) are similar at low-energy levels. Regardless, in certain implementations, in the region of exposure (at or near to the point of contact or by induction of an electrically conductive applicator with a subject receiving treatment), the specific absorption rate (SAR) should be and is most preferably substantially less than 1.6 mW/g of living tissue.

Furthermore, emissions can be stably maintained during emission, such that the stability should preferably be of the order of $10^{-5}$, more preferably $10^{-6}$, and most preferably $10^{-7}$. The stability of the emissions can be determined as the relative deviation of the frequency divided by the desired frequency, e.g., 0.01 Hz (deviation)/1,000 Hz (desired freq.)= $10^{-5}$.

In certain implementations, the programmable generator can include a microprocessor (or other similar integrated circuit) configured to operate according to control information that is, for example, loaded from the processing system. In some examples, the programmable generator can combine other monitoring systems, such as an ECG monitoring system, a portable medical device, or other computing servers, all of them operating together and synchronized by the processing system as one single new system. As a result, the new and improved programmable generator can be loaded with an updated series of amplitude modulated electromagnetic frequencies identified in a single warm-blooded mammalian subject or from a group of warm-blooded mammalian subjects with the same health condition. In addition, the new and improved programmable generator as described herein can support different applications such as diagnosis, prognosis, searching for amplitude modulated electromagnetic frequencies, and treatment follow-up. The microprocessor (or integrated circuit) can control the function of the programmable generator to produce the desired therapeutic emissions. In some examples, the programmable generator can include an impedance transformer connected to an emitter of low-energy electromagnetic emissions and a probe (e.g., an electrically conductive applicator) that applies the emissions to a patient. The impedance transformer can be configured to substantially match the impedance of the patient sensed by the emitter circuit with the impedance of the output of the emitter circuit.

The Hdp monitoring system can be configured to measure RRI values, calculate HRV values, and record representative HRV variation values used for AM EMF identification. The identified AM EMF can be used for diagnosis or prognosis of a health condition of a patient. As illustrated in FIGS. 1-9, the identified AM EMF can be used for prognosticating the quality of life, survival, or hospital admission of a patient. The system as described herein can thus include a Hdp monitoring system that measures RRI values and records various identified representative HRV variation values of the patient. Accordingly, the system can generally measure various identified RRI values of the patient using electrodes placed in topical contact with various determined parts of the body. An ECG monitoring system can further include a subsystem configured to record the various identified RRI values of the patient. The calculated and recorded HRV values can be stored in one or more storage devices.

The HRV values can be calculated and recorded following established procedures. Initial measurements of RRI values during non-exposure radio frequency carrier signal periods in an individual or patient or RRI values thereof are herein identified as basal measurements or basal RRI values. Initial measurements of the above parameters may be performed on a warm-blooded mammalian subject after a period of relaxation, such as about 15 minutes, while the patient is lying in a supine position (face and preferably also palms of the hands facing upwardly) or in another comfortable and relaxed position.

After obtaining the above initial measurements, a selected series of one or more radio frequency carrier output signals can be applied to the subject, thereby providing for exposure measurements or exposure RRI values.

The above-mentioned one or more radio frequency carrier signals can be amplitude modulated according to a control program loaded into the programmable generator, which generates an AM EMF output signal at certain predetermined amplitude modulation frequencies. In some implementations, patients are preferably exposed to AM EMF output signals, or such signals are applied to patients, during a determined period of time, most preferably over a period of at least ten heart-beats of the patient or a period of at least 10 seconds. This procedure can generally take place while the patient is connected to both a synchronized Hdp monitoring system and the programmable generator so that RRI values can be measured and HRV values can be calculated and recorded during the period of exposure or application. The HRV values can, however, also or alternatively be the initial data source to identify AM EMF signals and/or representative HRV variation values after software processing as is described above.

The above Hdp values measured during or after the above-identified exposures or applications to subjects or patients are herein referred to as exposure Hdp values post-exposure Hdp values, respectively.

The procedures above, as generally applied to multiple patients having a health condition, can provide multiple basal RRI values, multiple exposure RRI values and multiple post-exposure RRI values as related to the health condition or the prognosis of the quality of life, survival, or hospital admission of a patient. These multiple RRI values can in general be somewhat scattered values and, after calculation, can produce HRV values that are similarly scattered. Accordingly, for purposes of defining representative HRV variation values, such scattered values can be regularly submitted to the processing system so that the processing system can perform statistical computations that identify amplitude modulated electromagnetic frequencies using the representative HRV variation values.

In line with the above, the Hdp monitoring system provides means for software processing Hdp values for use in the identification of one or more amplitude modulated electromagnetic frequencies, the diagnosis of health conditions of a patient, or the prognosis of the quality of life, survival, or hospital admission of a patient. Identified amplitude modulated electromagnetic frequencies and representative HRV variation values are representative surrogate markers. Such representative surrogate markers are determined through the processing system from the Hdp monitoring system by measuring and recording Hdp values during non-exposure and exposure periods on patients pre-diagnosed and diagnosed to be either healthy or suffering from a known health condition.

Representative surrogate markers employed for the purpose of diagnosis, AM EMF signal identification, prognosis of the quality of life, survival, or hospital admission of a patient can be derived from computative combinations of information from representative basal RRI measured values, representative exposure RRI measured values, and/or representative post-exposure RRI measured values. Those computative combinations can be performed in the ILf.

The time periods of exposure or application of the AM EMF signals by means of a variable frequency programmable generator device may be within a broad range of frequencies; for example, AM EMF signals within a range between about 0.01 to about 150 MHz can require a short period of time for RRI values to be varied at any particular frequency value. Thus, consecutive exposures or applications of sections of the range of AM EMF signals may be required in order to identify AM EMF values at which basal, exposure and post-exposure HRV values actually occur during the heart-beat times at which RRI values are measured by the Hdp monitoring system and processed by the processing system to calculate the HRV values and to determine the representative HRV variation values.

In addition to being integrated within or coupled to the recording means as described above, the processing system can be located at a central server and connected to the Hdp monitoring system or a portable device by an encrypted web-based platform, which can perform the analysis based on recorded representative HRV variation values, received or communicated to the central server.

The following discussions of FIGS. 10-15 illustrate various examples of the Hdp monitoring system as described above and particular environments in which the monitoring system can be utilized.

Figure 10:
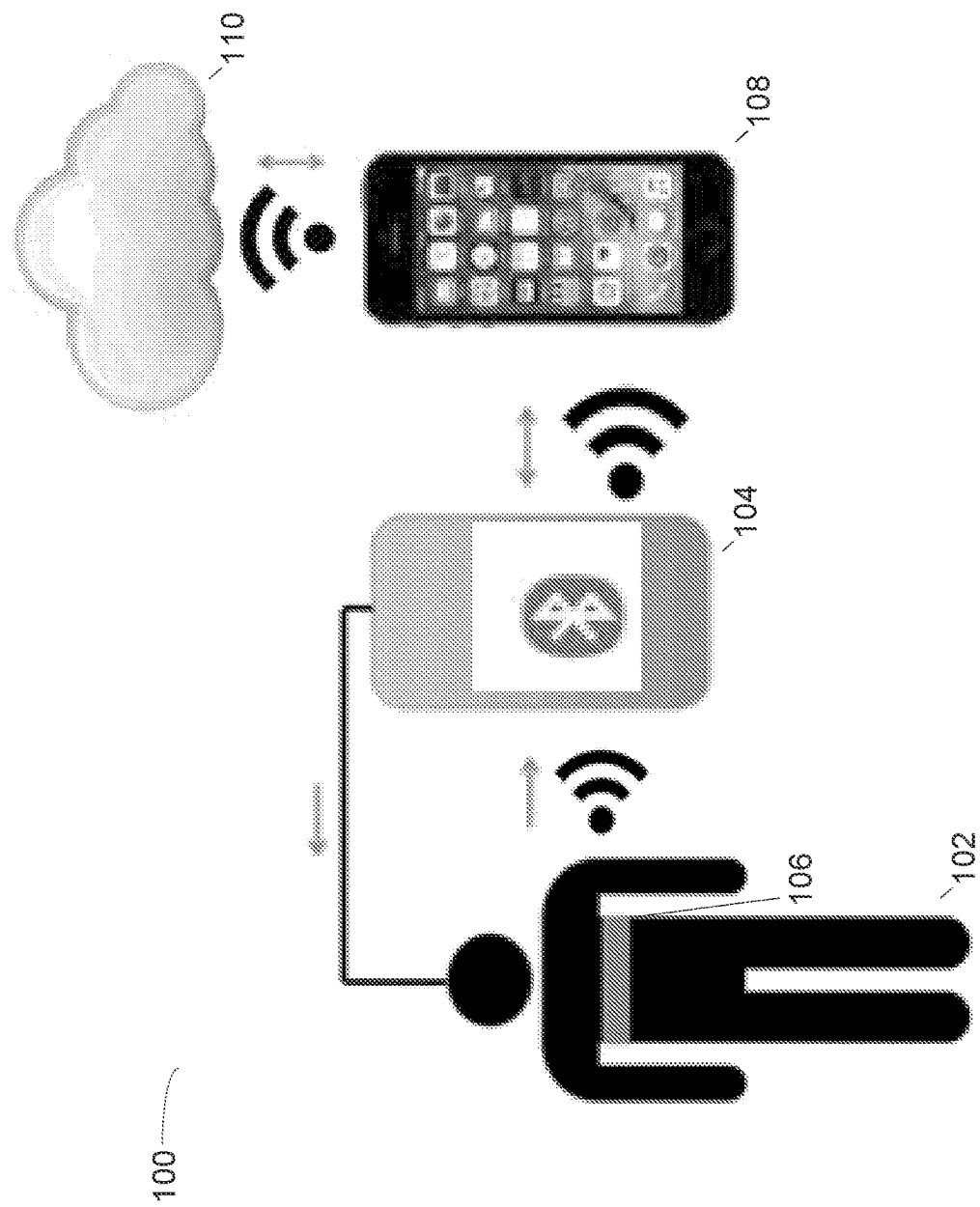
FIG. 10 depicts a sample use scenario for the portable medical device as described herein in accordance with an embodiment.

FIG. 10 illustrates a sample system 100 used to monitor a patient 102. In certain implementations, a portable medical device 104 can be operably connected to a sensor assembly 106 that is in contact with the patient 102. In various embodiments, the sensor assembly 106 can include an electrode belt that is strapped around the patient 102 (as shown in FIG. 10), an antenna, and other electrical sensor assemblies for applying electrical signals and detecting the electrical response in the patient 102 to which the sensor assembly 106 is associated. In some embodiments, the sensor assembly 106 may be a spoon-shaped antenna configured to be placed in the mouth of a patient 102. The medical device 104 can be configured to produce a set of electrical signals (e.g., via the programmable generator device described above) and transmit the signals to the patient 102 via the electrical sensor assembly 106. The electrical sensor assembly 106 can be configured to measure an electrical response produced by the patient 102 and return a value to the medical device 104 indicative of the measured electrical response. In certain implementations, the medical device 104 can transmit this information to an external computing device, such as a smartphone 108 or the computing device 600 illustrated in FIG. 21, for further processing. Additionally, in some examples, the external computing device can be operably connected to an encrypted network 110 for transmission of any processed information for remote storage and/or additional calculations by a remote computing device, such as a remote server.

In some embodiment, the portable medical device 104 can work in concert with an external computing device, such as is described above. In such an embodiment, the internal processing components of the portable medical device 104 can be reduced, thereby reducing the overall size of the portable medical device. However, in some embodiments, the portable medical device 104 may be designed such that it can perform analysis of the received electrical response from the patient 102.

Figure 11:
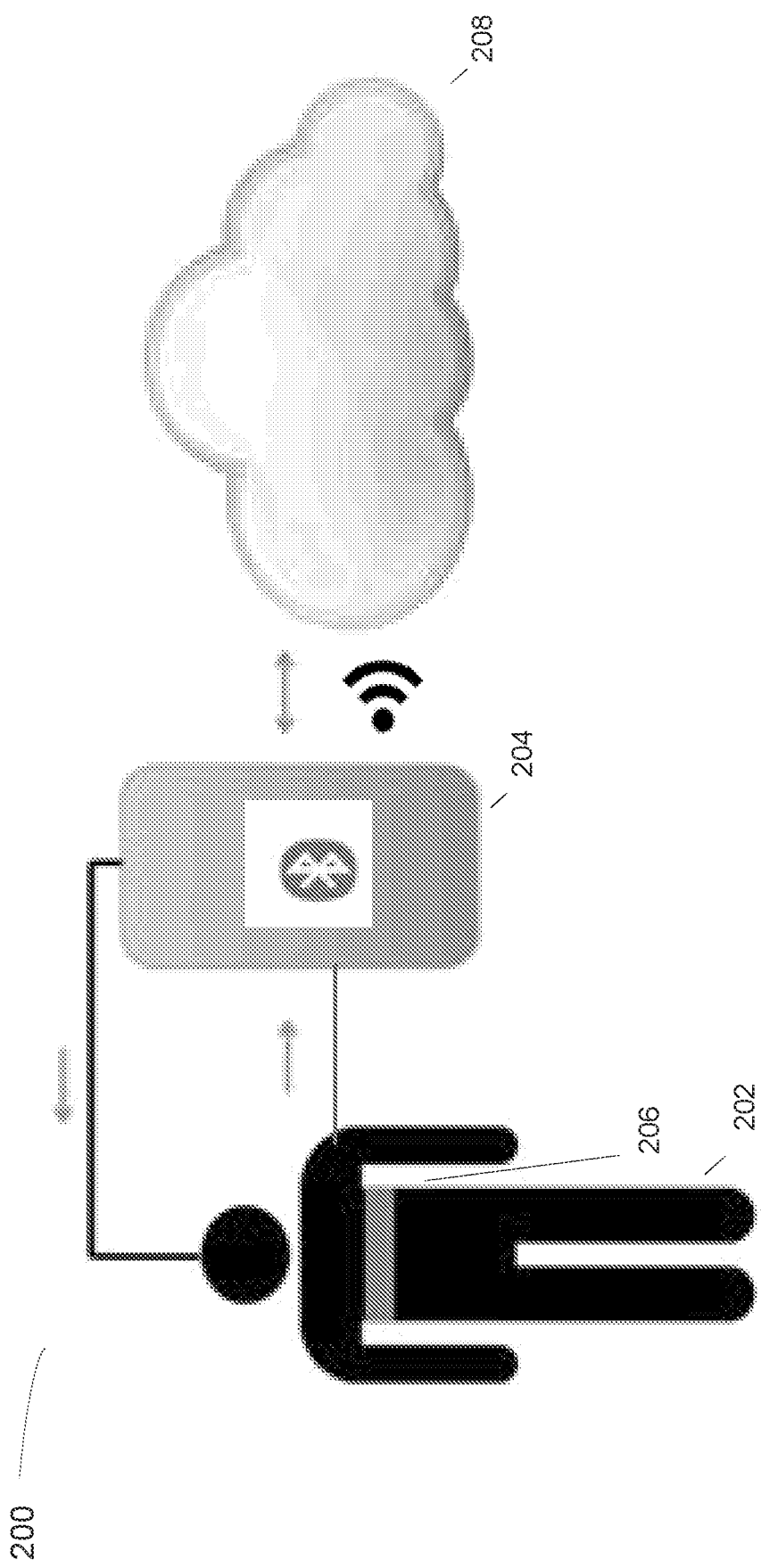
FIG. 11 depicts an alternate sample use scenario for the portable medical device in accordance with an embodiment.

FIG. 11 illustrates a sample system 200 used to monitor a patient 202. In certain implementations, a portable medical device 204 (similar to the portable medical device described above) can be operably connected to an electrical sensor assembly 206 that is in contact with the patient 202. As described above, the electrical sensor assembly 206 can include an electrode belt worn by the patient, an antenna, or the like. The medical device 204 can be configured to produce a set of electrical signals (e.g., via the programmable generator device as described above) and transmit the signals to the patient 202 via the sensor assembly 206. The sensor assembly 206 can be configured to measure an electrical response produced by the patient 202 and return a value to the medical device 204 indicative of the measured electrical response. However, unlike in FIG. 10, the medical device 204 can be configured to perform additional analysis on the returned value. Additionally, in some examples, the medical device 204 can be operably connected to an encrypted network 208 for transmission of any processed information for remote storage and/or additional calculations by a remote computing device, such as a remote server.

Figure 12:
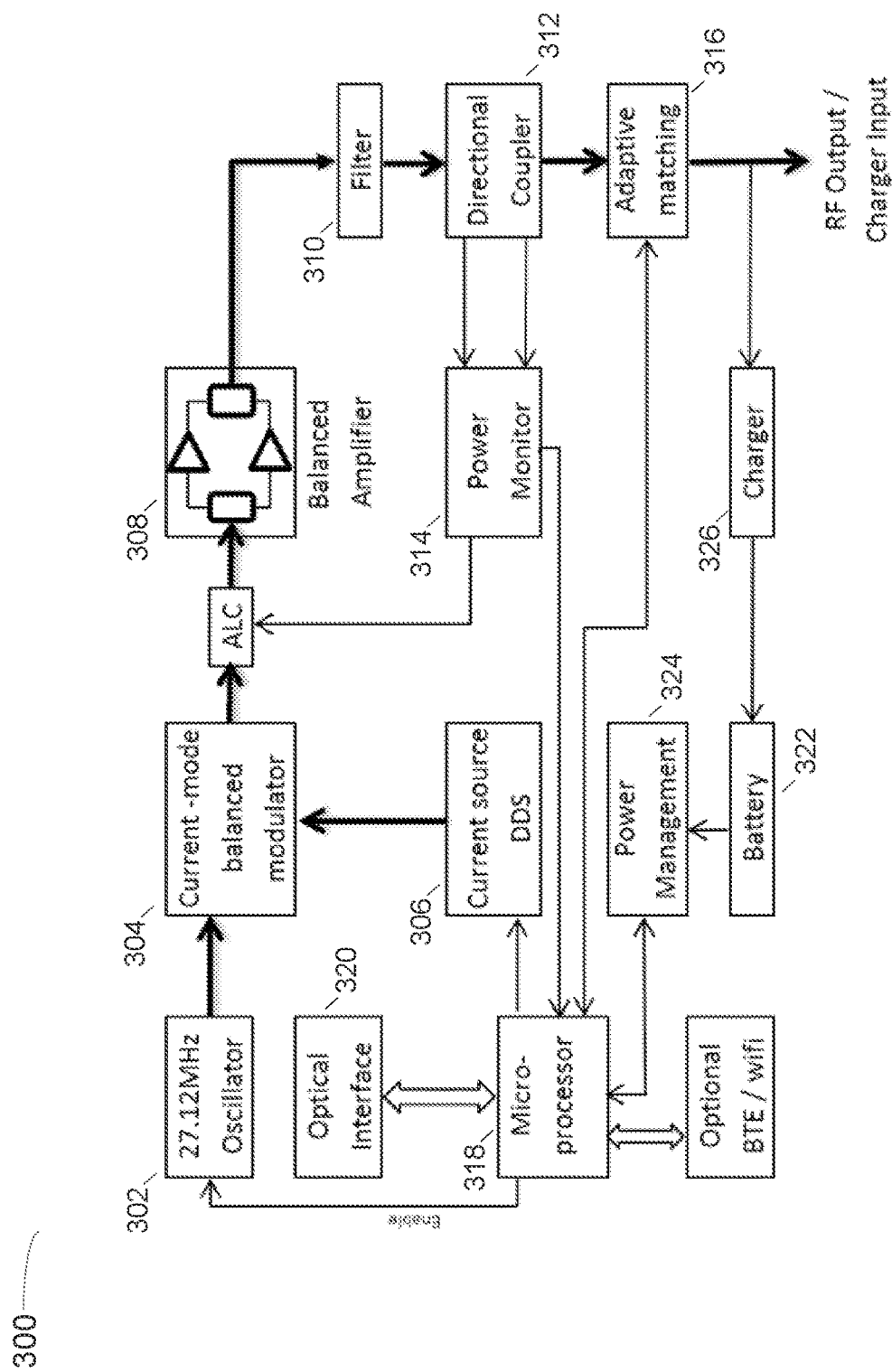
FIG. 12 illustrates a sample circuit diagram for the portable medical device in accordance with an embodiment.

FIG. 12 depicts an illustrative circuit diagram of a portable medical device 300 such as those described herein. The medical device 300 can include a fixed carrier frequency oscillator 302 and a current mode balanced modulator 304. In certain implementations, the frequency oscillator 302 can be configured to produce a 27.12 MHz signal. However, it should be noted that this signal frequency is provided by way of example only and can vary based upon the intended functionality of the portable medical device 300. In certain implementations, the frequency oscillator 302 can be configured to produce a signal having a frequency between 1.0 mHz and 1.0 Hz, 1.0 Hz and 1.0 kHz, 1.0 kHz and 1.0 MHz, 1.0 MHz and 1.0 GHz, and/or frequencies above 1.0 GHz.

In some examples, the modulator 304 can be modulated by a sinusoidal current generated by a direct digital synthesiser 306, thereby producing a modulated carrier signal. In certain implementations, the sinusoidal current can have a 10 MHz frequency resolution and a frequency accuracy of 10 ppm (parts per million). In some embodiments, the frequency accuracy may be 1 ppm. In some embodiments, the frequency accuracy may be 0.1 ppm. In each of these embodiments, the generated signal can be defined as "highly specific" if it conforms to the stated accuracy.

The modulated carrier signal can be amplified by an amplifier 308. In certain implementations, the amplifier 308 can be a class AB balanced RF amplifier. The output of the amplifier 308 can be filtered by a filter 310 to reduced harmonic content. The filtered signal may be processed by a directional coupler 312 and passed to a power monitor 314 and an adaptive matching component 316. The power monitor 314 can be configured to monitor the current power level of the filtered signal and, if necessary, provide an adjustment signal to a microprocessor 318. The microprocessor 318 can alter the sinusoidal current generated by the synthesizer 306, thereby altering the output power. In some implementations, the microprocessor 318 can be operably connected to an optical interface 320 of the medical device 300 that is configured to display information received from the microprocessor. In some examples, the optical interface 320 can include an input device, such as a touchscreen, to receive input information from a user of the medical device 300.

The medical device 300 can also include a battery 322 and a power management component 324 configured to manage and distribute power generated by the battery. In some examples, the battery 322 can be a rechargeable battery coupled to a charging component 326 configured to provide a charging signal to the battery when the medical device 300 is connected to an exterior power source.

As noted above, the output of the directional coupler 312 can be passed to an adaptive matching component 316. The adaptive matching component 316 can also be connected to and controlled by the microprocessor 318. Upon receiving instructions from the microprocessor 318, the adaptive matching component 316 can be configured to provide an RF output signal to one or more sensors positioned on the patient's body.

In certain implementations, the filtered power can be maintained at a desired level by means of an automatic level control loop including, as described above, the power monitor 314 and the microprocessor 318, ensuring that the change in voltage as the battery 322 discharges does not significantly affect the treatment. The reflected power is minimized by adjusting the adaptive matching component 316 to ensure efficient transfer of therapeutic signals to the patient. In some examples, the medical device 300 can be controlled directly from a computer over an optical link using a frequency and duration command and return to a low power state after a defined time period.

Figure 13:
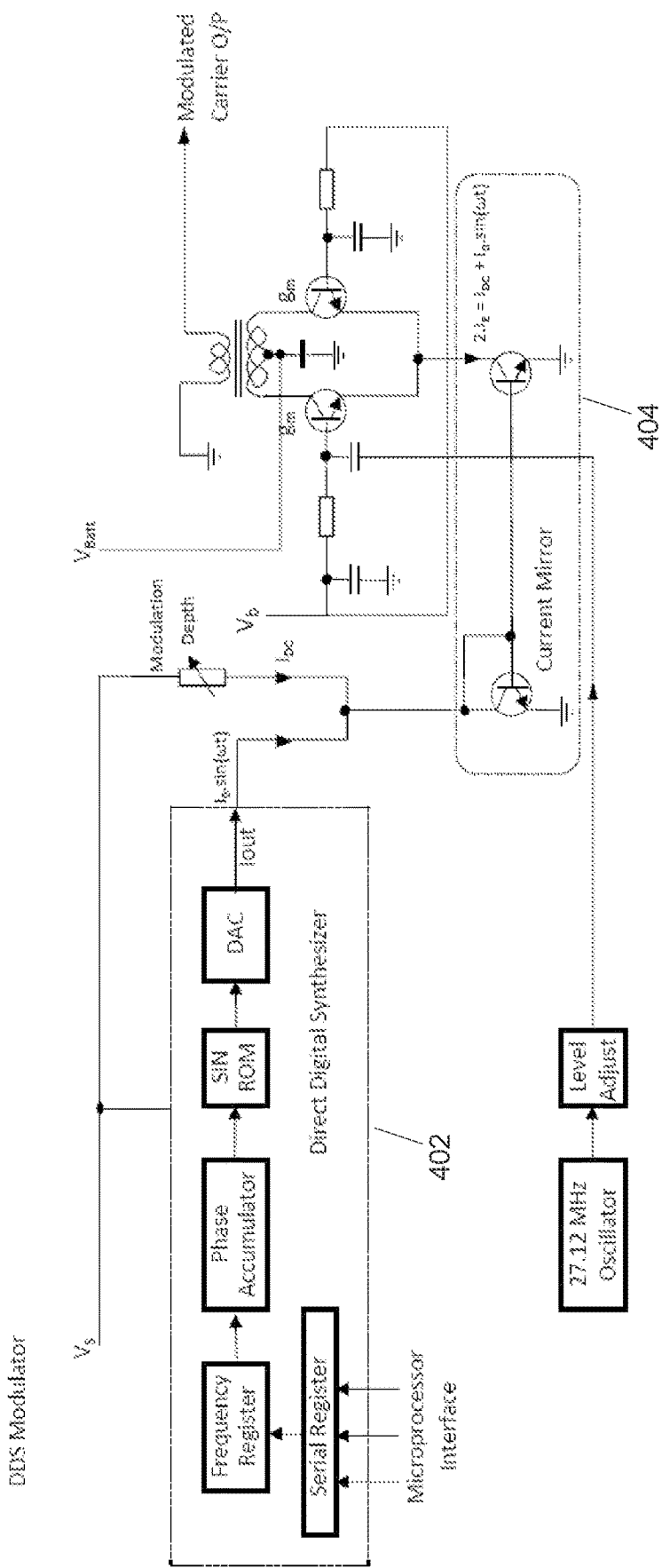
FIG. 13 illustrates a sample circuit diagram for a signal modulator in accordance with an embodiment.

FIG. 13 illustrates a sample circuit diagram for producing a modulated carrier signal as described above in the description of FIG. 12. As noted above, the modulation sinusoidal signal can be generated by a direct digital synthesizer (DDS) 402, the DDS includes an integrated current output digital to analog converter (DAC). In certain implementations, the modulation sinusoidal signal can be in the frequency range of about 10 Hz to about 50 kHz.

A current mirror 404 can be used to drive the current mode balanced amplitude modulator. The input to the current mirror 404 can include two components, the sinusoid from the DDS 402 and a DC current which is adjustable to set the modulation depth to a desired range, for example, 85% to 90% of the original signal. The output from the current mirror 404 can form the tail of a transistor pair operating as a high impedance current source with current $2I_E = I_{DC} + I_0 \sin(\omega t)$, the current setting the gain, $g_m$, of the transistor amplifiers in the differential pair. The bases of the transistors can be biased at voltage $V_b$. One transistor can be fed with the carrier signal at 27.12 MHz, and the second transistor can be held at a small signal ground. The carrier signal can be amplified differentially with a gain varying in sympathy with the modulation signal, and the two outputs can be combined using, for example, a center-tapped balun transformer. The combined modulated signal can attain signal levels twice as high as would be available from a single-ended configuration for the same battery voltage. The output of the modulator is thus the desired AM modulated signal, e.g., a 27.12 MHz carrier signal.

Figure 14:
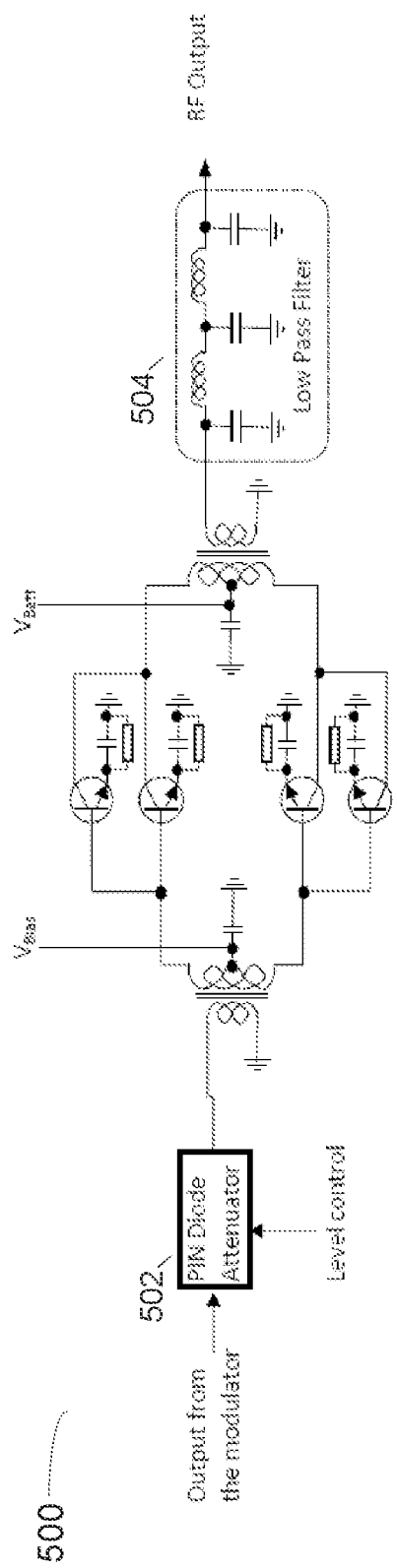
FIG. 14 illustrates a sample circuit diagram for an amplifier in accordance with an embodiment.

FIG. 14 illustrates a sample circuit diagram for an amplifier 500 (e.g., amplifier 308 as described above in the description of FIG. 12). The signal from the current mode modulator can be amplified to achieve a required signal level using a balanced amplifier 500.

The gain of the amplifier 500, and hence the output level, is somewhat dependant on the battery voltage. As such, the amplifier 500 can be preceded by a variable attenuator 502 that is adjustable to maintain a constant output power as the battery discharges. The attenuator 502 can use a shunt PIN diode in a T attenuator configuration in which a higher current through the diode results in higher attenuation. As noted above, in certain implementations, the amplifier 500 can be a class AB balanced design with parallel RF devices to increase the current capacity.

The input transformer can convert the input from a single-ended signal to a balanced signal and can match the input impedance of the devices. Each pair of devices can amplify one half cycle of the signal. As such, the output signal can approach twice the battery voltage in peak amplitude before clipping. The output transformer can combine the two signals to produce the final output signal. The class AB bias ensures that any cross-over distortion is minimized. The impedance transformation ratio of the output balun transformer can be chosen such that the desired output power can be generated given the limited supply (battery) voltage. The balanced amplifier design suppresses even-order distortion products; however, odd-order harmonics can be suppressed using a low pass filter 504, for example, a 5th order low pass filter.

Figure 15:
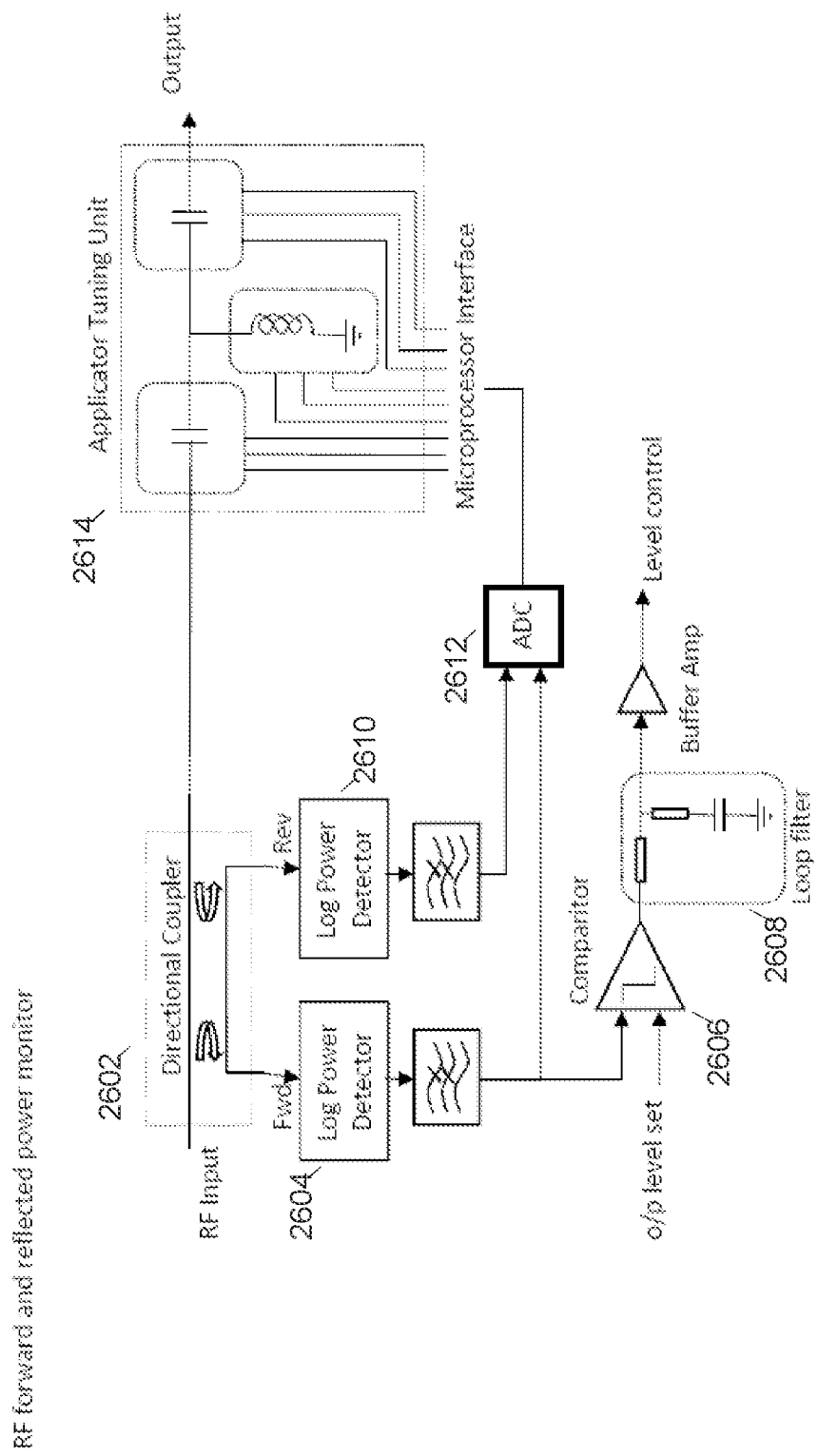
FIG. 15 illustrates a sample circuit diagram for a power monitor in accordance with an embodiment.
Figure 16:
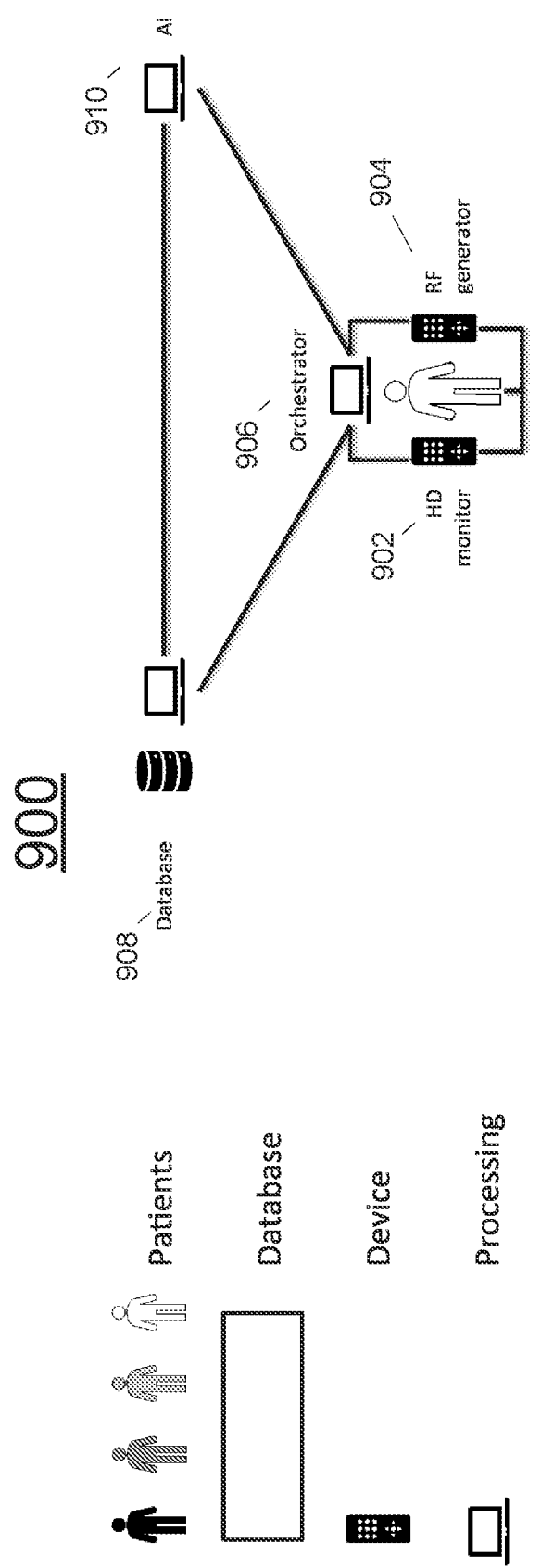
FIGS. 16A-B illustrate a flow diagram for a signal modulator in accordance with an embodiment.

FIG. 15 illustrates a sample circuit diagram for monitoring the RF forward and reflected power produced by the amplifier. The output from the amplifier (e.g., amplifier 500) can be sampled using a directional coupler 2602, and the forward signal detected using a log power detector 2604 with, for example, >30 dB dynamic range. The output signal can be low-pass filtered to obtain the average envelope power from the amplitude modulated signals. In certain implementations, the average envelope power can be measured by an analog-to-digital converter (ADC) 2612 to allow the microprocessor to report the value to the control computer for use in a control loop that maintains a constant output power as the battery voltage changes.

In some examples, the detected voltage, which equates to the average output power, can be compared to the desired value using a comparator 2606. The digital output can be filtered using a passive lead-lag loop filter 2608 with appropriate time constants to maintain stability of the control loop. The output of the loop filter 2608 can be buffered and used to drive a PIN diode attenuator, such as 502 in FIG. 14, to adjust the overall gain to obtain the desired output power.

The directional coupler 2602 can also sample the power reflected from the load, in this case the applicator, using a log power detector 2610. The average level can be determined using a low-pass filter and can be sampled using an ADC 2612. The control computer can compare the forward and reflected powers and adjust an applicator tuning unit 2614 to find the settings with the lowest reflected power or optimum power transfer to the patient. Various algorithms can be used. For example, the control computer can adjust each of the three elements in turn, up or down in value, and determine whether the reflection reduces or not, repeating this process iteratively until a minimum is found.

As described herein, patient prognosis or diagnosis may be performed with the aid of measured Hdp values and recorded Hdp values. The recorded Hdp values may be measured in a number of patients that either are pre-diagnosed to be suffering from an identified poor health condition or are in a healthy condition. The Hdp values may be stored at determined times and for determined periods of time, as described in greater detail below (FIGS. 16-19).

In an embodiment, a system includes an Hdp monitoring system used to measure and record Hdp values and a frequency generator configured to provide one or more defined frequencies to a patient via radio frequency carrier signals.

In an embodiment, the system may identify one or more AM EMFs, which are a subgroup of the RF carrier signals. The one or more AM EMFs may be used to influence cellular functions or malfunctions in a warm-blooded mammalian subject. The exposure of a warm-blooded mammalian subject to the one or more AM EMFs may cause representative Hdp variation values to change in a manner that indicates whether or not one or more RF carrier signals have a potential biological effect in the warm-blooded mammalian subject. The specificity of changes in representative Hdp variation values may be a surrogate marker for the prognosis or diagnosis of the warm-blooded mammalian subject.

In an embodiment, the system may store one or more groups of identified amplitude modulated electromagnetic frequencies in a server connected by a protected Internet-based platform to form a library of amplitude modulated electromagnetic frequencies (ILf). The stored data may be combined, organized, compared and characterized for use in the diagnosis or prognosis of a health condition of a patient, or the prognosis of the quality of life, survival, or hospital admission of a patient.

The integrated frequency generator can be configured to emit or expose a warm-blooded mammalian subject to one or more highly specific frequency RF carrier signals. Further, the generator can include a programmable generator that is activatable by electrical power as part of an integrated system. The programmable generator may be employed to influence cellular functions or malfunctions in a warm-blooded mammalian subject. The programmable generator may include one or more controllable low-energy electromagnetic energy generator circuits configured to generate one or more RF carrier signals. One or more microprocessors or integrated circuits that include or communicate with the one or more generator circuits are provided. In an embodiment, the one or more microprocessors may also be used to control the transmission and reception of control information from a processing system. In an embodiment, the one or more generator circuits may include one or more AM frequency control signal generators configured to control amplitude modulated variations of the one or more RF carrier signals. The one or more generator circuits may further include one or more programmable AM frequency control signal generators configured to control the frequency at which the amplitude modulations are generated.

The system may further include a processing system configured to integrate and synchronize the Hdp monitoring system and the one or more programmable generators. Various Hdp values measured and recorded by the Hdp monitoring system while exposing a warm-blooded mammalian subject to one or more RF carrier signals emitted by the one or more programmable generators may be processed by the processing system. The information resulting from such processing may be stored, for example, in the ILf. The processing system may further control, synchronize and load a control program into the one or more programmable generators with a specific series of AM EMF signals. As such, the processing system may integrate and synchronize the Hdp monitor, the ILf and the one or more programmable generators to support an integrated solution.

In an embodiment, the processing system and the ILf may be part of a server connected to the remainder of the system by a protected web platform. The ILf can be used for storing, combining, organizing, comparing, characterizing and processing AM EMF and recorded representative Hdp variation values. The ILf can further be used for storing, combining, organizing, comparing, characterizing and processing quality of life, survival, or hospital admission values. The ILf may store and organize a series of AM EMF and representative Hdp variation values identified in a warm-blooded mammalian subject or patient. The ILf may store and organize a series of quality of life, survival, or hospital admission values identified in a warm-blooded mammalian subject or patient. One or more series of AM EMF signals may then be loaded into the one or more programmable generators. The one or more programmable generators may accurately control the emission of the frequency of the amplitude modulations with an accuracy of at least 1000 parts per million (ppm) relative to one or more determined or predetermined reference AM frequencies. In an embodiment, the AM EMF may be within a range of 0.01 Hz to 150 kHz. The processing system may further include a connection or a coupling position. The connection or coupling position may be used to connect or couple the processing system to an electrically conductive applicator that applies the one or more amplitude-modulated low-energy emissions at the accurately controlled modulation frequencies to the warm-blooded mammalian subject.

A frequency synthesizer may be used to generate a particular frequency or a series of frequencies with precision. For example, a user may use a keyboard or other input device to select one or more frequencies, which in turn may cause a circuit to turn a generated signal ON or OFF within well-defined time intervals.

In an embodiment, a processing system processes Hdp values measured and recorded by an Hdp monitoring system connected to warm-blooded mammalian subject during the exposure to one or more RF carrier signals emitted by a programmable generator. The Hdp monitoring system may measure and record Hdp values for further processing. The processing system may incorporate one or more algorithms that analyze the recorded Hdp values obtained by the Hdp monitoring system. The processing system uses various measured and recorded Hdp values of the subject and identifies AM EMFs, characterized by recognizable patterns of Hdp variation value changes, herein referred to as representative Hdp variation values. The processing system generally identifies the various measured and recorded Hdp values of the patient using electrodes placed in topical contact with various determined parts of the body as part of the Hdp monitoring system. The Hdp monitoring system further comprises a recording component that records the various identified measured Hdp values of the patient. In an embodiment, the recording component may store the measured Hdp values in a storage device of the Hdp monitoring system. In an alternate embodiment, the recording component may store the measured Hdp values in any storage device on which the various identified measured Hdp values of the patient can be recorded for immediate and/or future processing. Hdp values may include the values of, for example, one or more of the following hemodynamic parameters: RR interval (interval from an R peak to the next R peak as shown, for example, on an ECG) (RRI); heart rate (HR); systolic blood pressure (sBP); diastolic blood pressure (dBP); median blood pressure (mBP); pulse pressure (PP); stroke volume (SV); cardiac output (CO); and total peripheral resistance (TPR).

In an embodiment, the processing system may include a device synchronizer, a data aggregator, a storage device and/or a storage interface, and an interface controller. The interface controller may be responsible for matching the Hdp values and the exposure to one or more high specific frequency radio frequency carrier signals (synchronization). Additionally, or alternatively, the interface controller may be responsible for consolidating the records (data aggregation) to be stored (storage) for further processing (interface controller) in such a way that Hdp values are linked to an exposure to one or more high specific frequency radio frequency carrier signals from which such Hdp values were measured. The Hdp monitoring system and the programmable generator may be connected via the interface controller. The modules corresponding to synchronization and data aggregation, and the storage interface may be packed as a portable integrated hardware solution.

In another embodiment, the processing system may include, inter alia, two components: a statistical mining component and a computational statistics/evolutionary game theory component. It should be noted that, as used herein, computational statistics refers to various types of computational statistics techniques including, for example, deep machine learning. The statistical mining component may include a series of mathematical procedures based on discriminant analysis and support vector machine (SVM). Hdp values may be constant selected metric variables and their dependent new attributes that are analyzed based on different well-established statistical methods. Using multivariate discriminant analysis and other coordinate transformation based on relevant component analysis, Hdp values may be represented as centroids of representative Hdp variation values with well-defined threshold values in order to optimize common metrics. The computational statistics/evolutionary game theory component may include permanently refined cluster analysis and updated mathematical algorithms that, or by new discriminating attributes, perform cutoff refining for (1) identifying patterns of responses for health condition-specific frequencies or for prognosticating the quality of life, survival, or hospital admission of a patient, herein named representative Hdp variation values, and (2) storing representative Hdp variation values and the corresponding health condition-specific or quality of life, survival, or hospital admission frequencies. These components may be implemented on a central and secure server-side system connected to the integrated hardware solution via encrypted communication over a network, such as the Internet.

In yet another embodiment, an ILf may be located in the central and secure server system. In an embodiment, the library may be connected to all instances of the integrated hardware solution via encrypted communication over a network, such as the Internet. In such an embodiment, the network solution may provide a real-time, integrated and evolutionary system combining all working devices. Permanent updated de-identified patient demographic and clinical information data gathered from physician and patient-reported outcomes (e.g., quality of life, survival, or hospital admissions) combined with records of representative Hdp variation values and the correspondent AM EMFs and the data may be stored in the ILf. Threshold values for representative Hdp variation values may be refined based on newly added values. Such data may be structured and processed to refine the procedures for diagnosis or prognosis of a health condition of a patient. ILf may have computing capabilities to support computational statistics for pattern recognition and evolutionary game theory for identification of points of equilibrium, which characterize the best possible matching for each series of AM EMFs and/or representative Hdp variation values and corresponding to the diagnosis and prognosis outcome information. Refinement procedures can be implemented as programs, which take into account patient segmentation. The programmable generator is connected by the interface controller in the processing system in order to transfer data between the processing system and the programmable generator. Refined procedures are then downloaded back to the processing system module of the integrated hardware solution in order to re-program the programmable generator.

The interface controller may connect the programmable frequency generator to the processing system in order to allow for the transfer of data. Refined procedures may be downloaded to the processing system in order to update the programmable frequency generator prior to or during a treatment session.

In an embodiment, a diagnosis of a health condition of a patient or prognosis of the quality of life, survival, or hospital admission of a patient may be determined based on one or a group of AM EMF and/or representative Hdp variation values identified by the processing system. In an embodiment, a plurality of measured and recorded Hdp values may be submitted to the processing system during the exposure of the patient to one or more RF carrier signals. The processing system may identify AM EMF and/or representative Hdp variation values in a patient diagnosed with a health condition. In an embodiment, the identified AM EMF and representative Hdp variation values may be stored in the ILf. The warm-blooded mammalian subject, during exposure to a selected group of AM EMF may have various Hdp values that are measured and recorded by the Hdp monitoring system processed to identify the characteristic hemodynamic response pattern to AM EMF exposure. The processing system identifies representative Hdp variation values related to the selected group of AM EMF. The processed information may be stored in the ILf for instant and/or future database comparisons. The diagnosis identification may be the result of searching for patterns of response that are consistent with a specific health condition of a patient. The prognosis identification may be the result of searching for patterns of response that are consistent with a specific quality of life, survival, or hospital admissions of a patient. The processing system may diagnose a health condition of a patient by incorporating a series of mathematical algorithms that analyze the recorded Hdp data obtained by the Hdp monitoring system. The processing system may prognose the quality of life, survival, or hospital admission of a patient by incorporating a series of mathematical algorithms that analyze the recorded Hdp data obtained by the Hdp monitoring system.

In another embodiment, a user may search for one or more AM EMFs. The searching procedure may be conducted during the exposure of a patient to one or more RF carrier signals. For example, searching for one or more AM EMFs may include a process that involves the Hdp monitoring system reviewing measured and recorded Hdp values stored in the processing system during exposure of the patient to one or more RF carrier signals. The searching procedure for one ore more AM EMFs may involve the application of mathematical algorithms to determine a series of specific frequencies to be provided by the programmable generators. In an embodiment, the searching process may include processing of measured and recorded Hdp values by the Hdp monitoring system during the exposure to a series of AM EMF, such as a subgroup of RF carrier signals, produced by a programmable generator in a warm-blooded mammalian subject with an unknown health condition or a patient with a known health condition. With respect to the exposure of a subject or patient to a predetermined sequence of one or more RF carrier signals, the term "accurately controlled" means that modulated low-energy electromagnetic emissions are modulated to within a resolution of at most about 1 Hz of higher frequencies (greater than about 1000 Hz). For example, if a determined or predetermined modulation frequency to be applied to the warm-blooded mammalian subject is about 2000 Hz, accurate control of such modulated low-energy emission requires the generated frequency to be between about 1999 Hz and about 2001 Hz. The processing system identifies AM EMFs and representative Hdp variation values during the searching procedure.

In an embodiment, one or more new AM EMFs may be discovered. The discovery procedure may be conducted during exposure of an individual or patient to one or more high specific frequency RF carrier signals. Discovery of new AM EMFs may include having the processing system received measured and recorded Hdp values from the Hdp monitoring system during exposure to one or more RF carrier signals. The discovery of new AM EMFs may further involve the application of mathematical algorithms to determine a series of specific frequencies by the programmable generators. In an embodiment, the searching process may process measured and recorded Hdp values from the Hdp monitoring system during exposure to a series of AM EMFs that are a subgroup of RF carrier signals produced by a programmable generator in a warm-blooded mammalian subject with a known health condition. In an embodiment, the processing system identifies AM EMFs and representative Hdp variation values during the process of discovering new AM EMFs.

In an embodiment, a diagnosis of a health condition of a patient, or the prognosis of the quality of life, survival, or hospital admission of a patient may be determined based on one or a group of AM EMFs and/or representative Hdp variation values identified by the processing system. In an embodiment, a plurality of measured and recorded Hdp values may be submitted to the processing system during the exposure of the patient to one or more high specific frequency RF carrier signals. The processing system may identify AM EMFs and/or representative Hdp variation values in a patient diagnosed with a health condition. The processing system may identify AM EMFs and/or representative Hdp variation values in a patient having a quality of life, survival outcome, or hospital admission outcome. In an embodiment, the identified AM EMFs and representative Hdp variation values may be stored in the ILf. The warm-blooded mammalian subject, during exposure to a selected group of AM EMFS may have various Hdp values that are measured and recorded by the Hdp monitoring system processed to identify the characteristic hemodynamic response pattern to AM EMFs exposure. The processing system identifies representative Hdp variation values related to the selected group of AM EMFs. The processed information may be stored in the ILf for instant and/or future database comparisons. The diagnosis identification may be the result of searching for patterns of response that are consistent with a specific health condition of a patient. The prognosis identification may be the result of searching for patterns of response that are consistent with a quality of life, survival outcome, or hospital admission outcome of a patient. The processing system may diagnose a health condition of a patient or prognose the quality of life, survival, or hospital admission of a patient by incorporating a series of mathematical algorithms that analyze the recorded Hdp data obtained by the Hdp monitoring system.

In another embodiment, a user may be enabled to search for AM EMFs. The searching procedure may be conducted during the exposure of a patient to one or more RF carrier signals. For example, searching for one or more AM EMFs may include a process that involves the Hdp monitoring system reviewing measured and recorded Hdp stored in the processing system during exposure of the patient to one or more RF carrier signals. The searching procedure for one or more AM EMFs may involve the application of mathematical algorithms to determine a series of specific frequencies to be provided by the programmable generators. In an embodiment, the searching process may include processing of measured and recorded Hdp values by the Hdp monitoring system during the exposure to a series of specific frequencies, such as a subgroup of high specific frequency RF carrier signals, produced by a programmable generator in a warm-blooded mammalian subject with an unknown health condition or a patient with a known health condition.

In yet another embodiment, the system may be used to construct and update the ILf. The process used to construct and update the ILf library with frequencies may use the processing system to identify AM EMFs and/or representative Hdp variation values in warm-blooded mammalian subjects. The processing system may store identified AM EMFs and representative Hdp variation values in a central server connected by a protected Internet platform. The ILf may store newly identified AM EMFs from warm-blooded mammalian subjects with a known health condition. The stored AM EMFs that originated from warm-blooded mammalian subjects with known health conditions may undergo processing to allow future diagnosis of a healthy condition of a patient or prognosis of the quality of life, survival, or hospital admission of a patient. For example, one or more AM EMFs identified in a patient diagnosed with a specific health condition may be used with other warm-blooded mammalian subjects for diagnosis proposes. As an additional example, one or more AM EMFs identified in a patient with a quality of life, survival, or hospital admission prognosis may be used with other warm-blooded mammalian subjects for prognosis proposes.

The above-mentioned one or more RF carrier signals may be EMF output signals produced by a control program loaded into the programmable generator that is capable of generating EMF output signals at certain predetermined AM frequencies. The subjects or patients are most preferably exposed to the EMF output signals during heart-beat times over a determined period of time, most preferably over the time of at least ten heart-beat times of the patient or a period of at least 10 seconds. In some embodiments, the subjects or patients are exposed to the EMF output signals or the EMF output signals are applied to patients over the time of at least three heart-beat times of the patient or a period of at least 3 seconds. This procedure would generally take place while the patient remains connected to or is reconnected to both the synchronized Hdp monitoring system and the programmable generator of the system so that Hdp values may be measured and recorded during the period of exposure or application. The Hdp values may, however, also or alternatively be the data source to identify AM EMFs and/or representative Hdp variation values after performing software processing.

The time periods of exposure or application of EMF frequency output signals by means of a variable frequency programmable generator device within a broad range of frequencies; for example, EMF frequencies within a range between from about 0.01 Hz to about 150 MHz, may require a short period of time for Hdp values to be varied at any particular frequency value. Thus, consecutive exposures or applications of sections of the range of EMFs may be required in order to identify EMF values at which basal, exposure and post-exposure Hdp value variations occur.

The system may further include an output signal frequency measurement and recording system that measures and records frequency values at which Hdp variation values of at least some of the Hdp values are exhibited, herein referred to as threshold values. Similarly, an Hdp value recorder may measure and record each of the measured values for each of the identified Hdp values, preferably separately of one another, before, during or after the period of time of exposure to or application of output signals to the patient.

The system may further include a processing system component integrated with or coupled to the Hdp value recorder before, during or after performing or exposing the patient to a cellular excitation procedure. The processing system component may include a program-controlled calculator that performs a series of mathematical analyses of various of the recorded Hdp values to obtain representative surrogate values, such as the identification of AM EMFs and representative Hdp variation values for each of the different recorded Hdp values. In some embodiments, the processing system component may make a determination of ratios between different representative Hdp values and compare either or both of the representative Hdp values or the ratios between different values with predetermined representative values or ratios (threshold values) characteristic of AM EMF and/or representative Hdp variation value changes that occur while exposing the patient to a cellular excitation procedure, predetermined in patients known to be healthy or known to be suffering from or likely to develop an identified poor health condition. The comparison of calculated representative surrogate values, such as recorded Hdp values or ratios and identified AM EMF and/or representative Hdp variation values in patients diagnosed with the same health condition, which match with predetermined representative Hdp values or ratios and/or identified AM EMF and/or representative Hdp variation values, leads to providing an indication of a diagnosis or prognosis of a health condition of a patient.

The processing system component may be located at a central server connected by a protected web platform, which may perform the analysis based on recorded Hdp information, received or communicated to the center.

Figure 20:
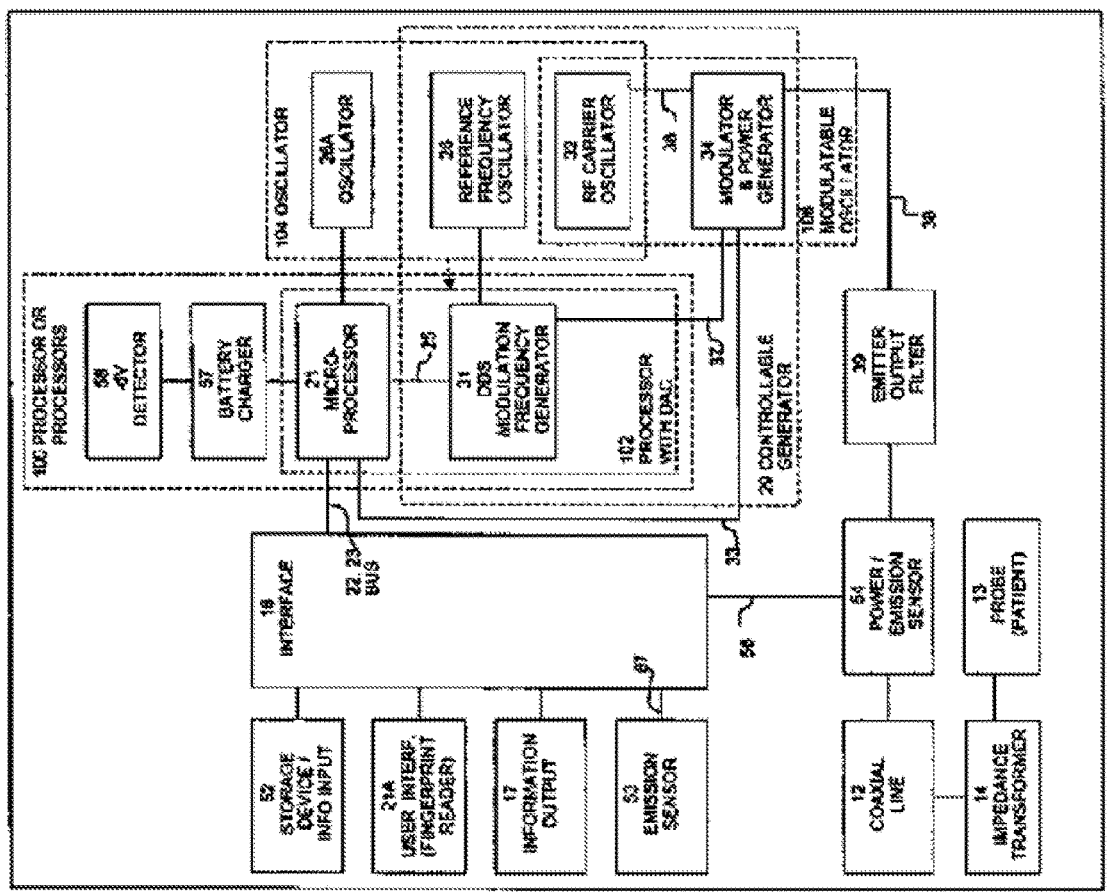
FIG. 20 depicts an illustrative schematic structure for an integrated medical system according to an embodiment.

FIG. 20 depicts an illustrative schematic structure for an integrated medical system according to an embodiment. As shown in FIG. 20, a system for diagnosing a health condition of a patient or prognosticating the quality of life, survival, or hospital admission of a patient may include an Hdp monitoring system and a frequency generator. In an embodiment, the system may further include a processing system.

The Hdp monitoring system determines a cardiovascular performance reserve for each individual patient. In an embodiment, the Hdp monitoring system may receive input physiological data from a patient. The input physiological data may be used to obtain a parameter Z which is or approximates a product of the patient's Stroke Volume (SV) and the patient's Systemic is Vascular Resistance (SVR). The Hdp monitoring system may further provide a value representing e Respiratory Rate (RR) of the patient. The RR value may be determined by one or more measurement using a dedicated device, a calculation performed using the input physiological data or manually by using a best estimate, such as making an estimate based on the heart rate of the patient.

The system described herein may be an integrated solution having a patient-side component and a server-side component. The patient-side component may include the Hdp monitoring system connected to the programmable generator. Both the Hdp monitoring system and the programmable generator may be connected to the processing system to enable synchronization of the devices and allow for compatible data aggregation. The server-side component may be connected with the patient-side component via the protected web-based platform and may provide statistical computation and data storage.

In certain implementations, the radio frequency generator can be configured to measure and store reflection power values during exposure that are synchronized with Hdp monitoring values for further computations and data storage, as described in additional detail below.

The two components of the system may enable bidirectional data transfer in real time as described above. For example, once the programmable generator is loaded with one or more control programs of selected series of AM EMFs, the programmable generator may be disconnected from the integrated solution to enable outpatient use. The programmable generator may be reconnected to the integrated solution to permit batch upload of update data and to allow automatic treatment profiling to be transferred back to the processing system.

Referring back to FIG. 20, the Hdp monitor may provide a method for determining a cardiovascular performance reserve for each individual patient. The method may include a) receiving input physiological data from the patient used to determine a parameter Z which is or approximates the product of the Stroke Volume (SV) and the Systemic Vascular Resistance (SVR); b) providing a value representing the Respiratory Rate (RR) of the patient, here the Respiratory Rate (RR) value is provided by measurements using dedicated device(s), calculations from the input physiological data or manually by using best estimate, c) performing electrocardiography (ECG) and photoplethysmography (PPG), where ECG measures the bio-potential generated by electrical activity of the heart and PPG senses the rate of blood flow, and d) determining HRV based on oscillation in consecutive cardiac cycles.

The system 11 includes an electrically conductive applicator 12, 13 for applying one or more electromagnetic emissions to the warm-blooded mammalian subject. There are a number of different forms of applicators that may include an electrically conductive probe 13 that forms a close contact with a subject undergoing treatment. The probe 13 may be connected to an electromagnetic energy emitter (see also FIG. 21) through a coaxial cable 12 and an impedance-matching transformer 14.

Electronic system 11 may also include a connector or coupler for connection to a programmable device, such as a computer or an interface or receiver 16 adapted to receive an application storage device 52 such as, for example, magnetic media, semiconductor media, optical media or mechanically encoded media, or emissions programmed with control information employed to control the operation of system 11 so that the desired type of low-energy emission therapy is applied to the patient.

The application storage device 52 can be provided with a microprocessor which, when applied to the interface 16, operates to cause the system 11 to apply the desired low-energy emission therapy. The application storage device 52 is provided with a microprocessor which is used in combination with microprocessor 21 within system 11. In such case, the microprocessor within the application storage device 52 enables the device 52 to communicate with the system 11 and other central servers.

The system 11 may also include a display 17 that can display various indications of the operation of the system. In addition, the system 11 may include on and off power buttons 18 and 19 and/or a user interface 21A (refer to FIG. 21).

Figure 21:
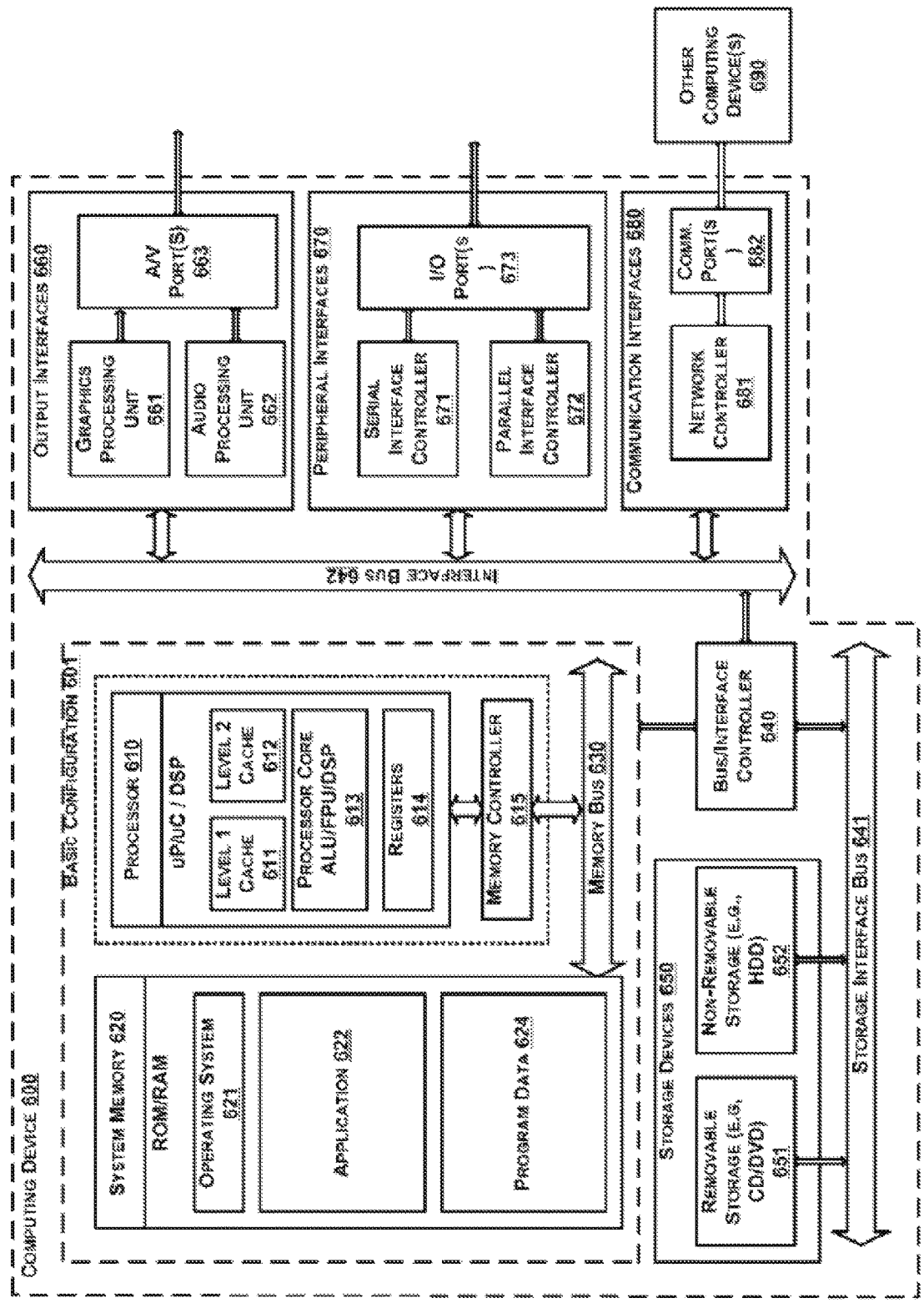
FIG. 21 depicts an illustrative block diagram of an integrated system according to an embodiment.

FIG. 21 depicts an illustrative block diagram of an Hdp monitoring system according to an embodiment. The system includes a computing device 600. The computing device may include various additional components such as basic configuration 601, a bus/interface controller 640, storage devices 650, output devices 660, peripheral devices 670, communication interfaces 680, and/or other computing devices 690. One or more busses may be configured to operably connect the above-identified components. For example, a storage interface bus 641 may be configured to operably connect the storage devices 650 and the bus/interface controller 640. Additionally, an interface bus 642 may be configured to operably connect the bus/interface controller 640 with the output interfaces 660, the peripheral interfaces 670, and/or the communication interfaces 680.

The basic configuration 601 may include a processor 610, a system memory 620, and a memory bus 630 configured to operably connect the processor and the system memory. In some examples, the processor 610 may include a level 1 cache 611, a level 2 cache 612, a processor core 613, one or more registers 614, and a memory controller 615. In some implementations, the system memory 620 may include various software or operating modules such as an operating system 621, one or more applications 622, and program data 624.

In some examples, the storage devices 650 may include a removable storage device 651 including, for example, a USB storage device or other similar removable media. The storage devices 650 may also include a non-removable storage device 652, such as a hard disk drive. In some implementations, the output interfaces 660 may include a graphics processing unit 661, an audio processing unit 662, one or more A/V ports 663 operably connected to the graphics processing unit and the audio processing unit. In some examples, an external output device such as a monitor or other similar display and/or a speaker or other similar audio output device can be operably connected to the A/V ports 663.

In some examples, the peripheral interfaces 670 may include a serial interface controller 671, a parallel interface controller 672, and one or more I/O ports 673 operably connected to the serial interface controller 671 and the parallel interface controller 672. In some examples, an external device such as a printing device may be operably connected to the computing device 600 via the one or more I/O ports 673.

In some implementations, the communication interfaces 680 may include a network controller 681 configured to facilitate communication with other communication devices 690. In some examples, the network controller 681 may be operably connected to one or more communication ports 682 for establishing communication with the other communication devices 690. For example, the communication may be established via a wired or wireless data communication link.

In some implementations, the system as illustrated in FIG. 21 may be configured to measure Hdp values before, during and/or after application of electromagnetic signals to a patient. In an embodiment, circuitry may be provided with a connector configured to connect with the Hdp monitoring system. Alternatively, the circuitry may be integrated into the Hdp monitoring system. Descriptions of each of the blocks of the block diagram or functions thereof are included to facilitate an understanding thereof.

The block diagram of electronic circuitry of the Hdp monitoring system applies an AM EMF to a patient at a predetermined selected amplitude modulated frequency. The predetermined selected frequencies are controlled by AM frequency values stored in the storage device 52 and/or other servers. Various predetermined selected AM frequencies applied to a patient are indicated for treatment of patients suffering from a poor health condition for which the patient has been diagnosed.

In an embodiment, an integrated or combined device may enable sensing of Hdp values and reflection power energy of a patient prior to, during or after application of the AM EMF or other such signals. Of particular interest in this regard is that the measured and recorded Hdp and reflection power energy values may differ based upon the patient condition. For example, measured and recorded Hdp and reflection power energy values may differ among patients suffering from different forms of cancer. In addition, the measured and recorded Hdp and reflection power energy values may differ from patients suffering from a form of cancer and healthy patients. However, such Hdp and reflection power energy values may be substantially similar for patients suffering from the same or a closely related poor health condition. The measured and recorded representative Hdp and reflection power energy variation values and the identification of one or more AM EMFs accordingly offer diagnosis opportunities for various forms of poor health conditions and/or offer prognosis of the quality of life, survival, or hospital admission of a patient. In addition, such Hdp variation values may permit the diagnosis or prognosis of healthy patient conditions.

Referring back to FIG. 20, the microprocessor 21 operates as the controller for the application system and is connected to control the various components of the system through address bus 22, data bus 23 and input/output (I/O) lines 25. Microprocessor 21 preferably includes internal storage for the operation code, control program, and temporary data. In addition, microprocessor 21 includes input/output (I/O) ports and internal timers. Microprocessor 21 may be, for example, an 8-bit single-chip micro controller, such as 8048 or 8051 controllers available from Intel Corporation of Santa Clara, Calif. The timing for the microprocessor 21 is provided by a system clock 24 which includes a clock crystal 26 along with capacitors 27 and 28. The system clock 24 may run at any clock frequency suitable for the particular type of microprocessor used. In accordance with one embodiment, the system clock 24 operates at a clock frequency of 8.0 MHz.

In general, the microprocessor 21 functions to control a controllable electromagnetic energy generator circuit 29 to produce a desired form of the modulated low-energy electromagnetic emission for application to a patient through a probe 13. The controllable generator circuit 29 includes a modulation frequency generator circuit 31 and a carrier signal oscillator 32. The microprocessor 21 operates to activate or de-activate the controllable generator circuit 29 through an oscillator disable line 33. The controllable generator circuit 29 also includes an AM modulator and a power generator 34 which operates to modulate the amplitude of a carrier signal produced by the carrier oscillator 32 on a carrier signal line 36, with a modulation signal produced by the modulation frequency generator circuit 31 on a modulation signal line 37. Modulator 34 produces an amplitude modulated carrier signal on modulated carrier signal line 38, which is then applied to the filter circuit 39. The filter circuit 39 is connected to probe the 13 via a coaxial cable 12 and an impedance transformer 14.

The microprocessor 21 controls the modulation frequency generator circuit 31 of the controllable generator circuit 29 through the address bus 22, the data bus 23 and the I/O lines 25. In particular, the microprocessor 21 selects the desired waveform stored in a modulation waveform storage device 43 via the I/O lines 25. The microprocessor 21 also controls a waveform address generator 41 to produce a sequence of addresses on a waveform address bus 42 which are applied to a modulation signal storage device 43 in order to retrieve the selected modulation signal. The desired modulation signal is retrieved from a waveform look-up table 43 and applied to a modulation signal bus 44 in digital form. The modulation signal bus 44 is applied to a digital to analog converter (DAC) 46 which converts the digital modulation signal into analog form. This analog modulation signal is then applied to a selective filter 47 which, under control of microprocessor 21, filters the analog modulation signal by use of a variable filter network including a resistor 48 and capacitors 49 and 51 in order to smooth the waveform produced by the DAC 46 on the modulation signal line 20.

In the present embodiment, the various modulation signal waveforms are stored in the look-up table 43. In an embodiment, the look-up table 43 may contain up to 8 different modulation signal wave forms, although more or fewer may be stored within the scope of this disclosure. Waveforms which have been successfully employed may include square waveforms or sinusoidal waveforms. Other possible modulation signal waveforms include rectified, sinusoidal, triangular, and combinations of all of the above.

In an embodiment, each modulation signal waveform uses 256 bytes of memory and is retrieved from the look-up table 43 by running through the 256 consecutive addresses. It is noted that each waveform may use more or fewer bytes of memory within the scope of this disclosure as will be apparent to one of ordinary skill in the related art. The frequency of the modulation signal is controlled by how fast the waveform is retrieved from the look-up table 43. In an embodiment, this is accomplished by downloading a control code from the microprocessor 21 into programmable counters contained within the waveform address generator 41. The output of the programmable counters then drives a ripple counter that generates the sequence of addresses on the waveform address bus 42.

The waveform address generator 41 may be a programmable, for example, timer/counter uPD65042C, available from NEC. The modulation signal storage device or the look-up table 43 may be, for example, a 28C16 Electrical Erasable Programmable Read Only Memory (EEPROM) programmed with the desired wave form table. The digital to analog converter 46 may be, for example, a DAC port, such as AD557JN available from Analog Devices, and the selective filter 47 may be, for example, a type 4052 multiplexer available from National Semiconductor or Harris Semiconductor. Additional or alternate components may be used within the scope of this disclosure.

The modulation control information used by the microprocessor 21 to control the operation of the controllable generator circuit 29 may be stored in an application storage device 52 or a variable AM frequency tuning device adapted to load the interface 16 with AM frequencies between high and low frequency levels. The application storage device 52 may be any storage device capable of storing information for later retrieval. The application storage device 52 may be connected to the processing system by the interface 16.

It should be emphasized that although the Figures illustrate the microprocessor 21 as being separate from the application storage device 52, the microprocessor and the application storage device where loaded control programs from the processing system are stored into the programmable generator. The control programs once loaded into the system control the operation of the system as described herein. In this case, the interface 16 would exist between the combination of the microprocessor 21, and the application storage device 52 and the rest of the system.

The interface 16 is configured as appropriate for the particular application storage device 52 in use. The interface 16 translates the control information stored in the application storage device 52 into a usable form for storage within the memory of the microprocessor 21 to enable the microprocessor to control the controllable generator circuit 29 to produce the desired modulated low-energy emission. The interface 16 may directly read information stored on the application storage device 52, or it may read information through a communication link with the processing system. When the application storage device 52 and microprocessor 21 are incorporated in the same device, the interface 16 is configured to connect the microprocessor to the rest of the system.

The control information stored in the application storage device 52 specifies various controllable parameters for the modulated low-energy RF electromagnetic emission which is applied to a patient through the probe 13. Such controllable parameters include, for example, the amplitude and frequency of the carrier, the amplitudes and frequencies of the modulation of the carrier, the duration of the emission, the power level of the emission, the duty cycle of the emission (i.e., the ratio of on time to off time of pulsed emissions applied during an application), the sequence of application of different modulation frequencies for a particular application, and the total number of treatments and duration of each treatment prescribed for a particular patient.

For example, the carrier signal and modulation signal may be selected to drive the probe 13 with an amplitude modulated signal in which the carrier signal includes spectral frequency components below 1 GHz, preferably between 1 MHz and 900 MHz, and in which the modulation signal comprises spectral frequency components between about 0.1 Hz and about 10 MHz, between about 1 Hz and about 150 KHz, between about 0.01 Hz and about 1,000 Hz, or between about 0.01 Hz and about 2,000 Hz. In an embodiment, one or more modulation frequencies may be sequenced to form the modulation signal.

As an additional feature, an electromagnetic emission sensor 53 may be provided to detect the presence of electromagnetic emissions at the frequency of the carrier oscillator 32. The emission sensor 53 may provide an indication of whether or not electromagnetic emissions at the desired frequency are present to the microprocessor 21. In response, the microprocessor 21 may perform an action, such as displaying an error message on the information output display 17, disabling the controllable generator circuit 29, or the like.

The system may further include a power sensor 54, which detects the amount of power applied to the patient through the probe 13 as compared with the amount of power returned or reflected from the patient. This forward/reflected power ratio may be indicative of the proper use of the system during a therapeutic session. The power sensor 54 applies an indication of the amount of power applied to patient through the probe 13 relative to the amount of power reflected from the patient to the microprocessor 21 through the power sense line 56.

The indication provided on the power sense line 56 may be digitized and used by the microprocessor 21, for example, to detect and control a level of applied power, and/or to record information related to the actual treatments applied on the application storage device 52. Data transfered to the processing system may include, for example: the number of applications for a given time period; the actual time and date of each treatment; the number of attempted applications; the application compliance (i.e., whether the probe 13 was in place or not in place during the application session); and the cumulative dose of a particular modulation frequency.

The level of power applied is preferably controlled to cause the specific absorption rate (SAR) of energy absorbed by the patient to be from 1 µW/kg of tissue to 50 W/kg of tissue. Preferably, the power level is controlled to cause a SAR of from 100 µW/kg of tissue to 10 W/kg of tissue. Most preferably, the power level is controlled to deliver whole body mean SAR in the range of only 0.2 to 1 mW/kg, with a 1 g peak spatial SAR between 150 and 350 mW/kg. These SARs may be in any tissue of the patient. The system also includes powering circuitry including a battery and charger circuit 57 and a battery voltage change detector 58.

In certain applications of the systems and techniques described herein, application of a specific frequency signal or set of frequencies can be beneficial in both providing a prognostic and predictive benefit for a patient and providing a treatment to the patient. For example, when treating particular types of cancer such as HCC, application of a series of AM EMF that occur every 3 Hz or 10 Hz in a range from about 0.01 Hz to about 20 KHz, or in a range from about 0.01 Hz to about 2 KHz, can be therapeutic in nature and provide prognostic and predictive information (e.g., by measuring patient HRV response to application of the frequencies). Additional information can be measured such as an amount of energy absorbed by the patient, an amount of energy reflected by the patient, and the like.

As noted above, in order to administer the selected frequencies to a patient, a carrier signal can be used. For example, an oscillator 302 can be configured to produce a carrier signal having a specific frequency, such as 27.12 MHz. However, by modulating the amplitude of the carrier wave, a modulated signal can be produced at, for example, a series of electromagnetic frequencies that occur every 1 Hz, 3 Hz or 10 Hz in a range from about 0.01 Hz to about 20 KHz, in a range from about 10 Hz to about 1,000 Hz, or in a range from about 10 Hz to about 2,000 Hz. In some embodiments, a modulated signal can be produced at a series of electromagnetic frequencies that occur every 1 Hz in a range from about 0.01 Hz to about 20 KHz. In some embodiments, a modulated signal can be produced at a series of electromagnetic frequencies that occur every 3 Hz in a range from about 10 Hz to about 1,000 Hz, or in a range from about 10 Hz to about 2,000 Hz. In some embodiments, a modulated signal can be produced at a series of electromagnetic frequencies that occur every 10 Hz in a range from about 0.01 Hz to about 20 KHz. In some embodiments, a modulated signal can be produced at a series of electromagnetic frequencies that occur every 10 Hz in a range from about 10 Hz to about 1,000 Hz, or in a range from about 10 Hz to about 2,000 Hz. In some embodiments, a modulated signal can be produced at a series of electromagnetic frequencies as illustrated in Table 1 below.

TABLE 1

(in Hz)

| | | | | | | | | | | | | | | | |
|---|---|---|---|---|---|---|---|---|---|---|---|---|---|---|---|
| 10 | 76 | 142 | 208 | 274 | 340 | 406 | 472 | 538 | 604 | 670 | 736 | 802 | 868 | 934 | 1000 |
| 13 | 79 | 145 | 211 | 277 | 343 | 409 | 475 | 541 | 607 | 673 | 739 | 805 | 871 | 937 | |
| 16 | 82 | 148 | 214 | 280 | 346 | 412 | 478 | 544 | 610 | 676 | 742 | 808 | 874 | 940 | |
| 19 | 85 | 151 | 217 | 283 | 349 | 415 | 481 | 547 | 613 | 679 | 745 | 811 | 877 | 943 | |
| 22 | 88 | 154 | 220 | 286 | 352 | 418 | 484 | 550 | 616 | 682 | 748 | 814 | 880 | 946 | |
| 25 | 91 | 157 | 223 | 289 | 355 | 421 | 487 | 553 | 619 | 685 | 751 | 817 | 883 | 949 | |
| 28 | 94 | 160 | 226 | 292 | 358 | 424 | 490 | 556 | 622 | 688 | 754 | 820 | 886 | 952 | |
| 31 | 97 | 163 | 229 | 295 | 361 | 427 | 493 | 559 | 625 | 691 | 757 | 823 | 889 | 955 | |
| 34 | 100 | 166 | 232 | 298 | 364 | 430 | 496 | 562 | 628 | 694 | 760 | 826 | 892 | 958 | |
| 37 | 103 | 169 | 235 | 301 | 367 | 433 | 499 | 565 | 631 | 697 | 763 | 829 | 895 | 961 | |
| 40 | 106 | 172 | 238 | 304 | 370 | 436 | 502 | 568 | 634 | 700 | 766 | 832 | 898 | 964 | |
| 43 | 109 | 175 | 241 | 307 | 373 | 439 | 505 | 571 | 637 | 703 | 769 | 835 | 901 | 967 | |
| 46 | 112 | 178 | 244 | 310 | 376 | 442 | 508 | 574 | 640 | 706 | 772 | 838 | 904 | 970 | |
| 49 | 115 | 181 | 247 | 313 | 379 | 445 | 511 | 577 | 643 | 709 | 775 | 841 | 907 | 973 | |
| 52 | 118 | 184 | 250 | 316 | 382 | 448 | 514 | 580 | 646 | 712 | 778 | 844 | 910 | 976 | |
| 55 | 121 | 187 | 253 | 319 | 385 | 451 | 517 | 583 | 649 | 715 | 781 | 847 | 913 | 979 | |
| 58 | 124 | 190 | 256 | 322 | 388 | 454 | 520 | 586 | 652 | 718 | 784 | 850 | 916 | 982 | |
| 61 | 127 | 193 | 259 | 325 | 391 | 457 | 523 | 589 | 655 | 721 | 787 | 853 | 919 | 985 | |
| 64 | 130 | 196 | 262 | 328 | 394 | 460 | 526 | 592 | 658 | 724 | 790 | 856 | 922 | 988 | |
| 67 | 133 | 199 | 265 | 331 | 397 | 463 | 529 | 595 | 661 | 727 | 793 | 859 | 925 | 991 | |
| 70 | 136 | 202 | 268 | 334 | 400 | 466 | 532 | 598 | 664 | 730 | 796 | 862 | 928 | 994 | |
| 73 | 139 | 205 | 271 | 337 | 403 | 469 | 535 | 601 | 667 | 733 | 799 | 865 | 931 | 997 | |

Figure 19:
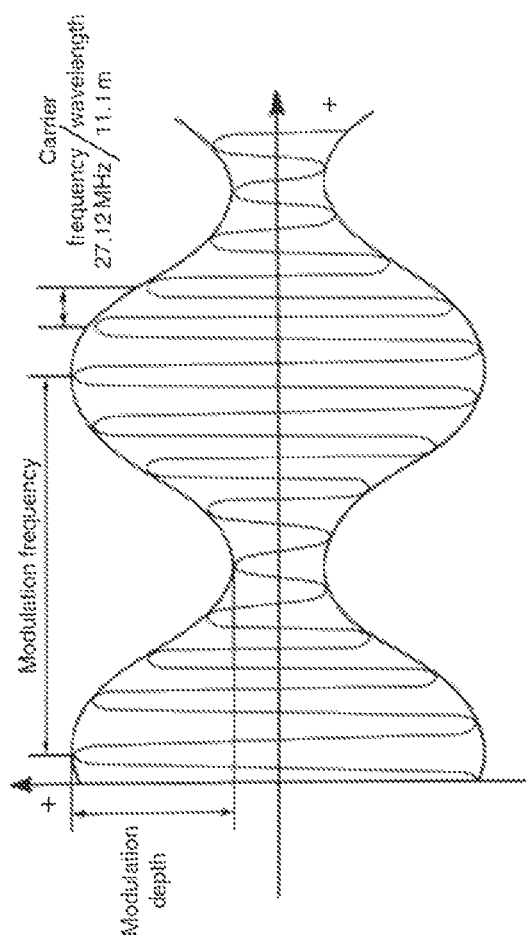
FIG. 19 illustrates an amplitude modulation (AM) radio frequency (RF) electromagnetic field (EMF) according to various embodiments.

In certain implementations, a signal, such as the signal shown in FIG. 19, may be representative of an AM EMF signal produced by modulating the amplitude of the carrier signal. As shown in FIG. 19, by modulating the amplitude of the signal, varying modulation depths can be achieved, thereby producing a modulated signal having a specific modulation frequency. However, as further shown in FIG. 19, during the amplitude modulation, the frequency of the carrier signal remains unchanged, e.g., 27.12 MHz in this example.

For the precise measurement of HRV, in order to identify a biological surrogate in humans, a highly precise and integrated system may be capable of identifying signals in time-domain non-linear systems in very short period intervals. For example, a Hdp monitoring system, such as system 900 in FIG. 16B, can synchronize a monitoring device 902, a RF generator 904, a database 908 configured to store a dynamic data library for hemodynamic recording and data processing in a precise, reliable and reproducible way, and a computing device 910 configured to store and execute statistical computing algorithms and processing techniques.

In certain implementations, a program orchestrator 906 can be configured to control the monitor 902 and the frequency generator 904 and to send intervention signals to the monitor for every new frequency modulation exposure for posterior data synchronization. Data filtering, data synchronization, data processing for calculation of time-domain parameters and data transformation may all be performed automatically following strict computing processes and using the techniques and processes as described below.

Figure 17:
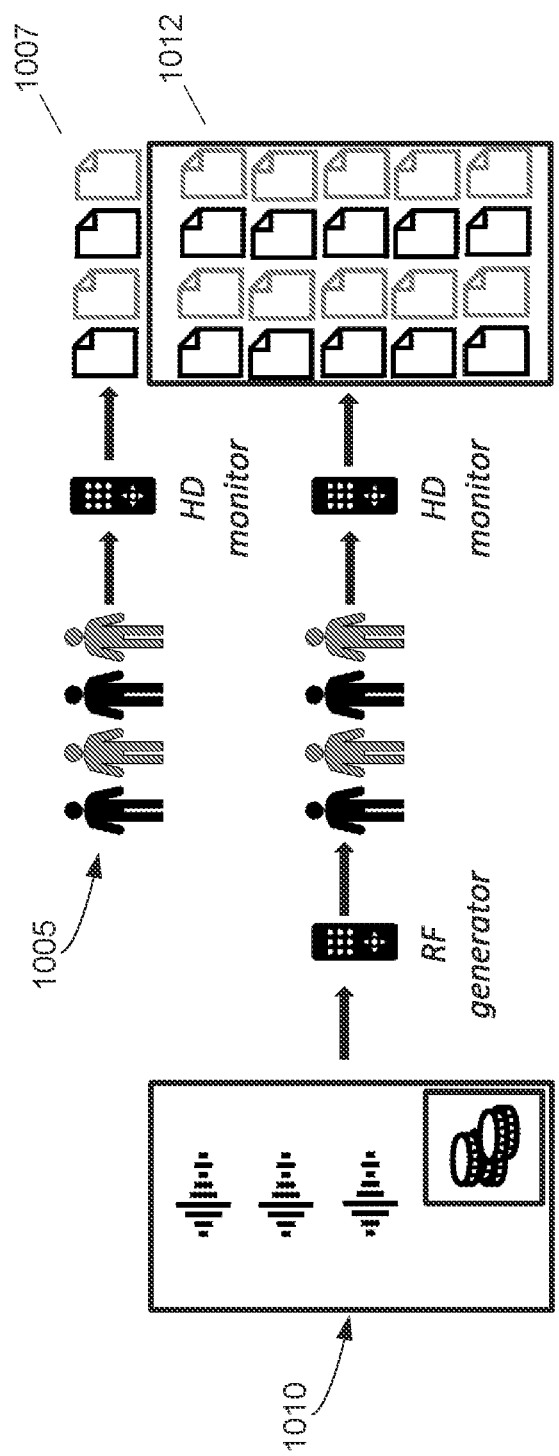
FIG. 17 illustrates a flow diagram for a signal modulator in accordance with an embodiment.

In order to collect data to train and improve the statistical algorithms 910 as described herein, initial patient data can be collected to train the initial computational statistics algorithms (explained in greater detail below in the discussion of FIG. 22). For example, FIG. 17 illustrates two data flows that can represent data collection for a set of patients. An initial flow 1005 includes collecting conventional treatment information for a set of patients. These patients may be diagnosed as healthy or having one or more ailments or diseases, such as HCC. The patients' hemodynamic parameters can be monitored and collected into an initial data set 1007.

Similar, a second data flow 1010 can include collecting data for patients using electromagnetic exposure as well. For example, a set of specific frequencies can be determined (or a standard set of frequencies can be used). A RF generator can produce those frequencies and expose a set of patients to the frequencies. A hemodynamic monitor can measure the patients' hemodynamic response to the exposure and collect and record that data as data set 1012.

Figure 18:
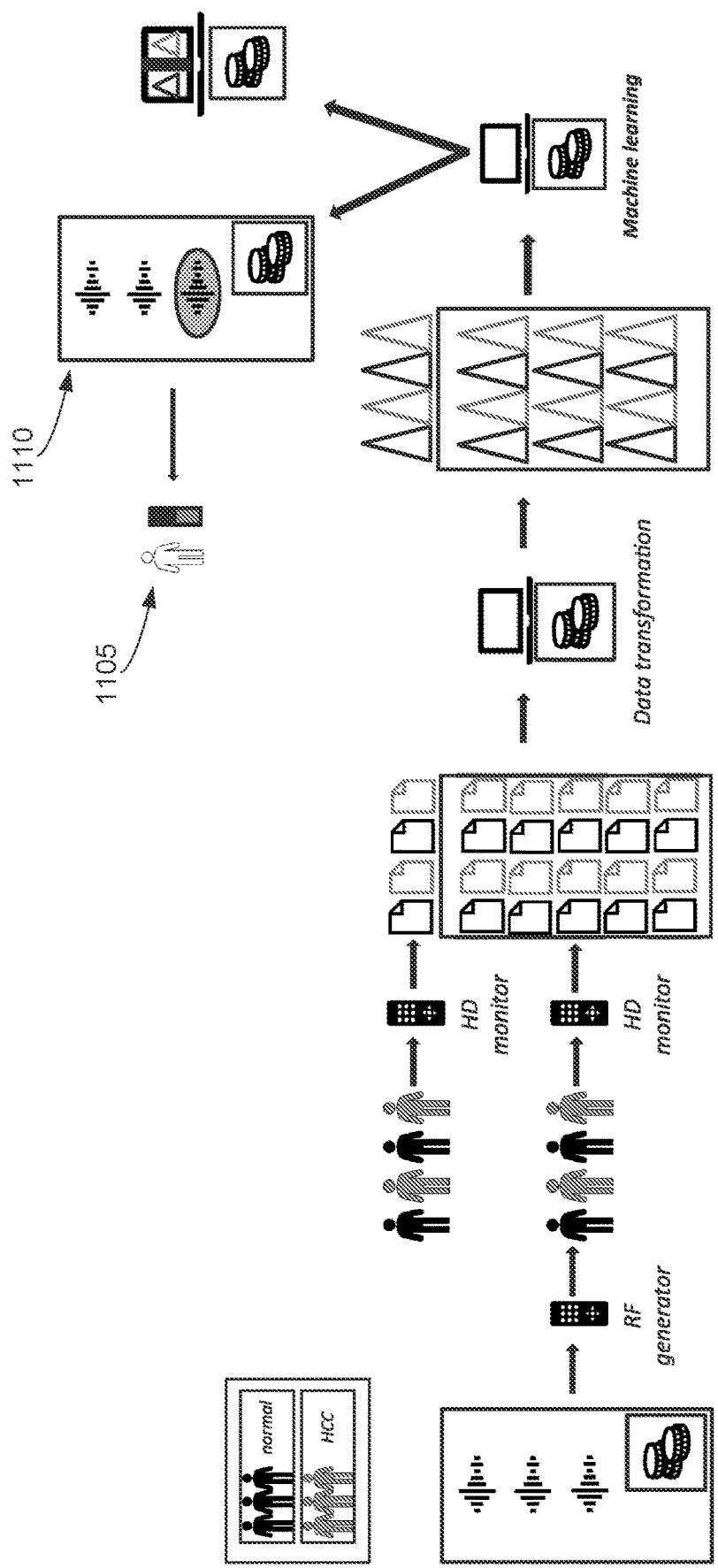
FIG. 18 illustrates a flow diagram for a signal modulator in accordance with an alternate embodiment.

In certain implementations, the processes and techniques as described in FIG. 17 can be used to tune a treatment to a specific patient. For example, as shown in FIG. 18, a specialized or tuned treatment for patient 1105 can be determined or calculated automatically based upon the records collected for other patients, initial test results for the patient 1105, and statistical techniques. For example, as shown in FIG. 18, patient records can be collected as described above in the discussion of FIG. 17. The patient records can then be analyzed and further processed to transform the records into a data format configured to be input into one or more computational statistics algorithms. The output of the computational statistics algorithms can then be further analyzed and compared to the specific patient's 1105 information (e.g., demographic information, prior test results, initial energy exposure information) to determine a diagnosis or prognosis of the quality of life, survival, or hospital admission of a patient. In certain implementations, the diagnosis or prognosis regimen can include an auto-tuned set 1110 of frequencies or energy levels for use during exposure of the patient 1105 to the electromagnetic energy as described herein.

As shown in FIGS. 23A-D, various timelines can be implemented for exposure of a patient to a set of modulated frequency signals. As shown in FIGS. 23A-D, the patient can be relaxed in a supine position. An initial period of about ten minutes of non-exposure can be included to allow for the patient to relax and establish baselines for various hemodynamic parameters and HRV. After the initial non-exposure period, the patient may be exposed to the carrier signal (i.e., at a constant amplitude without amplitude modulation) for about a ten-minute period. After the initial exposure period, the patient may be exposed to a modulated frequency for about 120 minutes, about 60 minutes, about 35 minutes, or about 10 minutes. During this time, each of the set of frequencies (e.g., a series of electromagnetic frequencies that occur every 1 Hz, 3 Hz or 10 Hz in a range from about 0.01 Hz to about 20 KHz, in a range from about 10 Hz to about 1,000 Hz, or in a range from about 10 Hz to about 2,000 Hz as described herein) can be applied to the patient for a particular period of time. In some embodiments, the series of electromagnetic frequencies in a range from about 0.01 Hz to about 20 KHz, from about 10 Hz to about 1,000 Hz, or from about 10 Hz to about 2,000 Hz can occur about every 3 Hz. In some embodiments, the series of electromagnetic frequencies in a range from about 0.01 Hz to about 20 KHz, from about 10 Hz to about 1,000 Hz, or from about 10 Hz to about 2,000 Hz can occur about every 4 Hz. In some embodiments, the series of electromagnetic frequencies in a range from about 0.01 Hz to about 20 KHz, from about 10 Hz to about 1,000 Hz, or from about 10 Hz to about 2,000 Hz can occur about every 5 Hz. In some embodiments, the series of electromagnetic frequencies in a range from about 0.01 Hz to about 20 KHz, from about 10 Hz to about 1,000 Hz, or from about 10 Hz to about 2,000 Hz can occur about every 6 Hz. In some embodiments, the series of electromagnetic frequencies in a range from about 0.01 Hz to about 20 KHz, from about 10 Hz to about 1,000 Hz, or from about 10 Hz to about 2,000 Hz can occur about every 7 Hz. In some embodiments, the series of electromagnetic frequencies in a range from about 0.01 Hz to about 20 KHz, from about 10 Hz to about 1,000 Hz, or from about 10 Hz to about 2,000 Hz can occur about every 8 Hz. In some embodiments, the series of electromagnetic frequencies in a range from about 0.01 Hz to about 20 KHz, from about 10 Hz to about 1,000 Hz, or from about 10 Hz to about 2,000 Hz can occur about every 9 Hz. In some embodiments, the series of electromagnetic frequencies in a range from about 0.01 Hz to about 20 KHz, from about 10 Hz to about 1,000 Hz, or from about 10 Hz to about 2,000 Hz can occur about every 10 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 3 Hz to about every 10 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 4 Hz to about every 10 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 5 Hz to about every 10 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 6 Hz to about every 10 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 7 Hz to about every 10 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 8 Hz to about every 10 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 9 Hz to about every 10 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 3 Hz to about every 9 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 3 Hz to about every 8 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 3 Hz to about every 7 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 3 Hz to about every 6 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 3 Hz to about every 5 Hz. In some embodiments, the series of electromagnetic frequencies in a range from about 0.01 Hz to about 20 KHz, from about 10 Hz to about 1,000 Hz, or from about 10 Hz to about 2,000 Hz can occur in a range from about every 3 Hz to about every 4 Hz. In some embodiments, the particular period of time is about 2 or about 3 seconds per frequency. In some embodiments, the particular period of time is about 2 seconds per frequency. In some embodiments, the particular period of time is about 3 seconds per frequency. In some embodiments, the particular period of time is about 4 seconds per frequency. In some embodiments, the particular period of time is about 5 seconds per frequency. In some embodiments, the particular period of time is about 6 seconds per frequency. In some embodiments, the particular period of time is about 7 seconds per frequency. In some embodiments, the particular period of time is about 8 seconds per frequency. In some embodiments, the particular period of time is about 9 seconds per frequency. In some embodiments, the particular period of time is about 10 seconds per frequency.

Figure 23A:
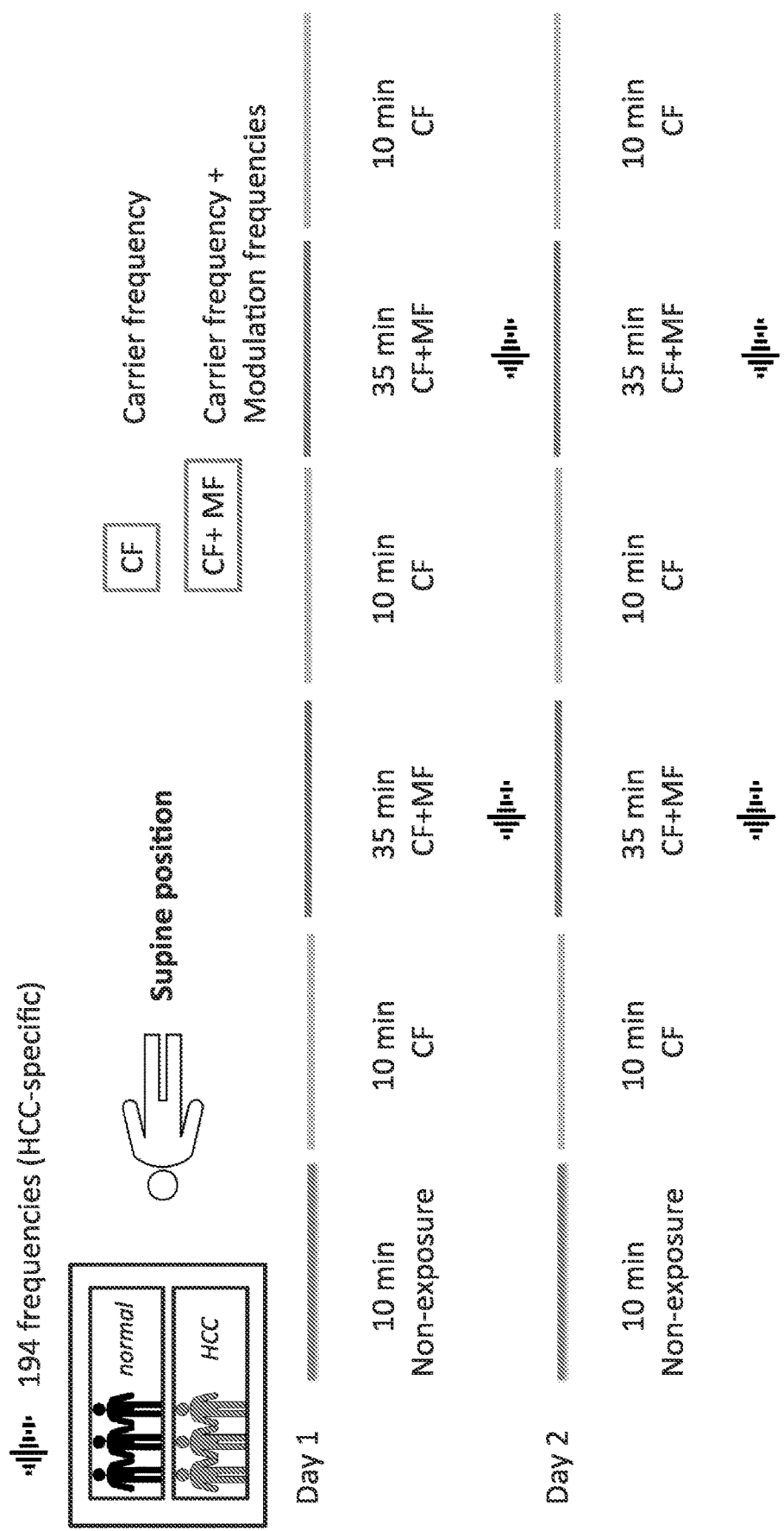
FIG. 23A illustrates a diagram representing a signal exposure protocol over the course of one or two days in accordance with an embodiment.
Figure 23B:
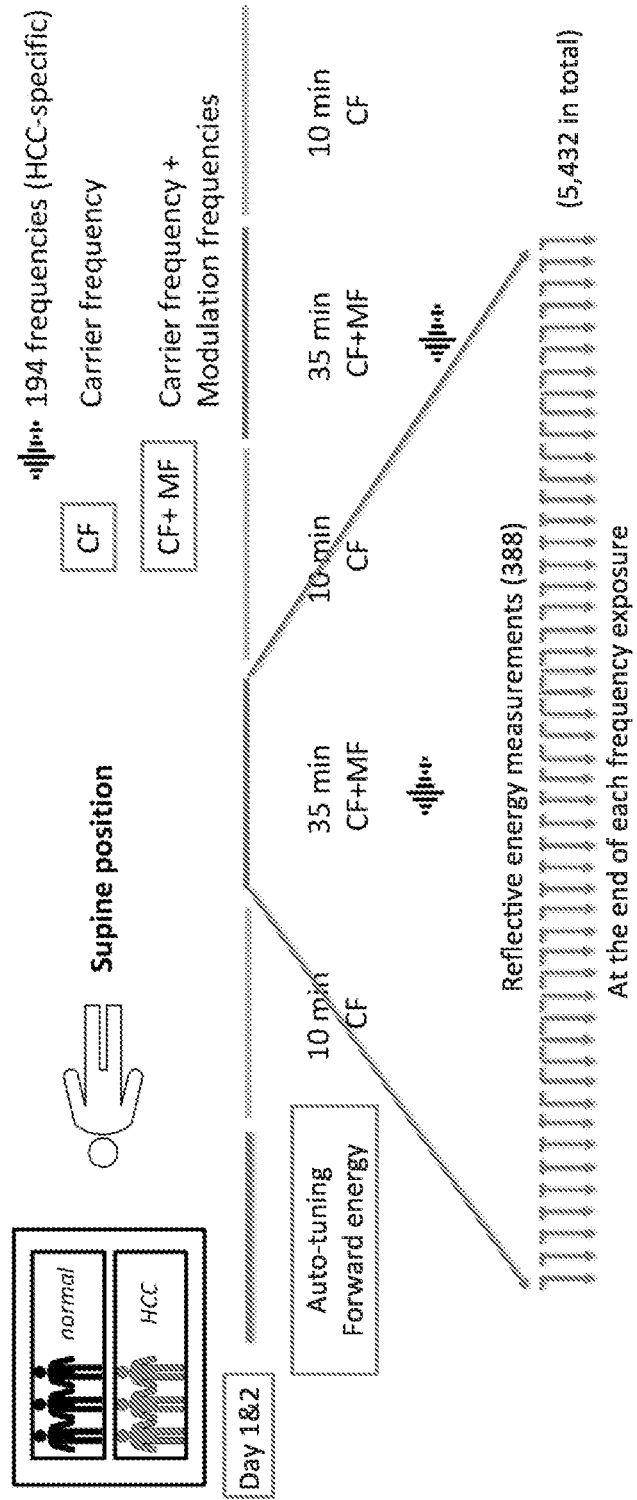
FIG. 23B illustrates a diagram representing a signal exposure protocol with reflective energy measurements over the course of one or two days.
Figure 23C:
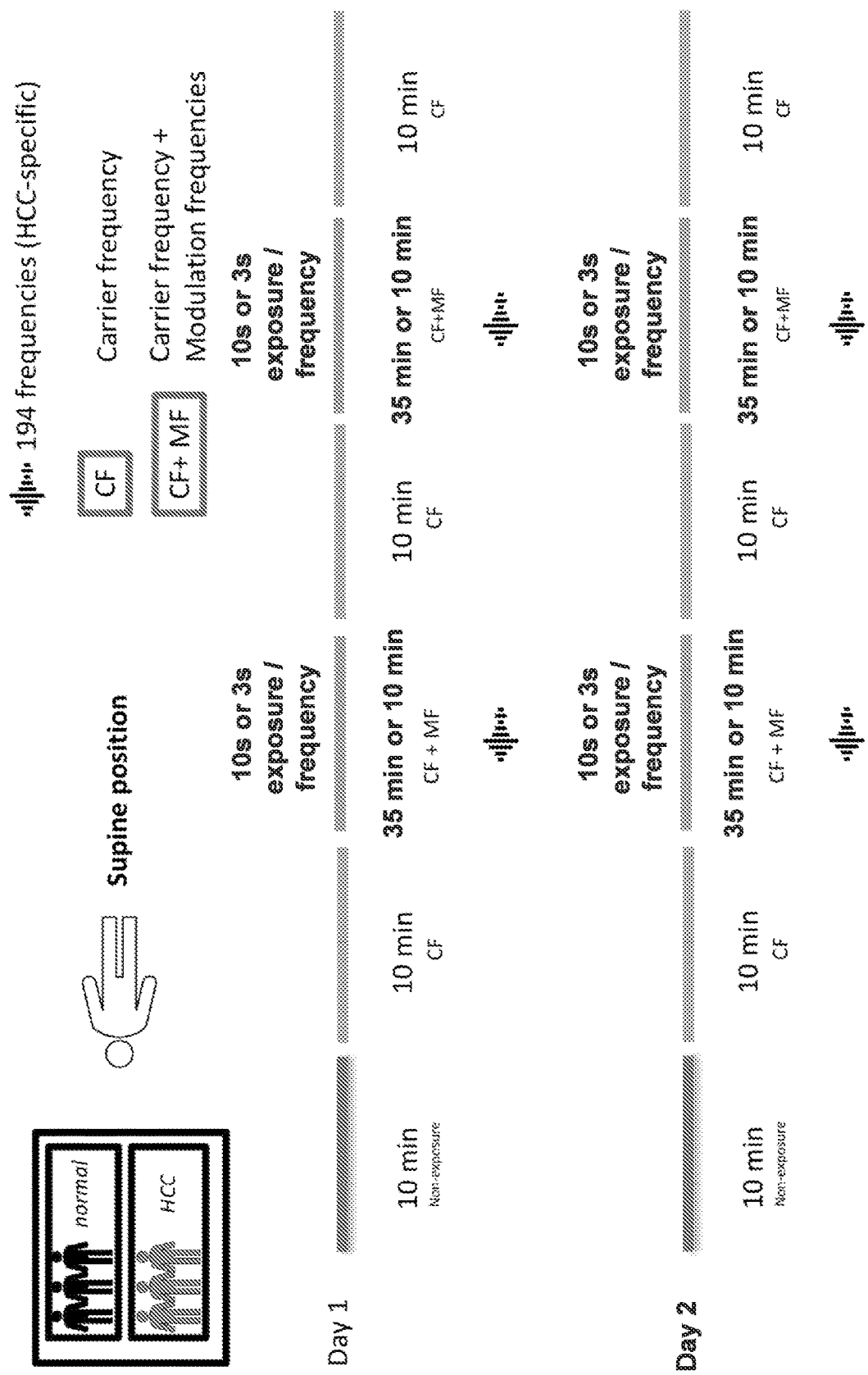
FIG. 23C illustrates a diagram representing a signal exposure protocol over the course of one or two days in accordance with an embodiment.
Figure 23D:
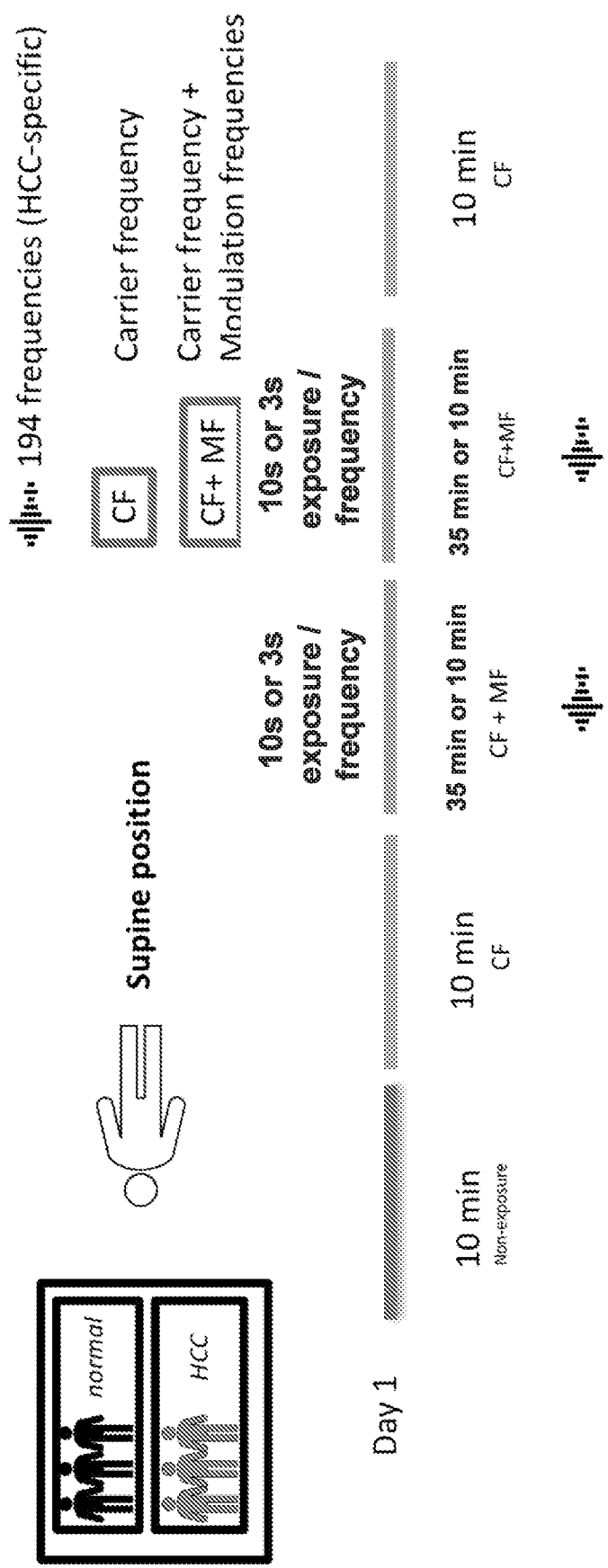
FIG. 23D illustrates a diagram representing a signal exposure protocol over the course of one day in accordance with an embodiment.
Figure 23E:
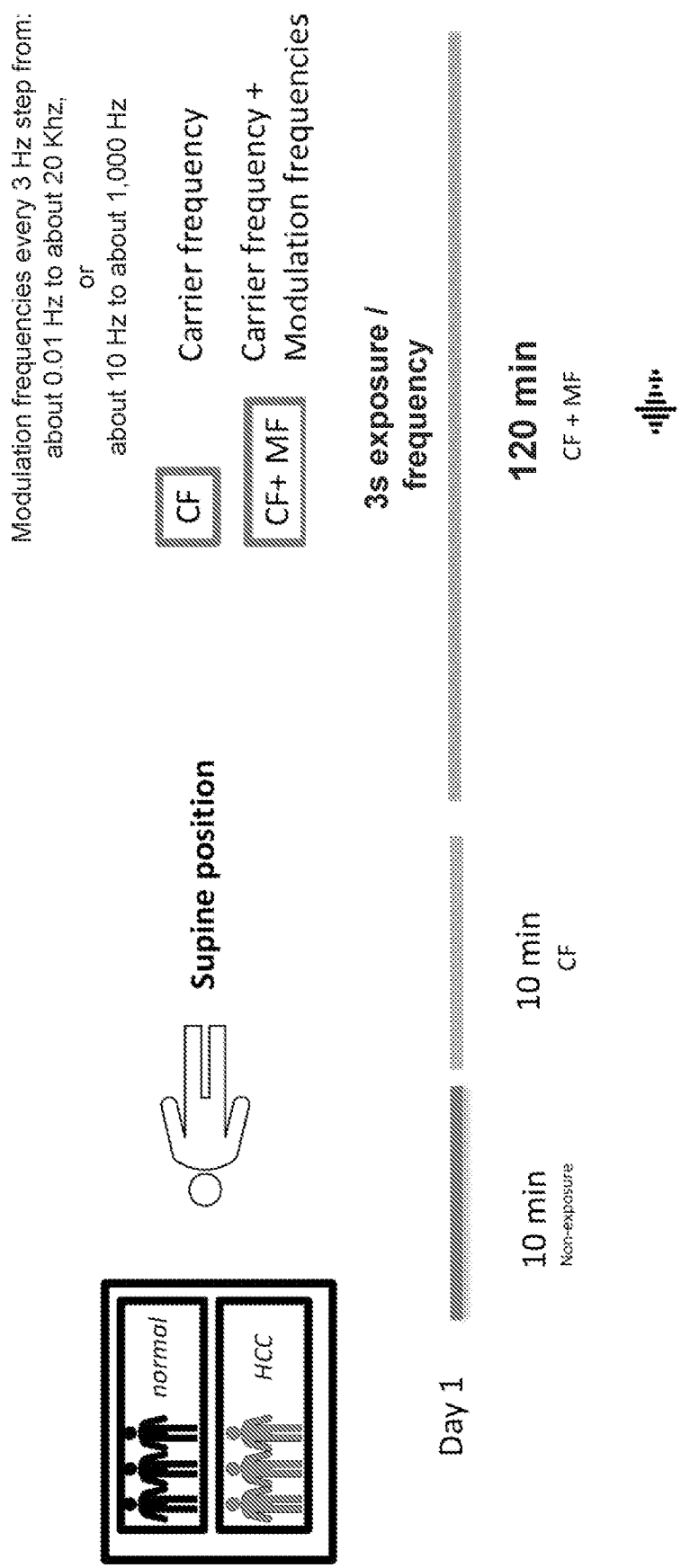
FIG. 23E illustrates a diagram representing a signal exposure protocol over the course of one day in accordance with an additional embodiment.

In some embodiments, the modulated frequencies applied to the patient can be a series of electromagnetic frequencies that occur every 3 Hz in a range from about 0.01 Hz to about 20 KHz. In some embodiments, the modulated frequencies applied to the patient can be a series of electromagnetic frequencies that occur every 3 Hz in a range from about 10 Hz to about 1,000 Hz. In some embodiments, the modulated frequencies applied to the patient can be a series of electromagnetic frequencies that occur every 3 Hz in a range from about 10 Hz to about 2,000 Hz. In some embodiments, the modulated frequencies applied to the patient can be a series of electromagnetic frequencies that occur every 10 Hz in a range from about 0.01 Hz to about 20 KHz. In some embodiments, the modulated frequencies applied to the patient can be a series of electromagnetic frequencies that occur every 10 Hz in a range from about 10 Hz to about 1,000 Hz. In some embodiments, the modulated frequencies applied to the patient can be a series of electromagnetic frequencies that occur every 10 Hz in a range from about 10 Hz to about 2,000 Hz. The system can cycle repeatedly through each of the frequencies for the exposure period. In some embodiments, an exposure period may be about 35 minutes (FIGS. 23A-D). In further embodiments, an exposure period may be about 10 minutes (FIGS. 23C and 23D). In some embodiments, an exposure period may be about 120 minutes or about 60 minutes. After the initial exposure period, the system may expose the patient to another carrier signal period for about 10 minutes during which the patient's body can recover from the initial exposure period of about 120 minutes, about 60 minutes, about 35 minutes, or about 10 minutes (FIGS. 23A-C). At the conclusion of the second carrier signal period of about ten minutes, the patient may again be exposed to a second modulated frequency signal period of about 120 minutes, about 60 minutes, about 35 minutes, or about 10 minutes (FIGS. 23A-C). Like before, during this time, each of the set of frequencies (e.g., a series of electromagnetic frequencies that occur every 1 Hz, 3 Hz or 10 Hz in a range from about 0.01 Hz to about 20 KHz, from about 10 Hz to about 1,000 Hz, or from about 10 Hz to about 2,000 Hz as described herein) can be applied to the patient for a particular period of time (e.g., from about 2 seconds to about 3 seconds per frequency, or about 10 seconds per frequency). The system can cycle repeatedly through each of the frequencies for the exposure period, where the exposure period can be about 120 minutes, about 60 minutes, about 35 minutes, or be about 10 minutes. In some embodiments, the modulated frequencies applied to the patient can be a series of electromagnetic frequencies that occur every 3 Hz in a range from about 0.01 Hz to about 20 KHz. In some embodiments, the modulated frequencies applied to the patient can be a series of electromagnetic frequencies that occur every 3 Hz in a range from about 10 Hz to about 1,000 Hz. In some embodiments, the modulated frequencies applied to the patient can be a series of electromagnetic frequencies that occur every 3 Hz in a range from about 10 Hz to about 2,000 Hz. In some embodiments, the modulated frequencies applied to the patient can be a series of electromagnetic frequencies that occur every 10 Hz in a range from about 0.01 Hz to about 20 KHz. In some embodiments, the modulated frequencies applied to the patient can be a series of electromagnetic frequencies that occur every 10 Hz in a range from about 10 Hz to about 1,000 Hz. In some embodiments, the modulated frequencies applied to the patient can be a series of electromagnetic frequencies that occur every 10 Hz in a range from about 10 Hz to about 2,000 Hz. Following this second exposure period, the patient may again be exposed to the carrier frequency for about ten minutes, after which the treatment session is concluded.

The treatment timelines described above may comprise an exposure session. As shown in FIGS. 23A and 23C, the exposure session can be repeated for a patient on a second day. The exposure session can occur for one or more consecutive or non-consecutive days. In some embodiments, the exposure session occurs for one day. In some embodiments, the exposure session occurs for two consecutive days. In some embodiments, the exposure session occurs for two or more non-consecutive days. In some embodiments, the exposure session occurs once per week, twice per week, three times per week, or combinations thereof. In some embodiments, the exposure session occurs 1 time per month, 2 times per month, 3 times per month, 4 times per month, 5 times per month, 6 times per month, 7 times per month, 8 times per month, 9 times per month, 10 times per month, 11 times per month, 12 times per month, 13 times per month, 14 times per month, 15 times per month, 16 times per month, 17 times per month, 18 times per month, 19 times per month, 20 times per month, 21 times per month, 22 times per month, 23 times per month, 24 times per month, 25 times per month, 26 times per month, 27 times per month, 28 times per month, 29 times per month, 30 times per month, or combinations thereof.

In some embodiments, the exposure session occurs for any number of consecutive or non-consecutive days, or any number of monthly treatment sessions for a total of about 1 year, about 2 years, about 3 years, about 4 years, about 5 years, about 6 years, about 7 years, about 8 years, about 9 years, about 10 years, about 11 years, about 12 years, about 13 years, about 14 years, about 15 years, about 16 years, about 17 years, about 18 years, about 19 years, about 20 years, about 21 years, about 22 years, about 23 years, about 24 years, about 25 years, about 26 years, about 27 years, about 28 years, about 29 years, about 30 years, about 31 years, about 32 years, about 33 years, about 34 years, about 35 years, about 36 years, about 37 years, about 38 years, about 39 years, about 40 years, about 41 years, about 42 years, about 43 years, about 44 years, about 45 years, about 46 years, about 47 years, about 48 years, about 49 years, about 50 years, or combinations thereof. In some embodiments, the exposure session occurs for any number of consecutive or non-consecutive days or any number of monthly exposure sessions for a total of about 1 year. In some embodiments, the exposure session occurs for any number of consecutive or non-consecutive days or any number of monthly exposure sessions for a total of about 2 years. In some embodiments, the exposure session occurs for any number of consecutive or non-consecutive days or any number of monthly exposure sessions ve for a total of about 3 years. In some embodiments, the exposure session occurs for any number of consecutive or non-consecutive days or any number of monthly exposure sessions for a total of about 4 years. In some embodiments, the exposure session occurs for any number of consecutive or non-consecutive days or any number of monthly exposure sessions for a total of about 5 years. In some embodiments, the exposure session occurs for any number of consecutive or non-consecutive days or any number of monthly exposure sessions for a total of about 6 years. In some embodiments, the treatment session occurs for any number of consecutive or non-consecutive days or any number of monthly exposure sessions for a total of about 7 years. In some embodiments, the exposure session occurs for any number of consecutive or non-consecutive days or any number of monthly exposure sessions for a total of about 8 years. In some embodiments, the exposure session occurs for any number of consecutive or non-consecutive days or any number of monthly exposure sessions for a total of about 9 years. In some embodiments, the exposure session occurs for any number of consecutive or non-consecutive days or any number of monthly exposure sessions for a total of about 10 years.

It should be noted that the exposure schedules as shown in FIG. 23A-E are provided by way of example only. In certain implementations or patient-specific treatment timelines, various specifics as shown in FIG. 23A-E can be changed or otherwise altered. For example, the number of modulated frequency exposure periods can be changed to less than or more than two. Further, the number of carrier frequency exposure periods can be changed to less than or more than two. Similarly, the length of the carrier frequency and/or modulated frequency exposure periods can be changed. Further, the modulated frequencies can cycle repeatedly through each of the frequencies for one or more exposure periods.

In some embodiments, the patient can be relaxed in a supine position. An initial period of about ten minutes of non-exposure time can be included to allow for the patient to relax and establish baselines for various hemodynamic parameters and HRV. After the initial non-exposure period, the patient may be exposed to a carrier signal (i.e., at a constant amplitude without amplitude modulation) for about ten minutes. After the initial exposure period, the patient may be exposed to a modulated frequency exposure period for about 35 minutes. During this time, each of the set of frequencies (e.g., a series of electromagnetic frequencies that occur every 1 Hz, 3 Hz or 10 Hz in a range from about 0.01 Hz to about 20 KHz, from about 10 Hz to about 1,000 Hz, or from about 10 Hz to about 2,000 Hz as described herein) can be applied to the patient for a particular period of time (e.g., 10 seconds per frequency or 3 seconds per frequency). In some embodiments, the modulated frequencies applied to the patient can be a series of electromagnetic frequencies that occur every 3 Hz in a range from about 0.01 Hz to about 20 KHz. In some embodiments, the modulated frequencies applied to the patient can be a series of electromagnetic frequencies that occur every 3 Hz in a range from about 10 Hz to about 1,000 Hz. In some embodiments, the modulated frequencies applied to the patient can be a series of electromagnetic frequencies that occur every 3 Hz in a range from about 10 Hz to about 2,000 Hz. In some embodiments, the modulated frequencies applied to the patient can be a series of electromagnetic frequencies that occur every 10 Hz in a range from about 0.01 Hz to about 20 KHz. In some embodiments, the modulated frequencies applied to the patient can be a series of electromagnetic frequencies that occur every 10 Hz in a range from about 10 Hz to about 1,000 Hz. In some embodiments, the modulated frequencies applied to the patient can be a series of electromagnetic frequencies that occur every 10 Hz in a range from about 10 Hz to about 2,000 Hz. The system can cycle repeatedly through each of the frequencies for the exposure period. After the initial exposure period, the system may expose the patient to another carrier signal period of about 10 minutes during which the patient's body can recover from the initial exposure period. At the conclusion of the second carrier signal period of about ten minutes, the patient may be exposed to a modulated frequency signal period of about 10 minutes. During this time, each of the set of frequencies (e.g., a series of electromagnetic frequencies that occur every 3 Hz or 10 Hz in a range from about 0.01 Hz to about 20 KHz, from about 10 Hz to about 1,000 Hz, or from about 10 Hz to about 2,000 Hz as described herein) can be applied to the patient for a particular period of time (e.g., 2 or 3 seconds per frequency or 10 seconds per frequency). In some embodiments, the modulated frequencies applied to the patient can be a series of electromagnetic frequencies that occur every 3 Hz in a range from about 0.01 Hz to about 20 KHz. In some embodiments, the modulated frequencies applied to the patient can be a series of electromagnetic frequencies that occur every 3 Hz in a range from about 10 Hz to about 1,000 Hz. In some embodiments, the modulated frequencies applied to the patient can be a series of electromagnetic frequencies that occur every 3 Hz in a range from about 10 Hz to about 2,000 Hz. In some embodiments, the modulated frequencies applied to the patient can be a series of electromagnetic frequencies that occur every 10 Hz in a range from about 0.01 Hz to about 20 KHz. In some embodiments, the modulated frequencies applied to the patient can be a series of electromagnetic frequencies that occur every 10 Hz in a range from about 10 Hz to about 1,000 Hz. In some embodiments, the modulated frequencies applied to the patient can be a series of electromagnetic frequencies that occur every 10 Hz in a range from about 10 Hz to about 2,000 Hz. The system can cycle repeatedly through each of the frequencies for the exposure period. Following this second modulated frequency exposure period, the patient may again be exposed to the carrier frequency for about ten minutes, after which the exposure session is concluded. The same exposure session can be repeated for a patient on a second day. The exposure session can occur for one or more consecutive or non-consecutive days. In some embodiments, the exposure session occurs for one day. In some embodiments, the exposure session occurs for two consecutive days. In some embodiments, the exposure session occurs on two non-consecutive days.

In some embodiments, the patient can be relaxed in a supine position. An initial non-exposure period of about ten minutes can be included to allow for the patient to relax and establish baselines for various hemodynamic parameters and HRV. After the initial non-exposure period, the patient may be exposed to a carrier signal (i.e., at a constant amplitude without amplitude modulation) for about ten minutes. After the initial exposure period, the patient may be exposed to a modulated frequency exposure period of about 50 minutes, about 60 minutes, or about 120 minutes. During this time, the series of electromagnetic frequencies that occur every 3 Hz in a range from about 0.01 Hz to about 20 KHz, from about 10 Hz to about 1,000 Hz, from about 100 Hz to about 1,000 Hz, or from about 10 Hz to about 2,000 Hz can be applied to the patient for about 3 seconds per frequency. The system can cycle repeatedly through each of the frequencies for the exposure period. After this initial exposure period, the system may expose the patient to another carrier signal period for about 10 minutes during which the patient's body can recover from the initial exposure period, after which the exposure session is concluded. The same exposure session can be repeated for a patient on a second day. The exposure session can occur for one or more consecutive or non-consecutive days. In some embodiments, the exposure session occurs for one day. In some embodiments, the exposure session occurs for two consecutive days. In some embodiments, the exposure session occurs for two non-consecutive days.

In some embodiments, the patient can be relaxed in a supine position. An initial non-exposure period of about ten minutes can be included to allow for the patient to relax and establish baselines for various hemodynamic parameters and HRV. After the initial non-exposure period, the patient may be exposed to a carrier signal (i.e., at a constant amplitude without amplitude modulation) for about ten minutes. After the initial exposure period, the patient may be exposed to a modulated frequency exposure period for about 50 minutes, about 60 minutes, or about 120 minutes. During this time, the series of electromagnetic frequencies that occur every 3 Hz in a range from about 0.01 Hz to about 20 KHz, from about 10 Hz to about 1,000 Hz, from about 100 Hz to about 1,000 Hz, from about 10 Hz to about 2,000 Hz can be applied to the patient for about 3 seconds per frequency. The system can cycle repeatedly through each of the frequencies for the exposure period. After this initial exposure period, the system may expose the patient to another carrier signal period for about 10 minutes during which the patient's body can recover from the initial exposure period. In some embodiments, the system can determine if the patient is to be exposed for an additional period to the modulated frequency signal. If the patient is to be exposed for another period, the system may expose the patient to another modulated frequency exposure period. In some embodiments, the additional modulated frequency exposure comprises the modulated frequencies that altered a hemodynamic parameter, for example heart rate variability, in the initial modulated frequency exposure period. In some embodiments, the additional modulated frequency exposure comprises the series of electromagnetic frequencies that occur every 3 Hz or 10 Hz in a range from about 0.01 Hz to about 20 KHz, from about 10 Hz to about 1,000 Hz, or from about 10 Hz to about 2,000 Hz. Following the initial or additional modulated frequency exposure, the system can expose the patient to another carrier wave exposure period for about ten minutes. If the patient is not to be exposed to another modulated frequency period, the process can end. The same exposure session can be repeated for a patient on a second day. The exposure session can occur for one or more consecutive or non-consecutive days. In some embodiments, the exposure session occurs for one day. In some embodiments, the exposure session occurs for two consecutive days. In some embodiments, the exposure session occurs for two or more non-consecutive days.

As illustrated in FIG. 23D, in some embodiments the patient can be relaxed in a supine position. An initial non-exposure period of about ten minutes can be included to allow for the patient to relax and establish baselines for various hemodynamic parameters and HRV. After the initial non-exposure period, the patient may be exposed to a carrier signal (i.e., at a constant amplitude without amplitude modulation) for about ten minutes. After the initial exposure period, the patient may be exposed to a modulated frequency exposure period for about 35 minutes or about 10 minutes. During this time, each of the set of frequencies (e.g., a series of electromagnetic frequencies that occur every 1 Hz, 3 Hz or 10 Hz in a range from about 0.01 Hz to about 20 KHz, from about 10 Hz to about 1,000 Hz, or from about 10 Hz to about 2,000 Hz as described herein) can be applied to the patient for a particular period of time (e.g., about 10 seconds per frequency or about 3 seconds per frequency). In some embodiments, the modulated frequencies applied to the patient can be a series of electromagnetic frequencies that occur every 3 Hz in a range from about 0.01 Hz to about 20 KHz. In some embodiments, the modulated frequencies applied to the patient can be a series of electromagnetic frequencies that occur every 3 Hz in a range from about 10 Hz to about 1,000 Hz. In some embodiments, the modulated frequencies applied to the patient can be a series of electromagnetic frequencies that occur every 3 Hz in a range from about 10 Hz to about 2,000 Hz. In some embodiments, the modulated frequencies applied to the patient can be a series of electromagnetic frequencies that occur every 10 Hz in a range from about 0.01 Hz to about 20 KHz. In some embodiments, the modulated frequencies applied to the patient can be a series of electromagnetic frequencies that occur every 10 Hz in a range from about 10 Hz to about 1,000 Hz. In some embodiments, the modulated frequencies applied to the patient can be a series of electromagnetic frequencies that occur every 10 Hz in a range from about 10 Hz to about 2,000 Hz. The system can cycle repeatedly through each of the frequencies for the exposure period. After the initial exposure period of about 35 minutes or about 10 minutes, the system may expose the patient to another exposure period that comprises the initial modulated frequencies that altered a hemodynamic parameter (e.g., heart rate variability). In some embodiments, after the initial exposure period of about 35 minutes or about 10 minutes, the system may expose the patient to another exposure period that comprises the initial modulated frequencies that did not alter a hemodynamic parameter (e.g., heart rate variability). In some embodiments, after the initial exposure period of about 35 minutes or about 10 minutes, the system may expose the patient to another exposure period that comprises a series of electromagnetic frequencies that occur every 1 Hz, 3 Hz or 10 Hz in a range from about 0.01 Hz to about 20 KHz, from about 10 Hz to about 1,000 Hz, or from about 10 Hz to about 2,000 Hz as described herein. In some embodiments, the modulated frequencies applied to the patient can be a series of electromagnetic frequencies that occur every 3 Hz in a range from about 0.01 Hz to about 20 KHz. In some embodiments, the modulated frequencies applied to the patient can be a series of electromagnetic frequencies that occur every 3 Hz in a range from about 10 Hz to about 1,000 Hz. In some embodiments, the modulated frequencies applied to the patient can be a series of electromagnetic frequencies that occur every 3 Hz in a range from about 10 Hz to about 2,000 Hz. In some embodiments, the modulated frequencies applied to the patient can be a series of electromagnetic frequencies that occur every 10 Hz in a range from about 0.01 Hz to about 20 KHz. In some embodiments, the modulated frequencies applied to the patient can be a series of electromagnetic frequencies that occur every 10 Hz in a range from about 10 Hz to about 1,000 Hz. In some embodiments, the modulated frequencies applied to the patient can be a series of electromagnetic frequencies that occur every 10 Hz in a range from about 10 Hz to about 2,000 Hz. Following this second modulated frequency exposure period, the patient may again be exposed to the carrier frequency for about ten minutes, after which the exposure session is concluded. The same exposure session can be repeated for a patient on a second day. The exposure session can occur for one or more consecutive or non-consecutive days. In some embodiments, the exposure session occurs for one day. In some embodiments, the exposure session occurs for two or more consecutive days. In some embodiments, the exposure session occurs for two or more non-consecutive days.

As noted above, for a specific patient the treatment can be customized or auto-tuned such that the forward energy (e.g., energy used in the carrier and modulated frequency signals) is chosen specifically for a particular patient. This auto-tuning can be determined for a particular patient based upon various factors such as patient information (e.g., health condition, size and weight, prior treatment information) such that the forward energy applied to the patient during treatment, and the energy absorbed by the patient's cells during treatment, is within a specific range or threshold of the normal or average energy values for similar other patients. As shown in FIG. 23B, this auto-tuning can be performed prior to the initial carrier frequency period.

Additionally, as shown in FIG. 23B, during the modulated frequency exposure period, reflective energy can be measured as well. Reflective energy provides an indication of how much of the forward energy is not being absorbed or transmitted through the patient. As transmission energy is generally constant for a patient, the transmission energy can be considered to be negligible for a patient during treatment. Thus, by measuring the reflective energy, the system can approximate the amount of energy being absorbed by the patient during the exposure periods.

Figure 24:
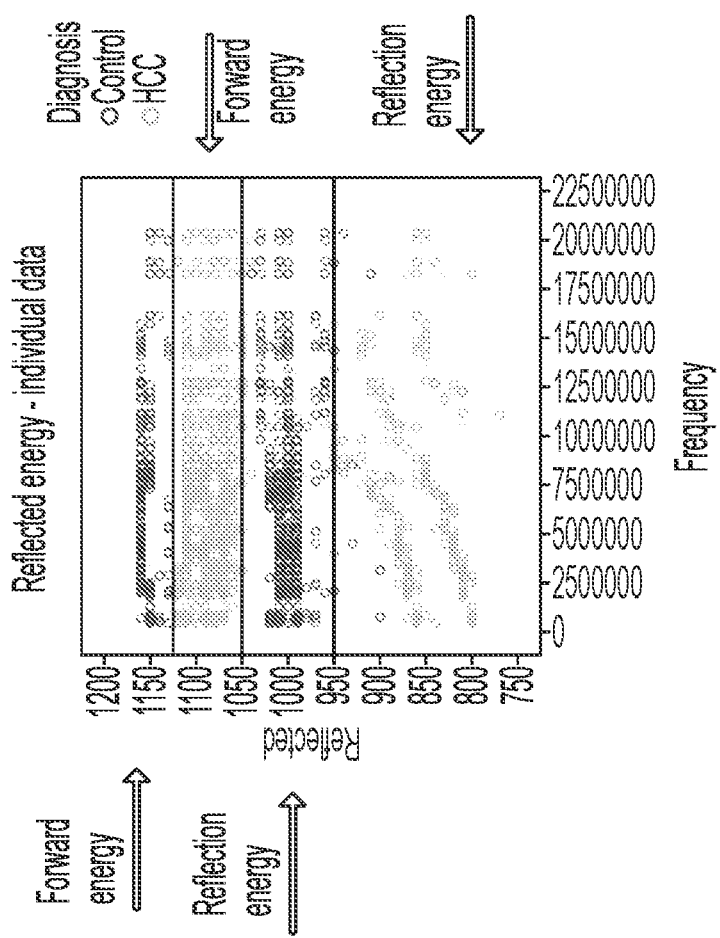
FIG. 24 illustrates reflection energy differences in accordance with some embodiments.

Additionally, by measuring reflective energy, the system can also determine an alternative data point for use in evaluation, diagnosis, or prognosis of a particular ailment or disease. For example, in related studies done during the development of the processes and techniques as described herein, the data in FIG. 24 was observed. As shown in FIG. 24, by measuring and plotting forward energy versus reflective energy for a patient population, various bands of energy levels can be seen. Additionally, for hepatocellular patients, the reflective energy falls into a band generally below the band of reflective energy for healthy patients. Such an occurrence can be used as another factor when determining whether a patient is to be (or likely to be) diagnosed with HCC. Additionally, because the reflective energy levels are lower for HCC patients, this may indicate that HCC patients are absorbing more energy on a cellular level than healthy patients, thus possibly providing at least a portion of an explanation for why modulated frequency exposure as described herein causes cellular malfunction in cancer cells.

Figure 25:
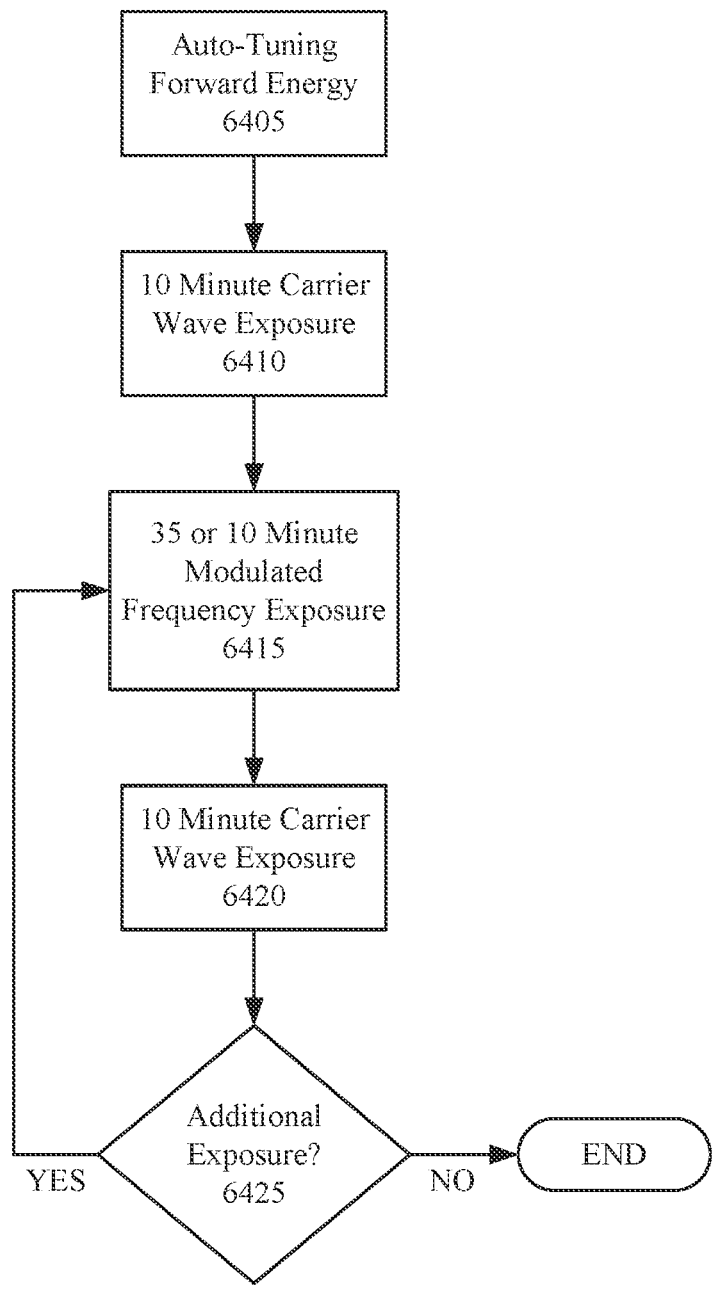
FIG. 25 illustrates a sample process flow for treating a patient according to an embodiment.

As noted above, FIGS. 23A-23E illustrate various treatment timelines for patient treatment. These timelines are also summarized in the process flow as shown in FIG. 25. As shown in FIG. 25, the system (e.g., the orchestrator 906 as shown in FIG. 16B) can initially auto-tune 6405 the forward energy for a specific patient. Following auto-tuning, the system can expose 6410 the patient to the initial about ten-minute carrier wave signal. Following the initial exposure, the system can expose 6415 the patient to the initial modulated frequency signal for about 120 minutes, about 60 minutes, about 35 minutes, or about 10 minutes as described herein. Following the initial modulated frequency exposure, the system can expose 6420 the patient to another carrier wave exposure period for about ten minutes. The system can then determine 6425 whether the patient is to be exposed to the modulated frequency signal for an additional period. If the patient is to be exposed for another period, the process can return to step 6415 where the system exposes the patient to another modulated frequency exposure period for about 120 minutes, about 60 minutes, about 35 minutes, or about 10 minutes. If the patient is not to be exposed to another modulated frequency period, the process ends.

In some embodiments, the system can initially auto-tune 6405 the forward energy for a specific patient. Following auto-tuning, the system can expose 6410 the patient to the initial carrier wave signal for about ten minutes. Following the initial about ten-minute exposure, the system can expose 6415 the patient to the initial modulated frequency signal for about 120 minutes, about 60 minutes, about 35 minutes, or about 10 minutes as described herein. The system can then determine 6425 if the patient is to be exposed for an additional period to the modulated frequency signal. If the patient is to be exposed for another period, the process can return to step 6415 where the system exposes the patient to another modulated frequency exposure period for about 120 minutes, about 60 minutes, about 35 minutes, or about 10 minutes. In some embodiments, following the initial modulated frequency exposure, the system can expose 6415 the patient to another modulated frequency exposure. In some embodiments, the additional modulated frequency exposure comprises the modulated frequencies that altered a hemodynamic parameter, for example heart rate variability. In some embodiments, the additional modulated frequency exposure comprises the modulated frequencies that did not alter a hemodynamic parameter, for example heart rate variability. In some embodiments, the additional modulated frequency exposure comprises a series of electromagnetic frequencies that occur every 1 Hz, 3 Hz or 10 Hz in a range from about 0.01 Hz to about 20 KHz, from about 10 Hz to about 1,000 Hz, or from about 10 Hz to about 2,000 Hz. In some embodiments, the modulated frequencies applied to the patient can be a series of electromagnetic frequencies that occur every 3 Hz in a range from about 0.01 Hz to about 20 KHz. In some embodiments, the modulated frequencies applied to the patient can be a series of electromagnetic frequencies that occur every 3 Hz in a range from about 10 Hz to about 1,000 Hz. In some embodiments, the modulated frequencies applied to the patient can be a series of electromagnetic frequencies that occur every 3 Hz in a range from about 10 Hz to about 2,000 Hz. In some embodiments, the modulated frequencies applied to the patient can be a series of electromagnetic frequencies that occur every 10 Hz in a range from about 0.01 Hz to about 20 KHz. In some embodiments, the modulated frequencies applied to the patient can be a series of electromagnetic frequencies that occur every 10 Hz in a range from about 10 Hz to about 1,000 Hz. In some embodiments, the modulated frequencies applied to the patient can be a series of electromagnetic frequencies that occur every 10 Hz in a range from about 10 Hz to about 2,000 Hz. Following the initial or additional modulated frequency exposure, the system can expose 6420 the patient to another carrier wave exposure period for about ten minutes. If the patient is not to be exposed to another modulated frequency period, the process ends.

As noted above, the timing and order of exposure periods as shown in FIG. 25 are provided by way of example only. Additionally, in certain implementations, the determination of whether to perform another exposure period can be determined by another decision maker such as a patient's physician.

The statistical algorithms described herein can include machine learning or other similar statistical-based modeling techniques. For example, the particular algorithm used may depend on an expected outcome of using the algorithm. For example, a processing device can be configured to use a first process or algorithm to calculate refinements to a derived weight as described above based upon a first set of outcomes data while using a second or different process/algorithm to calculate refinements to a derived weight as described above based upon a second set of outcomes data. Different methods and algorithms may be used to calculate the refined weights in concert or substantially simultaneously. The output of each of the different methods and algorithms can then be compared/further analyzed to determine which output is most highly rated, or the output of each method and algorithm can be combined into a combinational metric.

In some implementations, a computational statistics model as described in further detail below can be trained on a large population, for example, a population that can range from several thousands to tens of thousands of patient records comprising electrophysiology, demographic, medical history information, quality of life, survival, and/or hospital admission of a patient. The computational statistics tool can include, but is not limited to, penalized regression/classification techniques such as random forest and gradient boosting (e.g., implemented using R or any other statistical/mathematical programming language), Bayesian belief networks, collaborative filters, support vector machines, and other similar techniques. Any other classification-based computational statistics tool can be used, including neural networks (as described in more detail below) and support vector machines. Because the computational statistics tool may be computationally intensive, some or all of the processing for the computational statistics tool may be performed on a server that is separate from the monitoring system.

An overview of how a random forest tool may be applied to a given dataset can illustrate how a classification tool may work in interpreting given input data. A random forest is a collection of decision trees. A decision tree is a flow chart-like structure in which each node represents a test on a metric and each branch represents a potential outcome of the test. The tree culminates in a classification label, e.g., a decision taken at the end after computing each of the metrics. Each tree in a random forest tool gets a "vote" in classifying a given set of metrics. There are two components of randomness involved in the building of a random forest. First, at the creation of each tree, a random subsample of the total data set is selected to grow the tree. Second, at each node of the tree, a "splitter variable" is selected and the underlying patients are separated into two classes. For example, patients in one class (e.g., positive response to a specific drug) can be separated from those in another class (e.g., negative response to a specific drug). The tree is grown with additional splitter variables until all terminal nodes (leaves) of the tree are purely one class or the other. The tree is "tested" against patient records that have been previously set aside. Each patient testing record traverses the tree, going down one branch or another depending on the metrics included in the record for each splitter variable. The patient testing record is assigned a predicted outcome based on where the record lands in the tree (a vote). The entire process may be repeated with new random divisions of the underlying dataset to produce additional trees and ultimately a "forest". In each case, a different subset of patients can be used to build the tree and test its performance.

In developing the results described in the below example implementation, a predetermined number of model variations are trained. For example, each model variation is labeled sequentially (e.g., for 100 runs, labeled from 1-100). In each run of the model, the software randomly samples a predetermined portion (e.g., an 80% portion) of the population as the training set and sets aside the remainder (e.g., 20%) as the validation set.

As noted above, the computational statistics tool can train the model on a first portion of the underlying dataset and validate the model on a second portion of the dataset or on another separate dataset. When evaluating the performance of each model, the performance of the underlying decisions within the decision trees in the random forest can be evaluated based on specificity and sensitivity parameters. For example, the sensitivity parameter can be based on a measure of the model's ability to correctly predict whether a patient is at risk of reacting negatively to a drug treatment. For example, the sensitivity parameter may be based on a proportion of patients that the model correctly predicts will react negatively to a treatment. The specificity parameter can be based on the proportion of patients who are to be treated with a specific drug, and who are predicted by the relevant model as reacting positive to the drug treatment. It may be advantageous to optimally balance individual performance variables such as sensitivity and specificity at a high level. For example, by setting the specificity at a relatively high value, e.g., 95%, the underlying thresholds within the classifier model may be adjusted to minimize false positives. After the specificity is defined, the measure of sensitivity can be treated as a type of performance measure, e.g., generally in the range of 15-35% for a given model; however, smaller or larger values of sensitivity are also possible.

A validation protocol, for example, as described below, can be employed to validate the predictive performance of trained models. In an implementation, the validation phase can be used to ascertain appropriate threshold scores for classifying future patients (where an outcome is currently unknown and a prediction of the outcome is desired) and to determine the predictive performance of each classifier model generated by the computational statistics tool. For validating the various models and associated threshold scores, a second group of individuals, e.g., a validation population (or cohort), can be used. For example, the validation population used can be a new validation population. The outcome for the patients in the validation cohort is eventually learned as these patients progress through treatment. In an embodiment, the patients in the validation population can be different from the group of training and test patients described above for training the model. For example, a validation population of patients and their associated metrics (validation metrics) can be independent from a training population of patients and associated metrics (training metrics). In some implementations, there may be an overlap between the validation metrics and the training metrics.

In some implementations, the validation population can be updated by at least one of adjusting one or more of the metrics in the validation metrics, and expanding the validation metrics based on appending one or more additional subjects to the population of subjects that make up the validation population. The thresholds for classifying future patients can be refined based on the updated validation metrics. For example, metrics of a patient that is currently being treated or monitored or has otherwise not progressed through the treatment can be used to adjust the one or more metrics in the validation metrics. Alternatively or additionally, the patient's metrics can be added to the validation population as metrics from a new subject. The validation metrics can be adjusted as new metrics for the patient are determined during the monitoring or treatment of the patient. In some examples, as a monitored patient progresses through treatment, the patient's metrics can be added to the validation population and/or used to adjust the metrics in the validation metrics after the patient has progressed through the treatment.

In some implementations, the training population can be updated by at least one of adjusting one or more of the metrics in the training metrics and expanding the training metrics based on appending one or more additional subjects to the first plurality of subjects. The classifier models can be retrained based on the updated training metrics. For example, as additional patient metrics are determined from current patients and/or metrics from new patients are determined, the model can be retrained, e.g., on the increased number of metrics or on new, different metrics, to provide updated classifier models. The training population can be updated as new metrics for current patients and/or metrics for new patients are determined or after patients have progressed through treatment.

Figure 22:
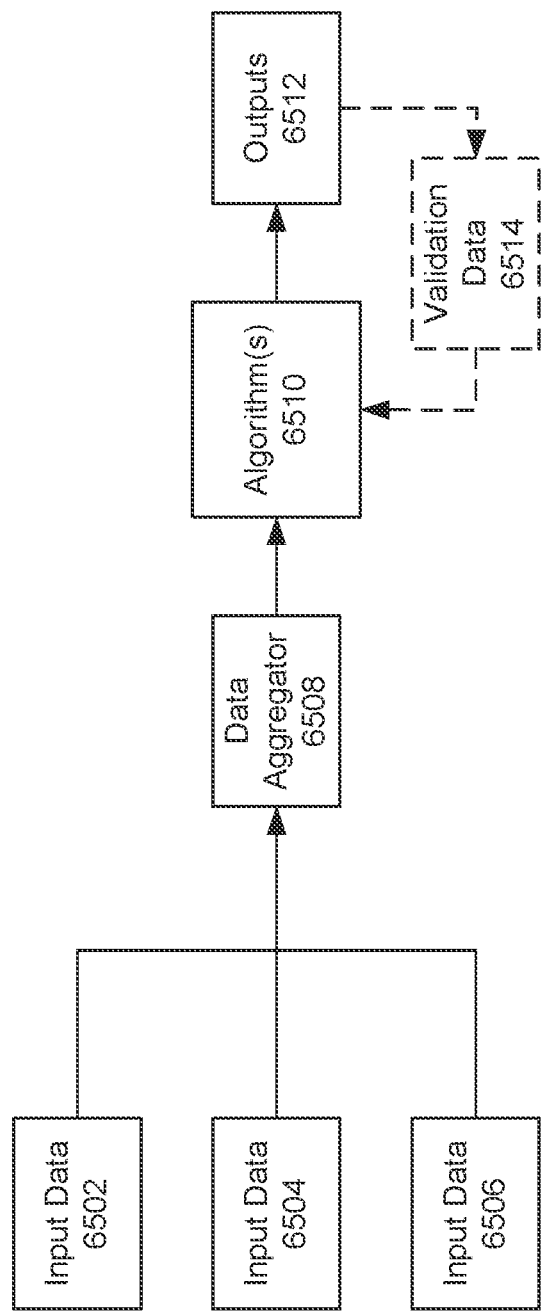
FIG. 22 illustrates a sample flow for training a computational statistics algorithm according to an embodiment.

FIG. 22 illustrates a sample flow for training and validating one or more classifier models for a computational statistics algorithm as described above. A set or population of known input data 6502, 6504, 6506 can be provided as the data set used to train and validate the classifier models. For example, the known patient records data set may include 1000 patients that have been diagnosed with a specific ailment (such as HCC), their drug treatment regimens, and the associated outcomes for each patient. A percentage of the known patient data records can be used as the input data 6502, 6504, 6506. For example, 80%, or 800, of the patient records can be used as the input 6502, 6504, 6506.

The input data 6502, 6504, 6506 can be fed into a data aggregator 6508. The data aggregator 6508 can be configured to match patient data into a single training input for the computational statistics algorithm and configure the training input into a format readable by the computational statistics algorithm. The data aggregator 6508 can feed the training data into algorithm 6510. The algorithm 6510 can include one or more untrained data structures such as a series of data trees (e.g., organized using a random forest tool as described above). Using the training input variables and known outcomes from the input data 6502, 6504, 6506, the algorithm 6510 can iteratively process each data point in the training set, thereby training the data structures to more accurately produce the expected (and known) outcomes.

Once the algorithm 6510 has exhausted the input data 6502, 6504, 6506, the algorithm can generate one or more outputs 6512. The outputs 6510 can be compared against the expected output (as know from the initial population) to determine the specificity and sensitivity of the now-trained algorithm 6510. In certain implementations, validation data 6514 can be used to further refine the trained algorithm 6510 using additional patient records. For example, the validation data 6514 can be input into a validation module for validation of the one or more trained algorithms 6510. To continue the above example, the validation data 6514 can include 200 patient records. Typically, there is no overlap between a training data set and a validation data set as there is no advantage to running the same data twice.

As the validated classifier models is used to classify new patients (e.g., to produce new outputs for a set of patient metrics as described herein), the produced outcomes can be used to better validate the process using a closed loop feedback system. For example, as a patient is classified and treated, the result of that treatment can be included in the patient record and verified by, for example, the patient's physician. The patient's record, now updated to include a known outcome, can then be provided as feedback to the validation module. The validation module can process the feedback, comparing a generated output against the known outcome for the patient. Based upon this comparison, the validation module can further refine the validated algorithms, thereby providing a closed loop system where the models are updated and upgraded regularly.

Once trained, the algorithms 6510 can be implemented as described herein. Using the trained algorithms, a system such as system 900 can monitor a patient's response to applied electromagnetic energy (e.g., by measuring the patient's HRV during the exposure) to both diagnose whether the patient has, for example, HCC and what the prognosis is for treatment of the patient, or what the prognosis is for the patient's quality of life, survival, or hospital admission. As noted above, an added benefit of the exposure to the electromagnetic energy can be simultaneous treatment of the cancer during diagnosis and long-term prognostication.

Figure 26:
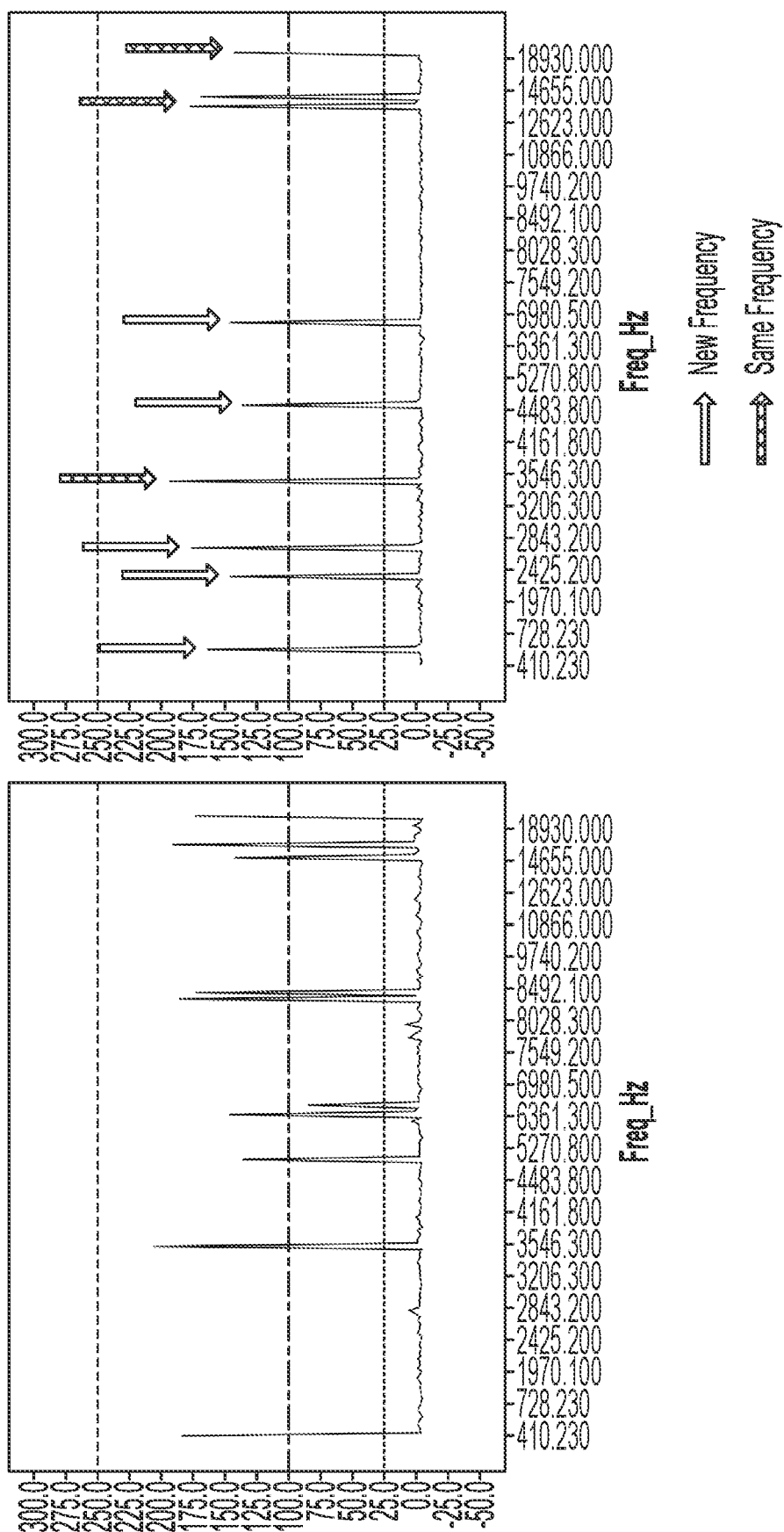
FIG. 26 illustrates a set of patient response graphs according to an embodiment.

In certain examples, immediate changes to a patient's response to the applied energy can be observed. For example, as shown in FIG. 26, the left graph indicates a patient's response to various applied frequencies during a first about 35-minute therapy session (e.g., as described above in relation to FIGS. 23A-D). The right graph of FIG. 26 illustrates a patient's response to the same set of frequencies after an about ten-minute rest period. In some embodiments, a patient's response to the same set of frequencies occurs without an about ten-minute rest period as depicted in FIG. 23D. As shown in FIG. 26, while several frequencies cause a similar reaction in the patient, there are now new frequencies that cause a reaction in the patient (e.g., noticeable changes in the patient's HRV) and several previously identified frequencies that the patient is not responding to after the rest period. Such a result may indicate immediate cellular changes in the patient caused by the initial about 35-minute exposure period.

Figure 27A:
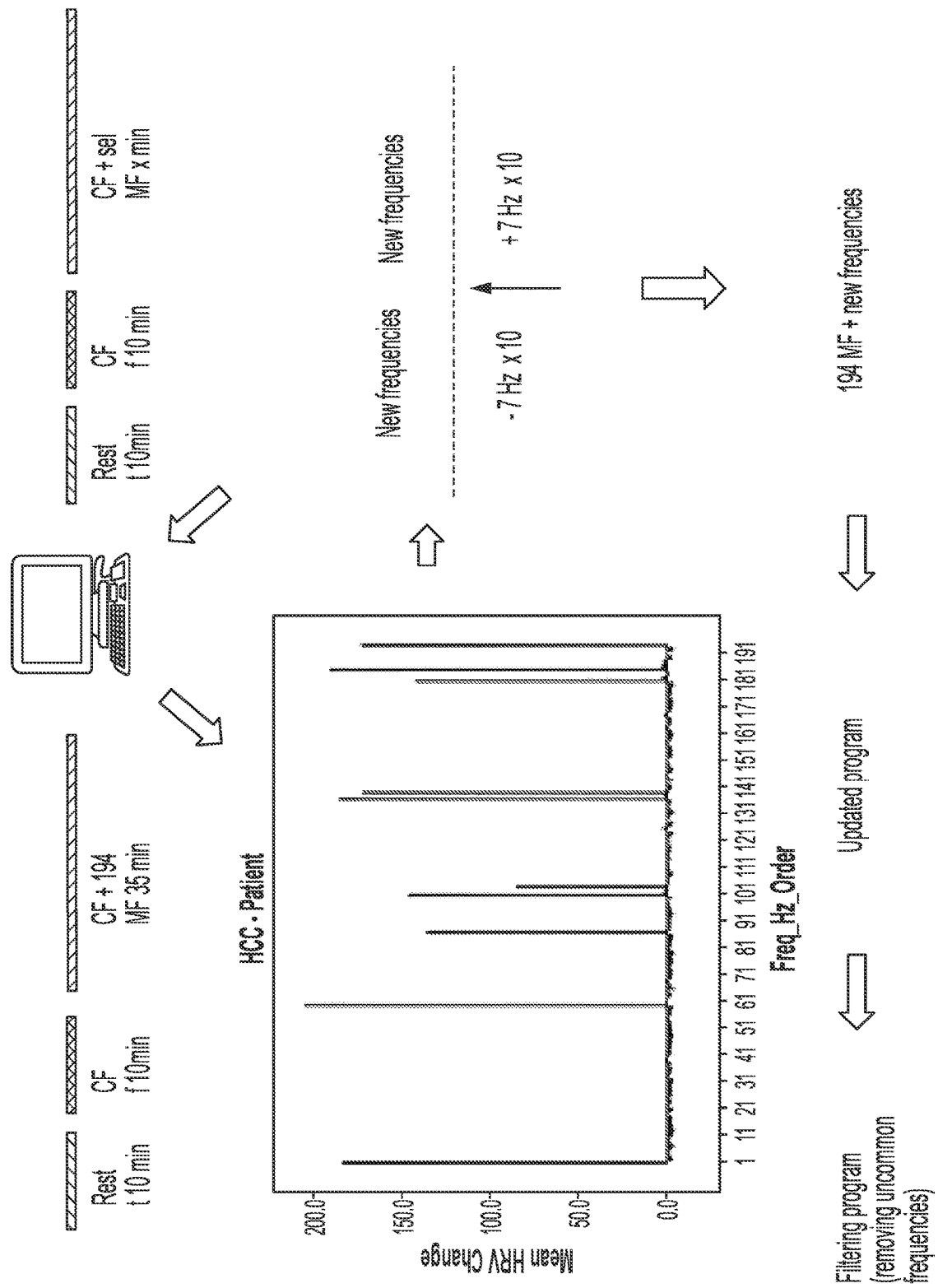
FIG. 27A illustrates a diagram representing a signal exposure protocol over the course of one day in accordance with an embodiment.

As illustrated in FIG. 27A, in some embodiments, the patient can be relaxed in a supine position. An initial non-exposure period (i.e., rest) of about ten minutes can be included to allow for the patient to relax and establish baselines for various hemodynamic parameters and HRV. After the initial non-exposure period, the patient may be exposed to a carrier frequency (i.e., at a constant amplitude without amplitude modulation) for about ten minutes. After the initial exposure period, the patient may be exposed to a modulated frequency exposure period for about 120 minutes, about 60 minutes, about 35 minutes, or about 10 minutes. During this time, each of the set of frequencies (e.g., a series of electromagnetic frequencies that occur every 1 Hz, 3 Hz or 10 Hz in a range from about 0.01 Hz to about 20 KHz, from about 10 Hz to about 1,000 Hz, or from about 10 Hz to about 2,000 Hz as described herein) can be applied to the patient for a particular period of time (e.g., 10 seconds per frequency or 3 seconds per frequency). In some embodiments, the modulated frequencies applied to the patient can be a series of electromagnetic frequencies that occur every 3 Hz in a range from about 0.01 Hz to about 20 KHz. In some embodiments, the modulated frequencies applied to the patient can be a series of electromagnetic frequencies that occur every 3 Hz in a range from about 10 Hz to about 1,000 Hz. In some embodiments, the modulated frequencies applied to the patient can be a series of electromagnetic frequencies that occur every 3 Hz in a range from about 10 Hz to about 2,000 Hz. In some embodiments, the modulated frequencies applied to the patient can be a series of electromagnetic frequencies that occur every 10 Hz in a range from about 0.01 Hz to about 20 KHz. In some embodiments, the modulated frequencies applied to the patient can be a series of electromagnetic frequencies that occur every 10 Hz in a range from about 10 Hz to about 1,000 Hz. In some embodiments, the modulated frequencies applied to the patient can be a series of electromagnetic frequencies that occur every 10 Hz in a range from about 10 Hz to about 2,000 Hz. The system can cycle repeatedly through each of the frequencies for the exposure period. After the initial modulated frequency exposure period, the system may determine the set of frequencies (i.e., "active frequencies") that altered a hemodynamic parameter (e.g., heart rate variability). In some embodiments, the system may determine a set of new frequencies that altered or did not alter a hemodynamic parameter during the first exposure period. In some embodiments, the set of new frequencies is within a range from about 0 Hz to about 10 Hz of the first set of frequencies that altered or did not alter a hemodynamic parameter (e.g., heart rate variability), preferably from about 0 Hz to about 7 Hz as depicted in FIG. 27B in patients with high tumor load and with low tumor load. In some embodiments, the set of new frequencies can be combined with a series of electromagnetic frequencies that occur every 3 Hz or 10 Hz in a range from about 0.01 Hz to about 20 KHz, in a range from about 10 Hz to about 1,000 Hz, or in a range from about 10 Hz to about 2,000 Hz as described herein to provide a patient-specific exposure protocol. In some embodiments, the modulated frequencies applied to the patient can be a series of electromagnetic frequencies that occur every 3 Hz in a range from about 0.01 Hz to about 20 KHz. In some embodiments, the modulated frequencies applied to the patient can be a series of electromagnetic frequencies that occur every 3 Hz in a range from about 10 Hz to about 1,000 Hz. In some embodiments, the modulated frequencies applied to the patient can be a series of electromagnetic frequencies that occur every 3 Hz in a range from about 10 Hz to about 2,000 Hz. In some embodiments, the modulated frequencies applied to the patient can be a series of electromagnetic frequencies that occur every 10 Hz in a range from about 0.01 Hz to about 20 KHz. In some embodiments, the modulated frequencies applied to the patient can be a series of electromagnetic frequencies that occur every 10 Hz in a range from about 10 Hz to about 1,000 Hz. In some embodiments, the modulated frequencies applied to the patient can be a series of electromagnetic frequencies that occur every 10 Hz in a range from about 10 Hz to about 2,000 Hz. In some embodiments, the patient-specific exposure protocol is administered to the patient. In some embodiments, the patient-specific exposure protocol is administered prior to or after a rest period of about ten minutes. In some embodiments, the patient-specific exposure protocol does not include frequencies that did not produce an alteration in the hemodynamic parameter (e.g., heart rate variability).

In some embodiments, new active frequencies are determined by the distribution of active frequencies, as illustrated in FIG. 28. In some embodiments, the distribution of active frequencies is transformed by the equation: $X \cap N(\mu; \sigma^2)$, wherein X is a random variable with normal distribution of mean $\mu$ and variance $\sigma^2$. So $\sigma = +\sqrt{\sigma^2}$ is the standard deviation. The Gaussian transformation that takes a random variable $X \cap N(\mu; \sigma^2)$ to the standard normal distribution $Z \cap N(0; 1)$ can be: $Z_1(X) = x_i - \mu(x)/\sigma(x)$. (eqn. 1) (Standardized variable). In some embodiments, with this transformation of variables, a random variable X with mean $\mu(x)$ and variance $\sigma^2(x)$ may be transformed into a random variable with mean $\mu(z)=0$ and variance $\sigma^2(z)=1$.

In some embodiments, the central limit theorem may provide a sample distribution of means wherein $Z(\overline{x}_i) = \overline{x}_i - \mu(x)/\sigma(x)\sqrt{n}$ (eqn. 2). In some embodiments, the sample distribution of means tends to a normal distribution as it grows: $Z(\overline{x}_i) \cap N(0; 1)$. In some embodiments, special groups of frequencies may be referred to as outlined frequencies of the form $\theta_i$, $i=1, 2, \ldots, 2\mu+1$, where $\theta_1 =$ $$\begin{bmatrix} (u-j)\delta, \text{ if } f < \overline{f} \\ 0, \text{ if } f = \overline{f} \\ (u-j)\delta \text{ if } f > \overline{f} \end{bmatrix}$$

$$j = 0, 1, \ldots, (u-1). \quad \text{(eqn. 3)}$$

$$f - (u-0)\delta, f - (u-1)\delta, f - (u-2)\delta, \ldots, f - \delta,$$
$$f = \overline{f}, f + \delta, \ldots, f + (u-2)\delta, f + (u-1)\delta, f + (u-0)\delta$$

where:
  f is an active frequency selected in the previous step. By construction $f = 84\overline{f}$;
  $\mu$ is the number of frequencies that can be added below and above f; (eqn. 4)
  $\delta$ is the constant difference between these frequencies.
Then, the number of frequencies under study can be: $n=2u+1$.
By construction, the delineated frequency distribution (eqn. 3) can have a mean $\overline{\theta} = \overline{f}$,
where it can be naturally an active frequency $\overline{f}=f$ obtained in the previous exposures.
Further, it may prove that its sample standard deviation can be:

$$S(\theta) = \left[\frac{\delta^2}{6}(u+1)(2u+1)\right]^{1/2} \quad \text{(eqn. 5)}$$

The set of frequencies delineated may be normally distributed:

$$\theta \cap N\left\{\overline{f}; \frac{\delta^2}{6}(u+1)(u+2)\right\}$$

Figure 29:
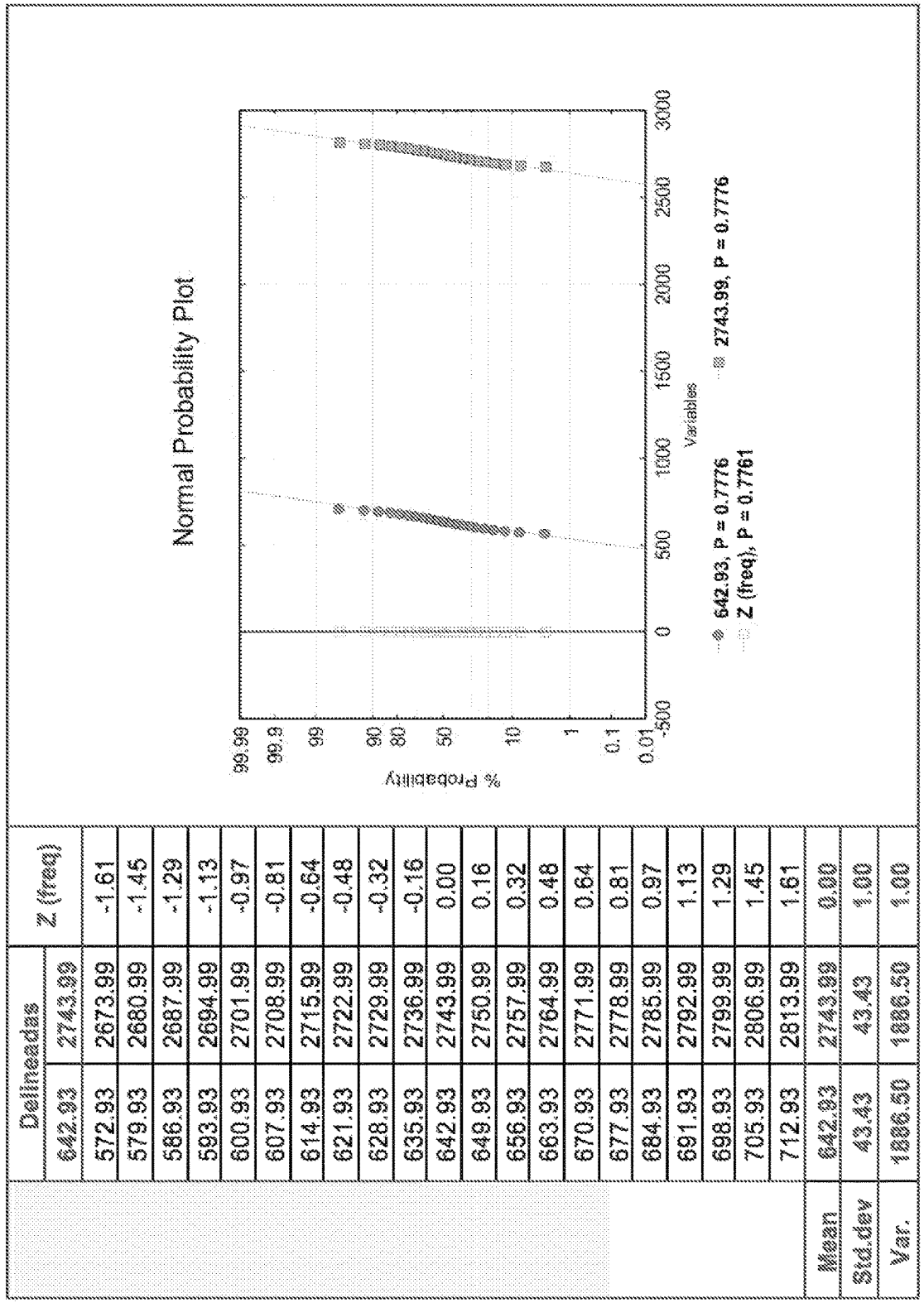
FIG. 29 illustrates the distribution of active frequencies in accordance with a further embodiment.

In some embodiments, normality may not occur with the baseline distal variables (DISD1, heart rate variability). In some embodiments, there may be occurrences of outliers. As illustrated in FIG. 29, two types of atypical values may be considered: the outliers and the influential points or leverage points.

In some embodiments, identification of outliers and influential points may be performed. In some embodiments, identification of outliers and influential points may be performed by the graphical criterion of Normal Probability Plot to detect potentially outliers and/or influential points, the studentized residue $(RS)_i$ and Cook's distance $(D_i)$ to "confirm or not" the influential points.

In some embodiments, a linear regression model may be considered:

$$y = X\beta + e; \beta = \begin{bmatrix} \beta_0 \\ \beta_1 \end{bmatrix}; \text{characterized by:}$$

$$Z(DIDS1)_i = \beta_0 + \beta_1 (freq_{Hz})_i + e_i$$

(a) The observations (DISD1) submitted may be considered outliers. $\|RS\| > 2.0$
(b) Cook's distance to analyze the influence of the i-order of the answer may be defined by:

$$D_i = \frac{r_i^2 h_{ii}}{k(1 - h_{ii})^2}$$

Where, in a linear regression model of Z(DISD1) as a function of Z (freq):
$r_i$ is the studies residue of the response;
k is the number of parameters of the model;
$h_{ii}$ is the—nth diagonal value of the orthogonal projector of the vector of the responses on the space generated by the columns of the matrix X of the design: $H = X(X'X)^{-1}X'$ also known as Hat matrix y.
In some embodiments, $(DISD1)_i$ can be influential if $$D_i > \frac{2(k+1)}{2u+1}$$

Figure 30:
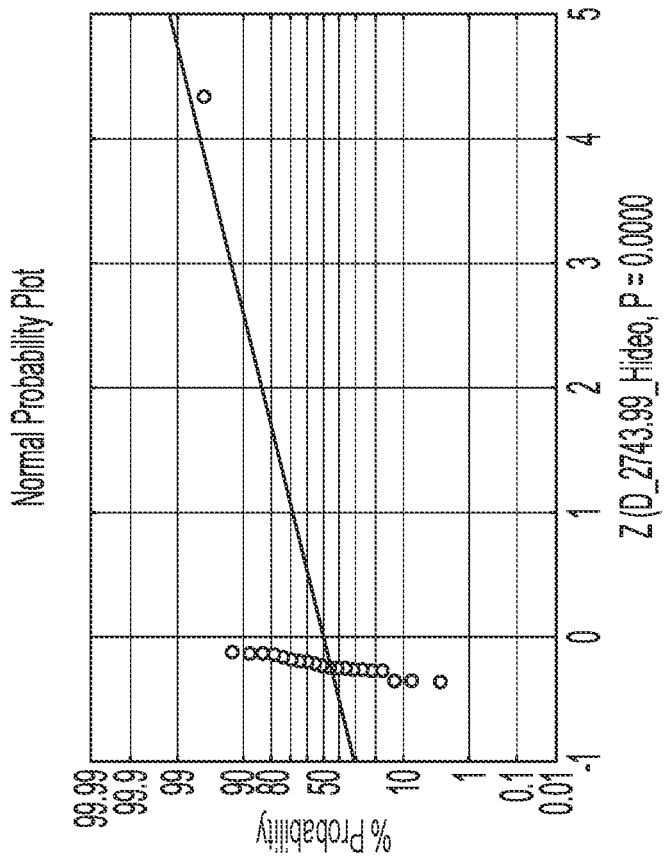
FIG. 30 illustrates a normal probability plot construction in accordance with an embodiment.

As depicted in FIG. 30, an influential point example of a normal probability plot construction, in accordance with embodiments disclosed above, may have a delta for frequency response of about 3 Hz. In some embodiments, the delta for frequency response of about 3 Hz may be independent of frequency value.

Figure 31:
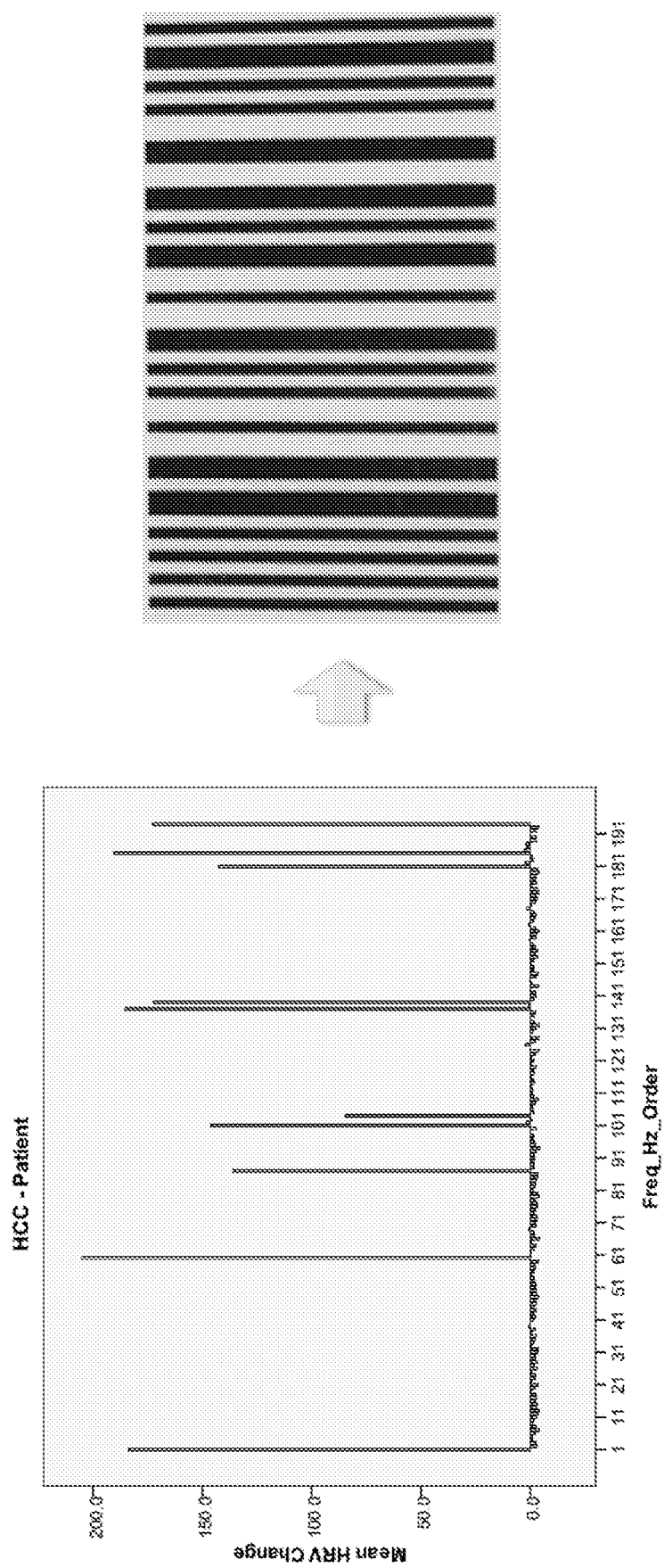
FIG. 31 illustrates a bar coding system in accordance with an embodiment.
Figure 32:
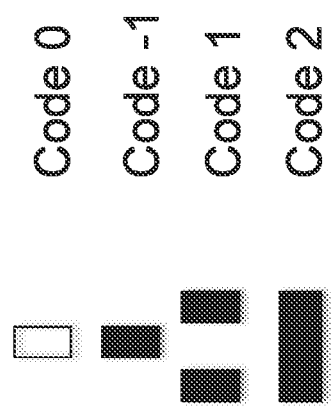
FIG. 32 illustrates a bar coding system in accordance with a further embodiment.
Figure 33:
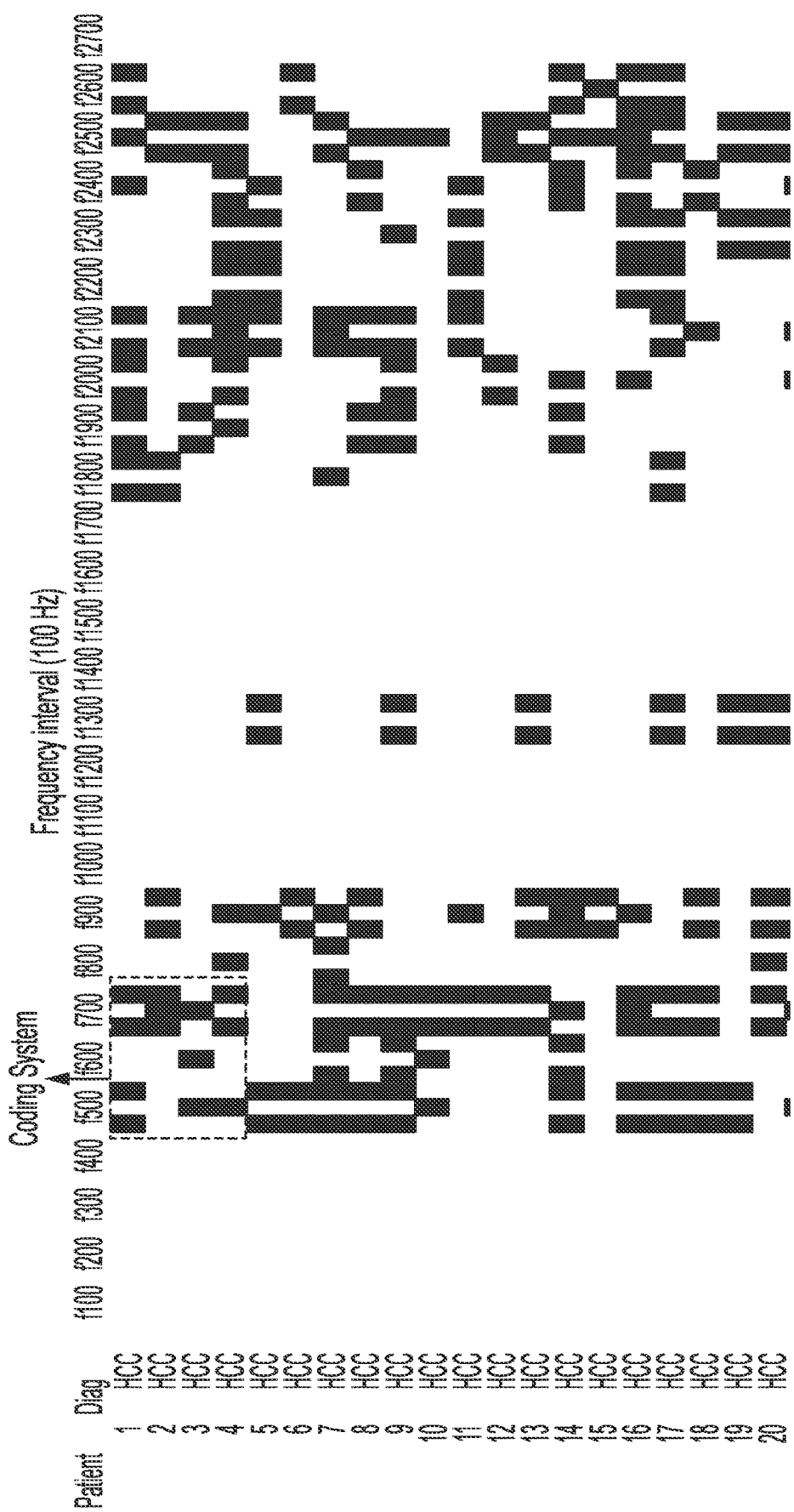
FIG. 33 illustrates a bar coding system for diagnosing healthy patients and hepatocellular carcinoma patients in accordance with an embodiment.
Figure 33:
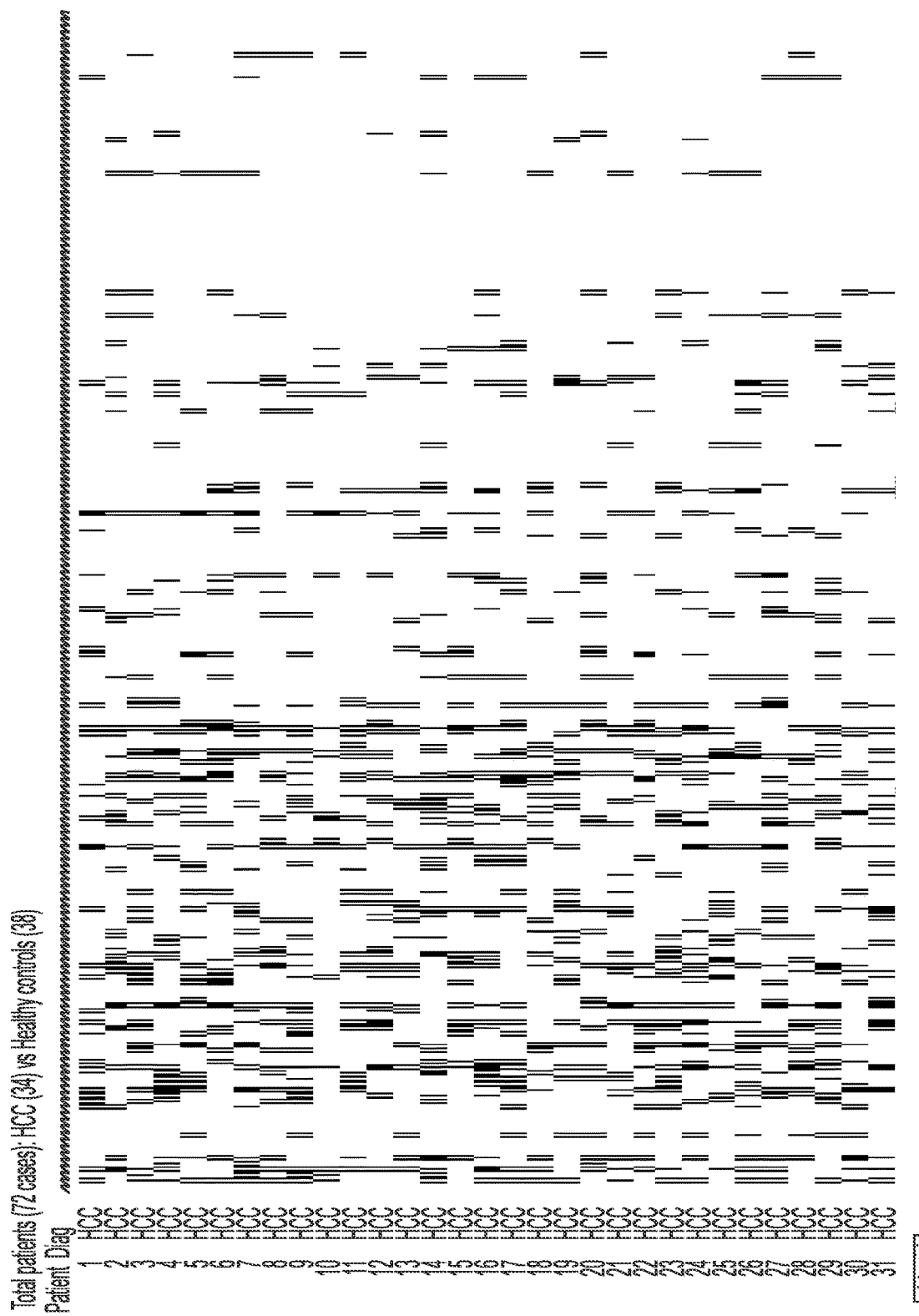
Figure 33:
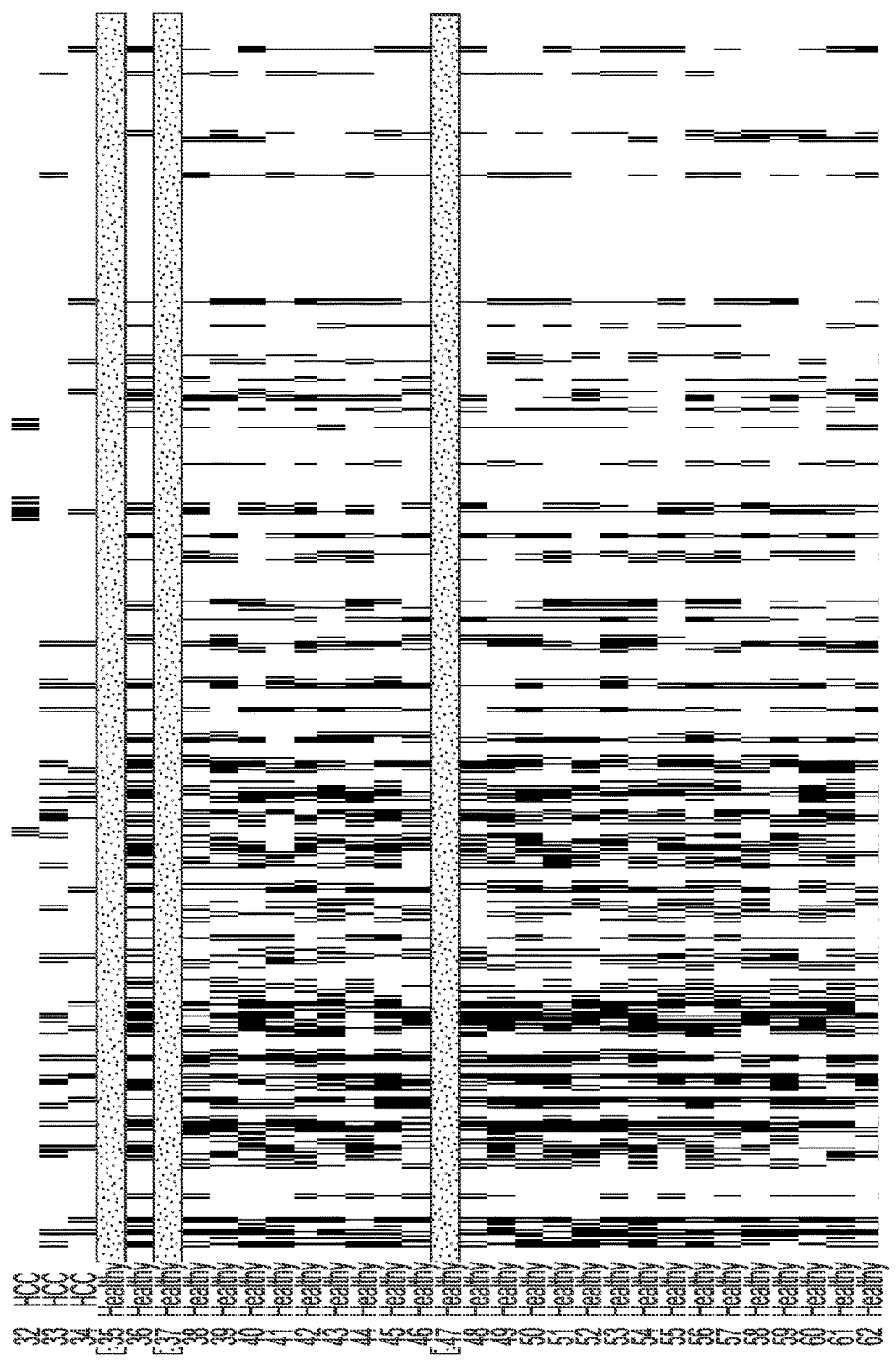
Figure 33:
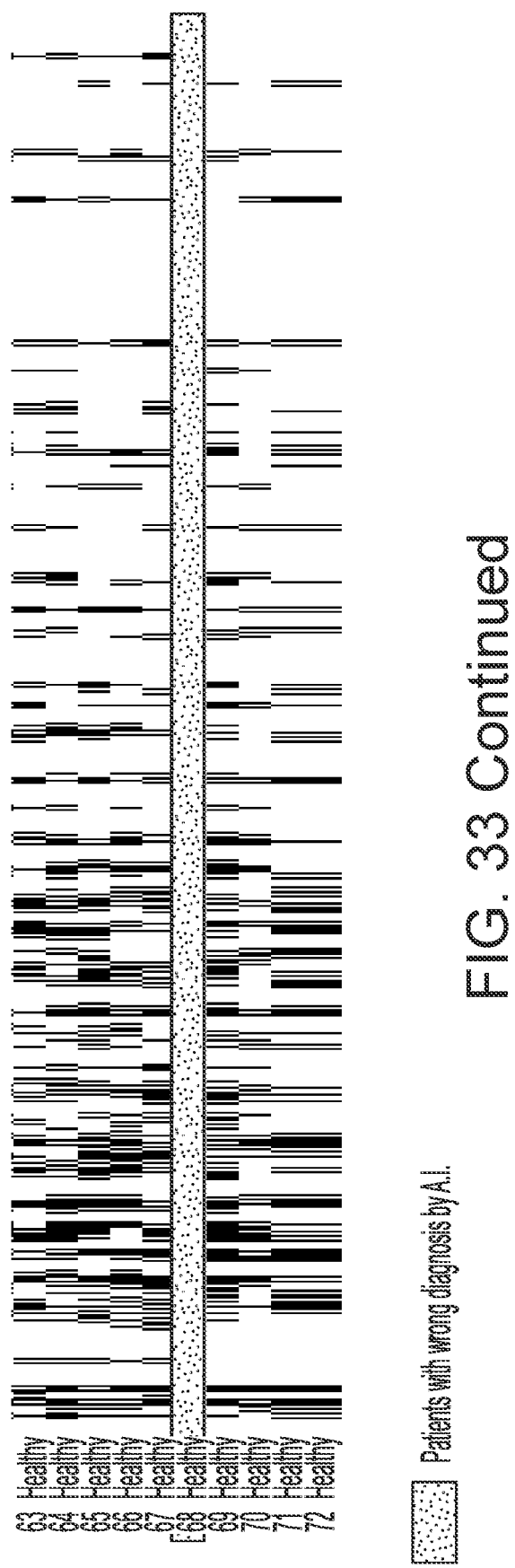

In some embodiments the patient can be relaxed in a supine position. An initial non-exposure period (i.e., rest) of about ten minutes can be included to allow for the patient to relax and establish baselines for various hemodynamic parameters and HRV. After the initial non-exposure period, the patient may be exposed to a carrier frequency (i.e., at a constant amplitude without amplitude modulation) for about ten minutes. After the initial exposure period, the patient may be exposed to a modulated frequency exposure period of about 120 minutes, about 60 minutes, about 35 minutes, or about 10 minutes. During this time, each of the set of frequencies (e.g., a series of electromagnetic frequencies that occur every 1 Hz, 3 Hz or 10 Hz in a range from about 0.01 Hz to about 20 KHz, from about 10 Hz to about 1,000 Hz, or from about 10 Hz to about 2,000 Hz as described herein) can be applied to the patient for a particular period of time (e.g., 10 seconds per frequency or 3 seconds per frequency). In some embodiments, the modulated frequencies applied to the patient can be a series of electromagnetic frequencies that occur every 3 Hz in a range from about 0.01 Hz to about 20 KHz. In some embodiments, the modulated frequencies applied to the patient can be a series of electromagnetic frequencies that occur every 3 Hz in a range from about 10 Hz to about 1,000 Hz. In some embodiments, the modulated frequencies applied to the patient can be a series of electromagnetic frequencies that occur every 3 Hz in a range from about 10 Hz to about 2,000 Hz. In some embodiments, the modulated frequencies applied to the patient can be a series of electromagnetic frequencies that occur every 10 Hz in a range from about 0.01 Hz to about 20 KHz. In some embodiments, the modulated frequencies applied to the patient can be a series of electromagnetic frequencies that occur every 10 Hz in a range from about 10 Hz to about 1,000 Hz. In some embodiments, the modulated frequencies applied to the patient can be a series of electromagnetic frequencies that occur every 10 Hz in a range from about 10 Hz to about 2,000 Hz. The system can cycle repeatedly through each of the frequencies for the exposure period. After the modulated frequency exposure period, the system may determine the set of frequencies (i.e., "active frequencies") that altered a hemodynamic parameter (e.g., heart rate variability). In some embodiments, the system may determine a set of new frequencies that altered or did not alter a hemodynamic parameter during the first exposure period. In further embodiments, the system may determine a frequency attribute for the set of frequencies that altered or did not alter a hemodynamic parameter. In some embodiments, the frequency attribute can be, as a non-limiting example, a bar coding system as depicted in FIG. 31. In some embodiments, the frequency attribute can be ascribed a code wherein the code can be code 0, code −1, code 1, code 2, or a combination thereof. As illustrated in FIGS. 32-33, in some embodiments, the frequency attribute can be code 0 wherein code 0 is illustrated as 0 bar in the bar coding system, the frequency attribute can be code −1 wherein code −1 is illustrated as 1 bar in the bar coding system, the frequency attribute can be code 1 wherein code 1 is illustrated as 2 bars in the bar coding system, the frequency attribute can be code 2 wherein code 2 is illustrated as 3 bars, 3 sequential bars with no void in between the 3 sequential bars, in the bar coding system, or a combination thereof. In further embodiments, the code 0 may indicate a frequency did not produce a change in a hemodynamic parameter (e.g., heart rate variability), the code −1 may indicate a frequency produced a decrease in a hemodynamic parameter (e.g., heart rate variability), the code 1 may indicate a frequency produced an increase in a hemodynamic parameter (e.g., heart rate variability), and the code 2 may indicate a frequency produced a very high increase or decrease in a hemodynamic parameter (e.g., heart rate variability). In some embodiments, the bar-coding system has a frequency interval. In some embodiments, the bar coding system has a frequency interval of about 1 Hz, about 3 Hz, about 5 Hz, about 10 Hz, about 20 Hz, about 30 Hz, about 40 Hz, about 50 Hz, about 60 Hz, about 70 Hz, about 80 Hz, about 90 Hz, about 100 Hz, about 125 Hz, about 150 Hz, about 175 Hz, about 200 Hz, or any range in between inclusive. In some embodiments, the bar-coding system has a frequency interval of about 100 Hz.

The following Examples are provided solely for illustrative and exemplary purposes and are not intended to limit the invention in any way.

Example 1

Hemodynamic Stress Response to AM EMF Exposure

In a validation trial, an integrated system capable of collecting large volumes of digital data in synchronization between the Autem gEM generator and the Task Force Monitor was designed and used to identify the hemodynamic response to AM EMF exposure. A mathematical computing process was constructed that integrated multivariate hemodynamic parameter analysis by geometric data transformation in order to identify points that were not consistent with their neighbors. An explanatory model was produced by self-non-stationary regression indicating periodic fluctuations, a general upward or downward trend and allowable stochastic fluctuations. As demonstrated in FIG. 5, statistical time-domain measures identified instantaneous hemodynamic changes induced by AM EMF frequency modulation during very small cycle intervals.

A total of 48 patients with advanced hepatocellular carcinoma (HCC) and 45 healthy controls were exposed in supine position to a 27.12 MHz carrier frequency for 10 minutes (baseline period) followed by the same carrier frequency modulated at specific very low frequencies from 10 to 20 KHz (modulation period) for 30 minutes to 55 minutes according to a frequency modulation schedule. Instantaneous hemodynamic response alterations characterized by a significant change in a geometric transformed parameter value were extracted from the beat-to-beat hemodynamic time series for further analysis in the prediction model. Those extracted values represent a small fraction of the entire hemodynamic time series.

In order to determine whether the autonomic hemodynamic stress response was induced by the 27.12 MHz carrier frequency or by the modulation of the carrier frequency, a comparative analysis was performed between the baseline and modulation periods considering the number of hemodynamic stress response events for each patient, having the time of exposure as a covariate. The number of hemodynamic stress response events observed during the modulation period was significantly higher than the events observed during the baseline period for patients with advanced HCC ($p<0.0001$) and healthy controls ($p=0.0156$) (Table 2).

TABLE 2

| Exposure | Group | Modulation events | p-value |
|---|---|---|---|
| Baseline | HCC | 170 | |
|  | Healthy control | 25 | |
|  | Total | 195 | |
| Modulation | HCC | 689 | |
|  | Healthy | 127 | |
|  | Total | 816 | |
| All | HCC | 859 | 3.09E−06 |
|  | Healthy control | 152 | 0.0156 |
|  | Total | 1011 | |

During the modulation period, the percentage of observed hemodynamic stress response events was significantly higher in patients with advanced HCC than the healthy controls (p=0.0017).

The autonomic hemodynamic stress response characteristics, extracted from AM EMF exposure procedure data by the Hdp monitoring system, represent the allostatic response to repetitive AM EMF stimuli that may reflect the allostatic load status of an individual patient. The precise and instantaneous time-domain hemodynamic alterations recorded by the Hdp monitoring system represent a robust, objective and reproducible access to the patient's allostatic load capacity (or overload).

Example 2

Quality of Life (QoL) Measurements and Prognosis in Cancer

Previous studies suggest a positive relationship between quality of life measurements and the duration of survival in cancer patients. Pre-treatment (baseline) quality of life data appeared to provide the most reliable information for helping physicians to establish prognostic criteria for treating their cancer patients. Predictive or prognostic indicators were defined as any independent variables (e.g., health-related quality of life parameters) that can be used to estimate the chance of a given outcome (e.g., survival duration).

Figure 6:
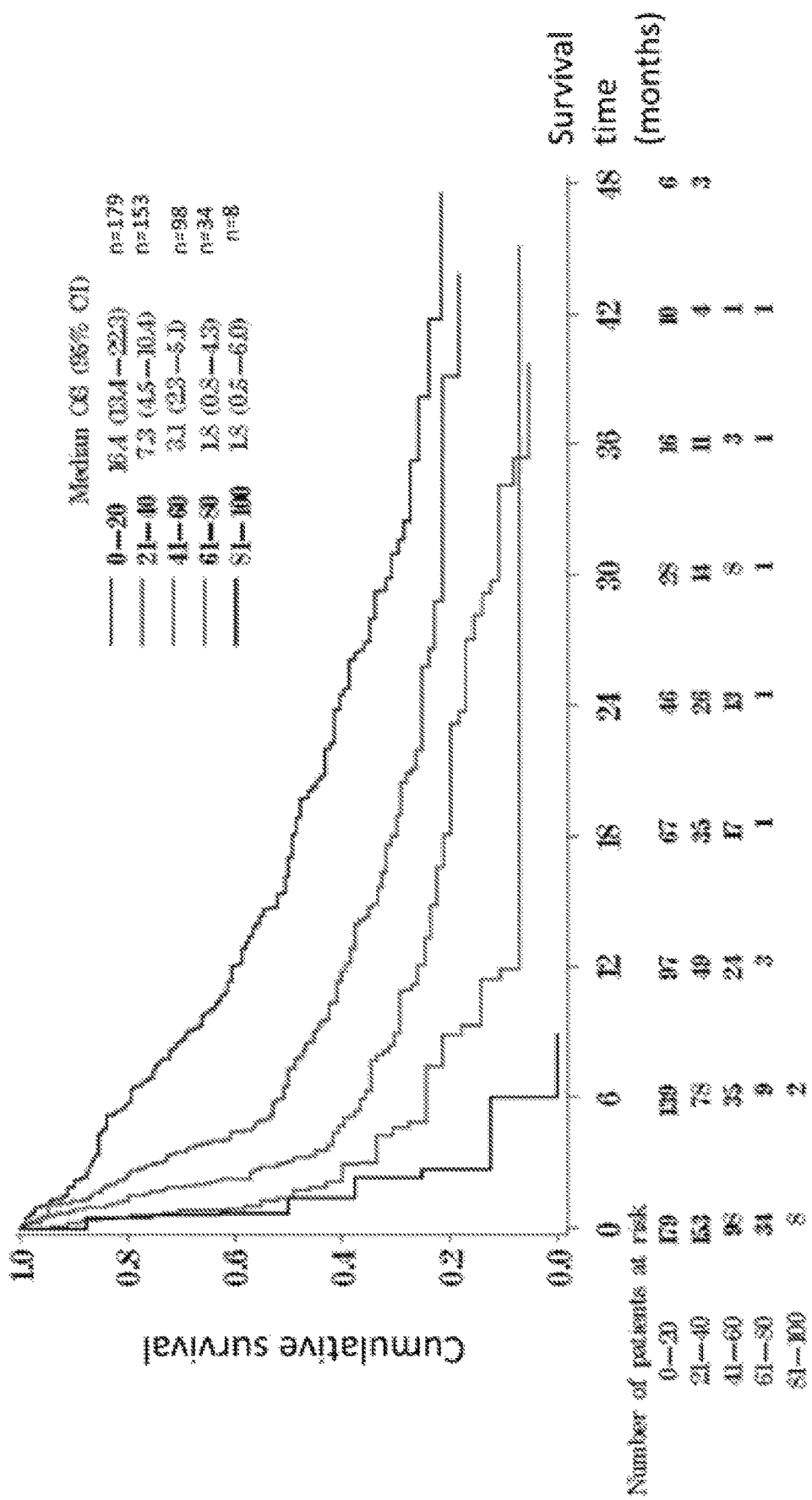
FIG. 6 illustrates overall survival curves according to stratified C30 index scores in patients with hepatocellular carcinoma in accordance with an embodiment. A lower C30 index score illustrates a better quality of life assessment value. C30 index score=Σ[(100-Physical functioning)+(100-Role functioning)+(100-Emotional functioning)+(100-Cognitive functioning)+(100-Social functioning)+(100-global QOL)+Fatigue+Nausea+Pain+Dyspnea+Insomnia+Appetite loss+Constipation+Diarrhea+Financial Difficulty]/15
Figure 7A:
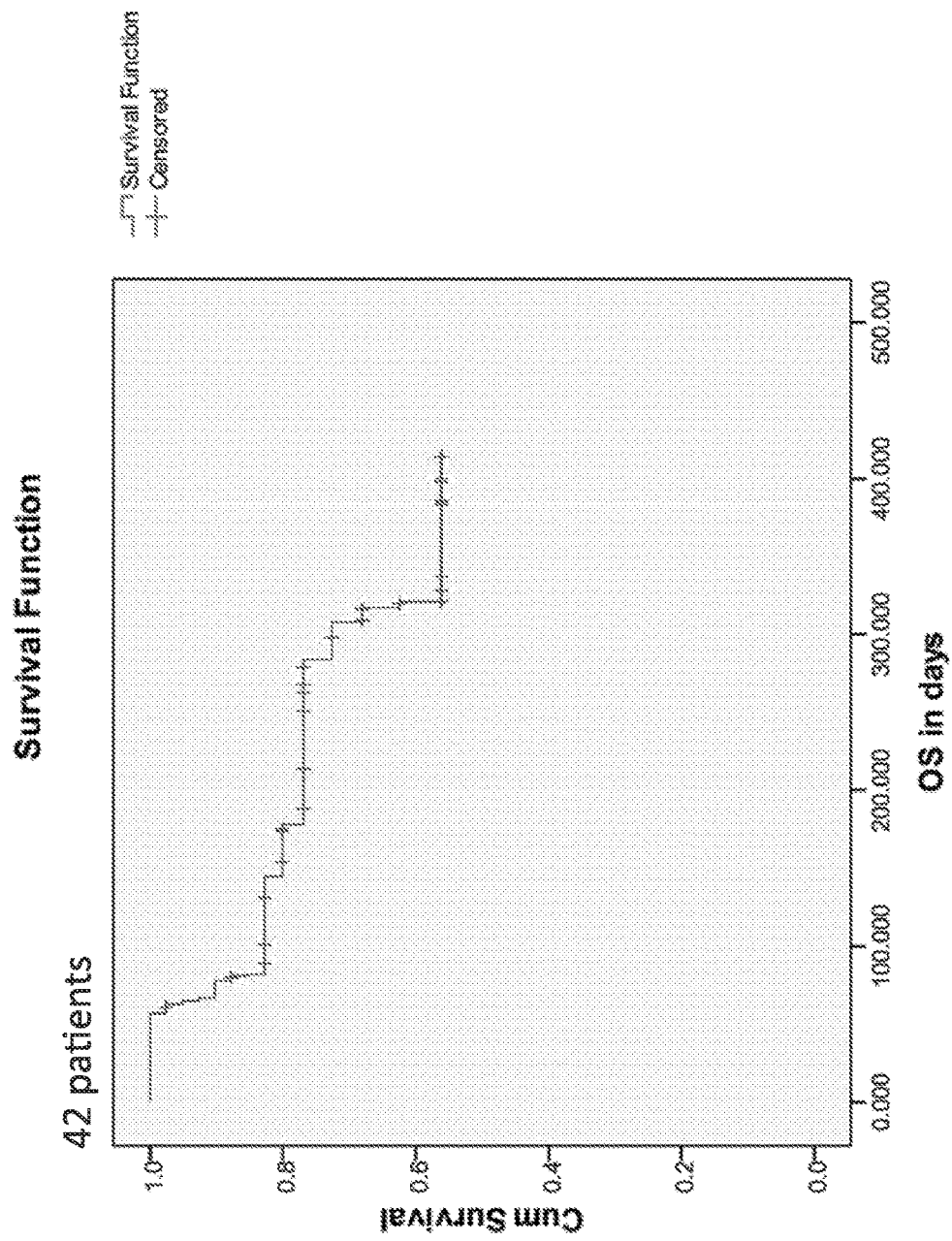
Figure 7C:
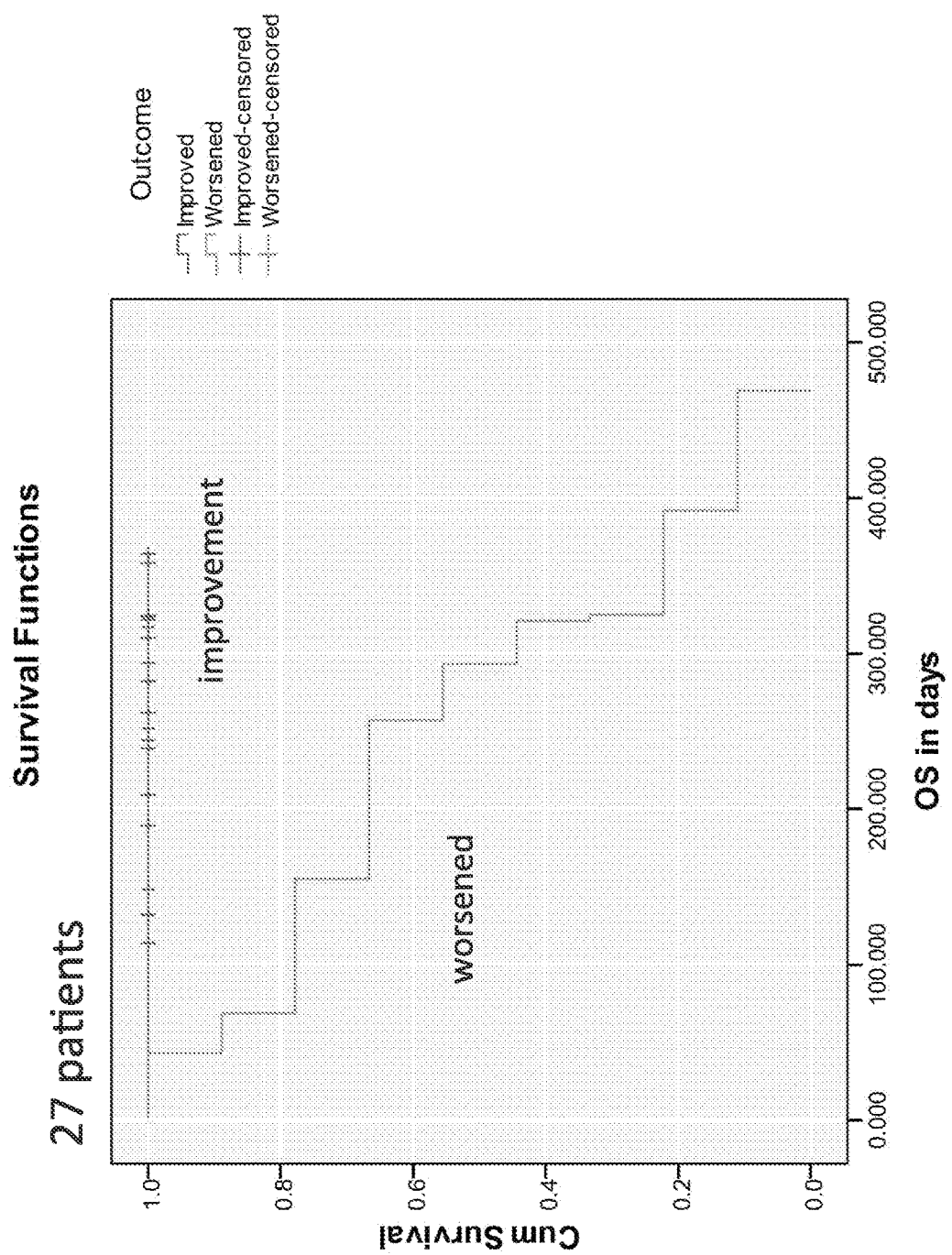
Figure 7D:
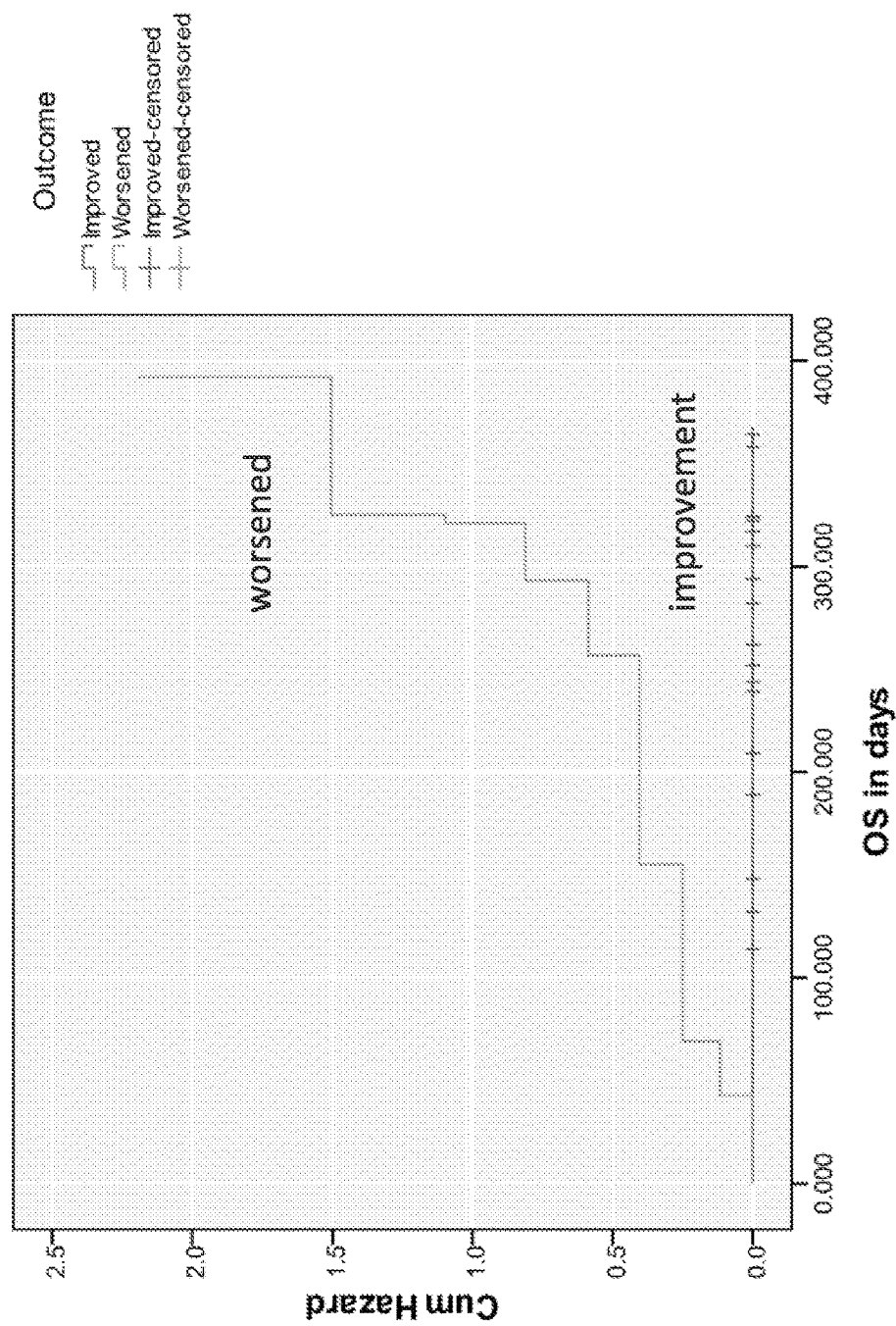
Figure 7E:
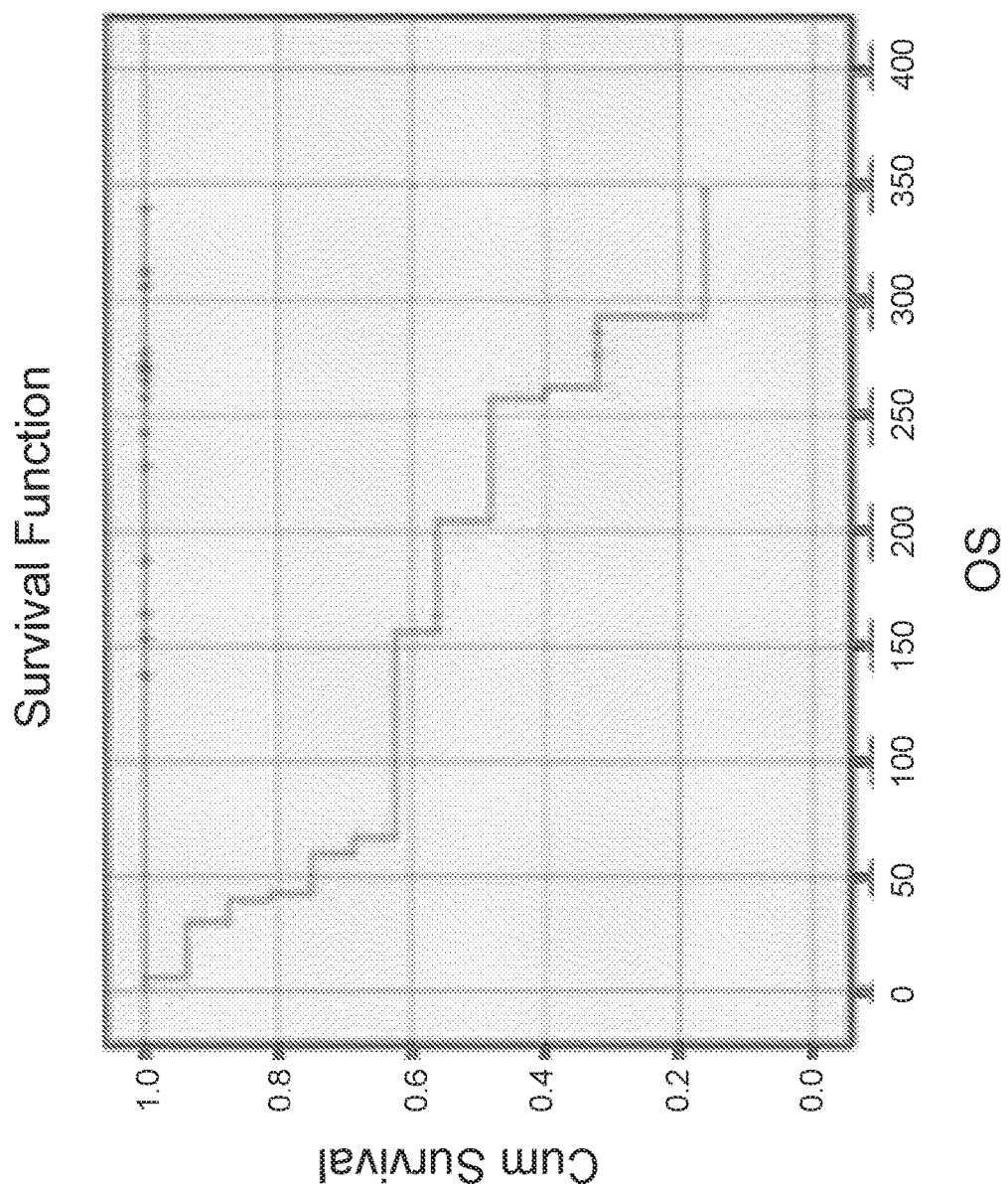

Quality of life prediction of survival may reflect patient own functioning and well-being better than crude performance status and toxicity measures measured by the physician; indicate lowering patient well-being earlier than other measures; and link with more positive behaviors, such as adherence to medical regimens and healthy lifestyles that affect survival reflect individual characteristics that affect the disease process. As shown in FIG. 6, quality of life analyses can be used in the pre-treatment (baseline) setting and during follow-up assessments with two distinguished objectives: baseline QoL refers to disease-specific characteristics and follow-up QoL refers to treatment-specific characteristics.

In the Validation Trial, patients with advanced HCC and healthy controls completed EORTC C30 v3.0 questionnaires (FIGS. 1A-C) prior to each exposure procedure with EMF. A total of 230 questionnaires were collected and QoL data were processed for analysis. From 6,900 QoL data points, only 7 missing data were reported. We developed an application for the iOS operating system for digital QoL assessment using EORTC C30 (QLQ-C30; Portuguese version 3.0). Digital QoL assessment data calculation was obtained based on EORTC recommendations.

Example 3

Correlation of QoL Parameters and Hemodynamic Stress Response Values

Figure 2:
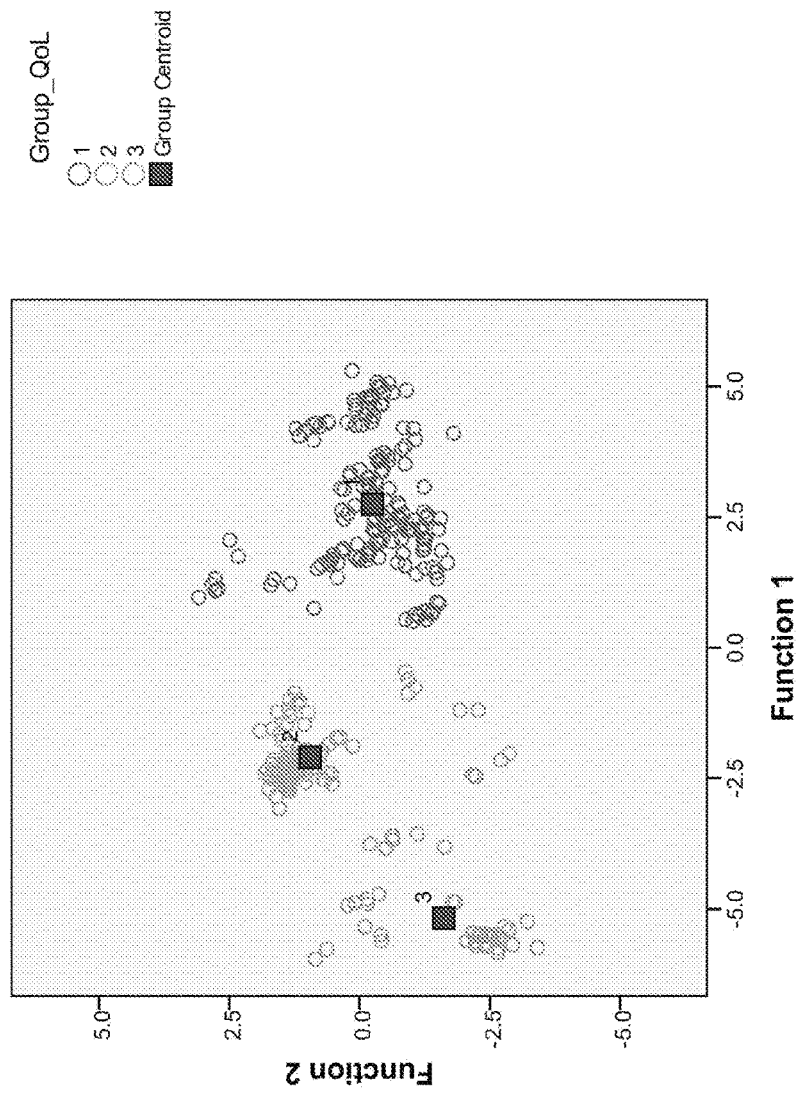
FIG. 2 depicts canonical discriminant functions from 38 advanced hepatocellular patients. Global health status values were grouped in terciles: A. QoL≥65%, B. 35%≤QoL<65%, C. QoL<35%.
Figure 3:
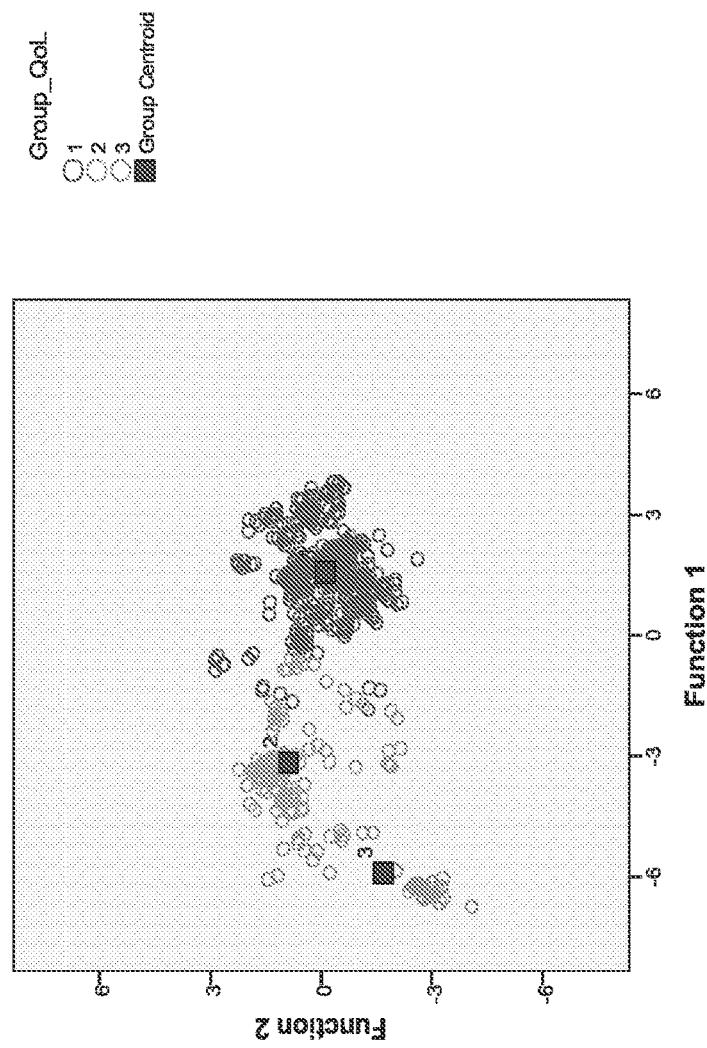
FIG. 3 illustrates canonical discriminant functions from 75 advanced hepatocellular carcinoma patients plus healthy controls. Global health status values were grouped in terciles: A. QoL≥65%, B. 35%≤QoL<65%, C. QoL<35%.

Digital data collected during AM EMF exposure procedures by the Hdp monitoring system were stored in a large database of digital hemodynamic stress response and digital QoL assessment information collected from patients with HCC and healthy controls. An initial correlation data analysis using QoL assessment parameters combined with autonomic hemodynamic stress response values from patients with HCC and healthy controls demonstrated a high correlation level with the same group of patients with HCC and healthy controls stratified in three groups of values according to their global health status (>95% correlation) (FIGS. 2-3).

Patients with advanced HCC stratified in these three distinct groups of patients based on QoL assessment in combination with autonomic hemodynamic stress response values showed significant difference in median overall survival (p=0.003) (FIG. 4) and significant different risk for hospital admissions respectively 14%, 40% and 45% to groups A, B and C (p<0.001, log Rank—Mantel Cox).

Example 4

Construction of the Prediction Model for Cancer Patients—Dimension Selection for Specific Predictions A number of variables from QoL assessment and hemodynamic stress response were studied alone and in combination for better discrimination results using factor analysis by principal components according to the desired prediction question. The relation between QoL and perceived levels of prognostic discrimination in patients with cancer is a dynamic process. For example, QoL assessments in patients with advanced cancer in early stages of cancer treatment reporting good performance status and being symptom free is a less discriminant variable among patients with similar reported conditions than QoL assessments in patients with advanced cancer in late stages of cancer treatment. In late stages, the patient's reported assessment is highly discriminant (alive with low tumor load vs end-of-life with high tumor load). In this latter scenario, QoL assessment is responsible for 72%-79% of the total variance explanation. On the other hand, QoL assessment is only responsible for 53% of the total variance explanation for patients in the early stage of cancer treatment. Initial QoL assessments have limited value in prediction models especially in patients with advanced cancer, because most of them have similar intermediate QoL values.

The hemodynamic stress response is responsible for close to 50% of the total variance explanation in the early assessment and drops to 21% in the late stages of cancer treatment. Considering that the hemodynamic stress response represents the allostatic load status of the individual, the combination of QoL assessment and autonomic hemodynamic stress response data values can be very useful for the construction of a prediction model especially in patients with advanced cancer.

Example 5

By selecting a small number of dimensions (<10) representing relevant QoL assessment values and autonomous hemodynamic stress response values collected by the Hdp monitoring system, statistical algorithms based on the kernel functions applied to the healthy control population were able to measure how distant a given patient is from the ideal healthy status, thereby creating a simple health scale solution for patient risk stratification. This outpatient, non-invasive and fast procedure provides a unique prediction solution for patients with a cancer diagnosis.

Patients with advanced HCC were stratified using the proposed prediction model into a low-risk patient population (24 patients) and a high-risk patient population (14 patients) with highly significant different outcomes (p<0.001) (FIGS. 7A-D). Surprisingly, the low-risk patient population seemed to have a significantly better outcome than previously expected, suggesting a potential treatment benefit associated with the exposure to AM EMF.

The low-risk patient population was associated with a low incidence of cancer related death (2.0%) and a low rate of hospital admissions (6.7%) in comparison with high-risk patient population that showed a high incidence of cancer related death (80.0%) and a high rate of hospital admissions (91.3%) during a 10-month median follow-up.

The prediction model stratification was based only on data collected at the first exposure procedure to AM EMF. Follow-up data collected after additional AM EMF exposure procedures by the Hdp monitoring system provided additional prediction information. Improvement in QoL assessment was reported in 61% of patients with advanced HCC after the second exposure procedure. Patients with improvement in QoL assessment had a significantly better overall survival (p=0.02) and significant reduction in hospital admissions (p=0.02) in comparison with the other 39% of the patients.

Figure 8:
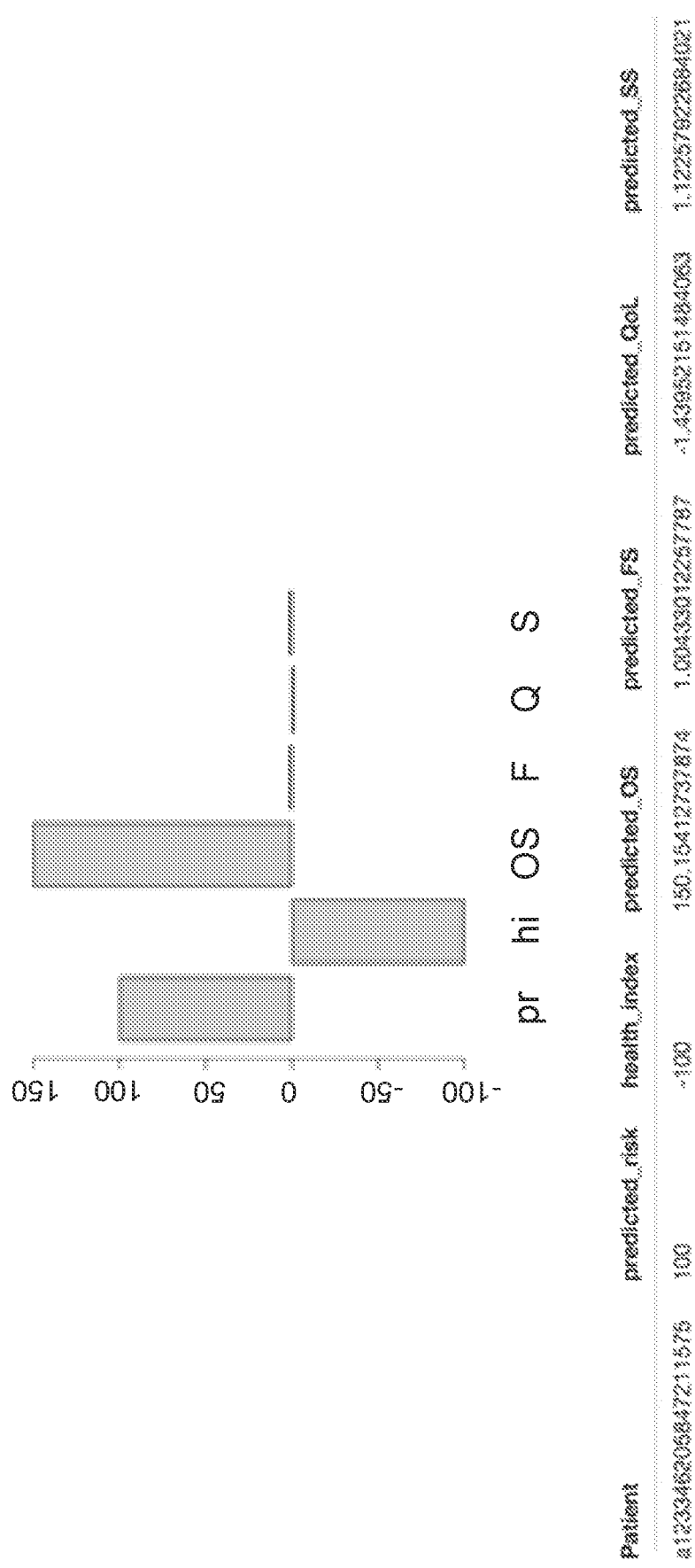
FIG. 8 depicts a prediction in accordance with an embodiment. The next exposure results were predicted according to a risk index, survival time measured in in days (OS), function status (FS), QoL and symptom scale (SS) in patients submitted to a second EMF exposure procedure. Predicted OS was reported in days; Predicted FS, QoL and SS were reported in percentage change (00%, −43%, +12%, respectively).

The comparison between the present and previous data collected from two sequential AM EMF exposure procedures by the Hdp monitoring system provided objective QoL assessment progress. Moreover, the statistical algorithms combined autonomic hemodynamic stress response values and the QoL assessment values from sequential exposures to feed the prediction model. This dynamic analysis forecasted quality of life, functional status and symptom scale progress for future exposure procedures in all patients with advanced HCC tested. The prediction model also forecasted changes in health risk status and the expected survival in days with high accuracy (FIG. 8).

The prediction model procedure between sequential exposures to EMF brought instant prediction information relevant to physicians and healthcare professionals. Those predictions may change practice, treatment choice, and chemotherapy dose, and may offer information for better hospital financial planning.

Figures 9A, 9B:
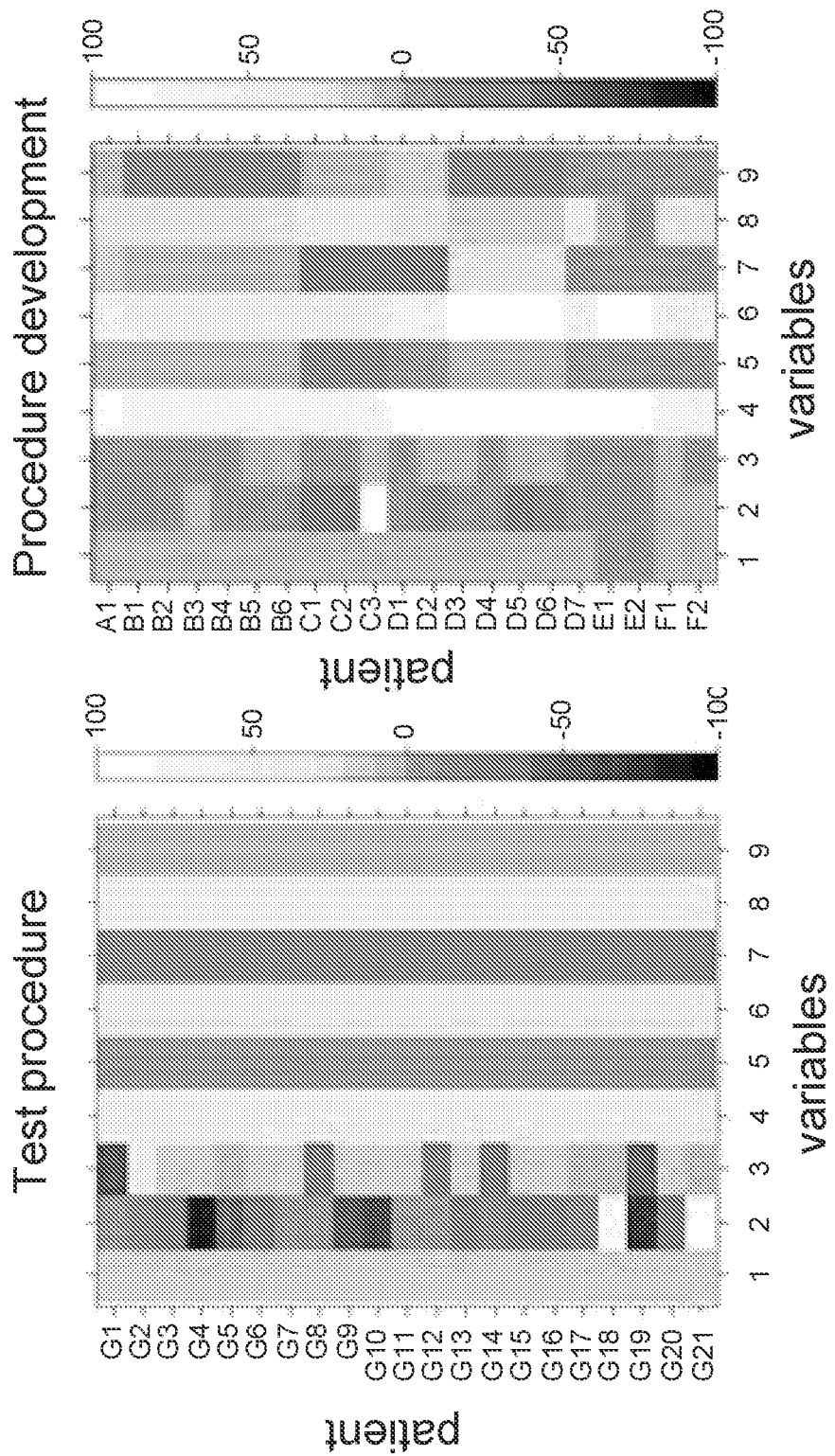
FIGS. 9A-B illustrate bar coding with prediction data in accordance with some embodiments.
Figure 9C:
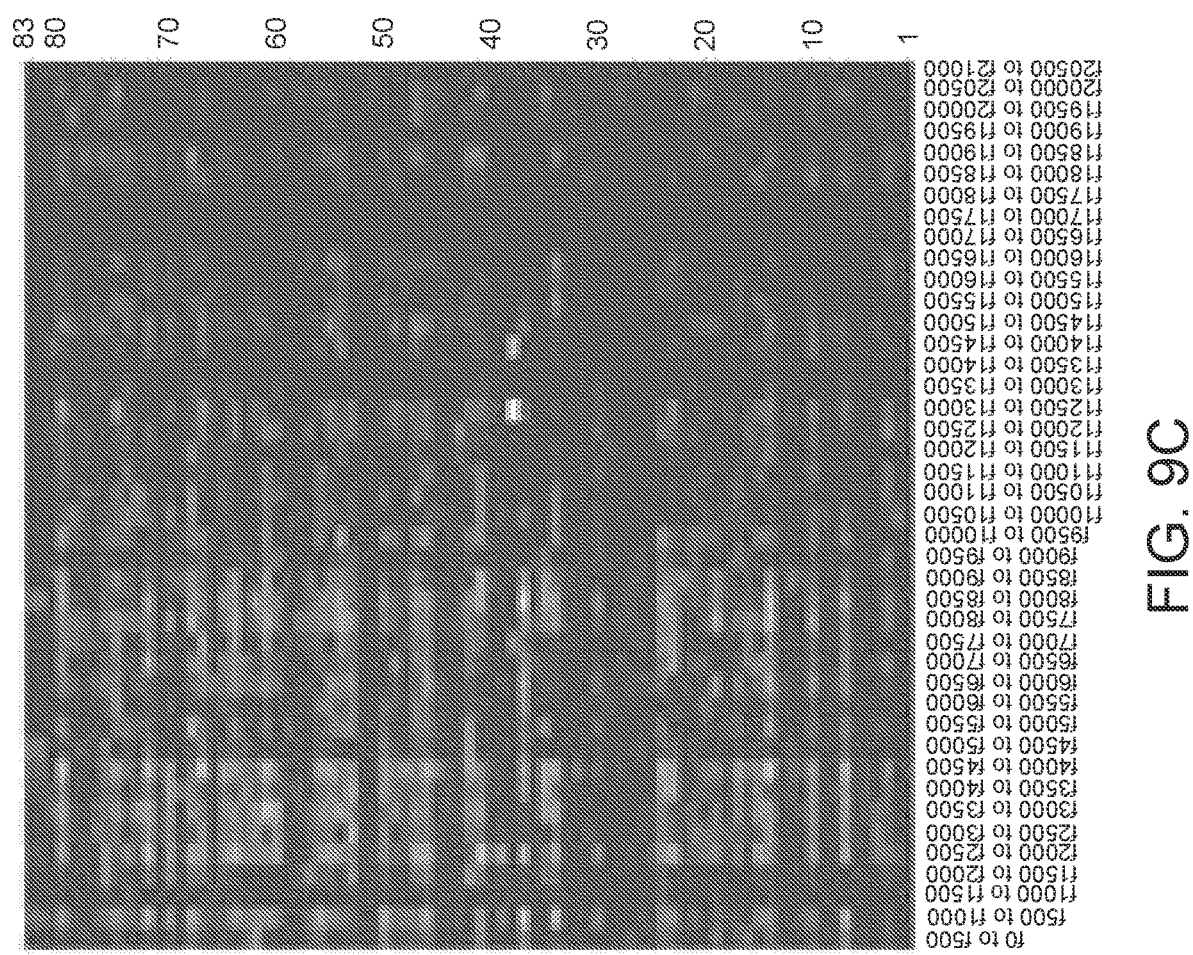
FIG. 9C illustrates an active frequency pattern in accordance with an embodiment.

Predictor variables and modulation frequency data (frequencies that induce an autonomic hemodynamic stress response) used in the prediction model were represented in a barcode solution. Those images allow computer processing for identification of similar patients in the database and may help the construction of frequency combinations associated with favorable treatment outcomes (FIGS. 9A-C).

The Hdp monitoring system collected high quality and instant digital data from individuals submitted to non-invasive AM EMF exposure procedure in the outpatient setting. QoL assessment and autonomic hemodynamic stress response values were processed by statistical algorithms at first and second exposure in order to provide instant prediction information to patients, physicians and healthcare professionals.

The prediction model is supported by a selected group of predictor variables that indicate the allostatic load status of an individual. This first reported approach and non-invasive methodology showed high accurate predictions in patients with advanced HCC. Besides instant information on prognosis and QoL assessment progress due to a treatment intervention, the prediction model may select patients that most likely benefit from the intervention (e.g., exposure to AM EMF).

Example 6

Figure 34A:
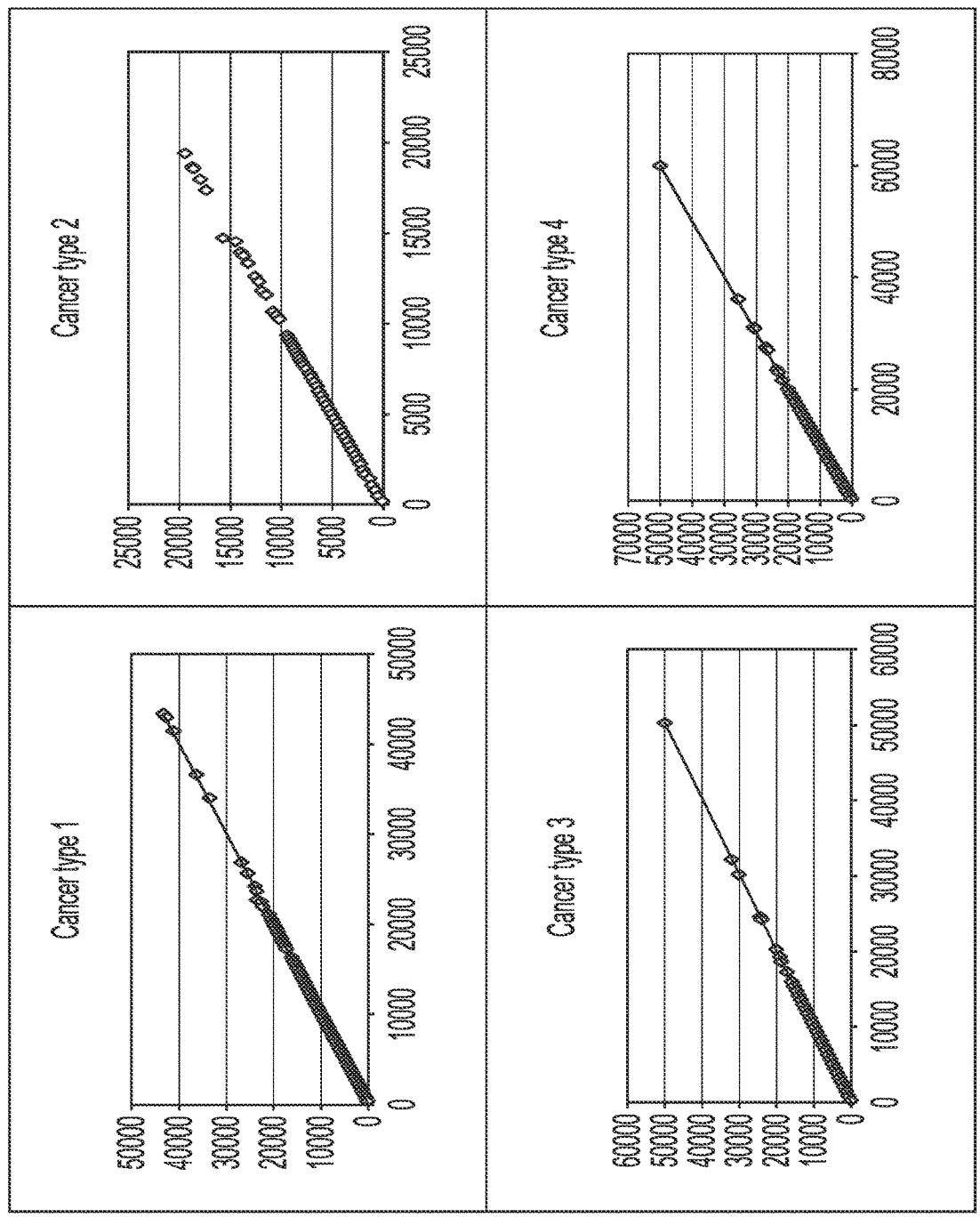
FIG. 34A illustrates the distribution of 1,054 cancer-specific frequencies from four cancer types in accordance with an embodiment.

FIG. 34A illustrates health condition-specific AM EMFs from 100 Hz to 40,000 Hz distributed in an apparent chaotic manner in different health conditions. By reorganizing different health condition-specific AM EMF using mathematical calculations described in the invention, we obtain a linear equation defined by $Hz=\alpha+\beta x$ with $R^2=99.9\%$. The statistical algorithms allow the construction of a series of AM EMF for the diagnosis and treatment of patients. The example showed the distribution of 1,054 cancer-specific frequencies from four cancer types.

Figure 34B:
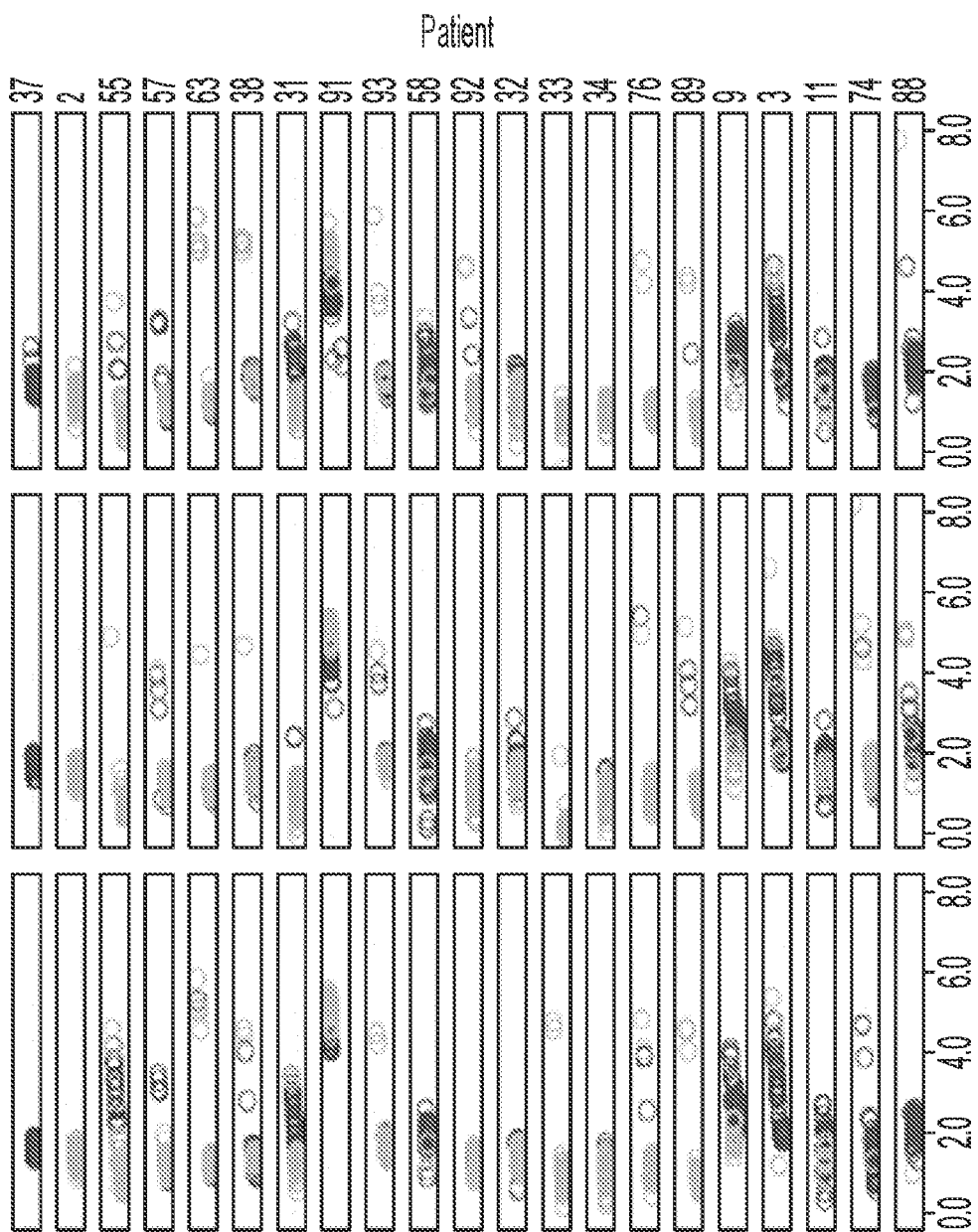
FIG. 34B illustrates the distribution of disease-specific AM EMF and healthy-specific AM EMF during exposure to three different groups of cancer-specific frequencies in 21 patients.

FIG. 34B illustrates that health condition-specific AM EMFs from about 100 Hz to about 40,000 Hz are distributed in a determined manner for different health conditions. The statistical algorithms allow the identification of patterns in a series of AM EMF used in the diagnosis of patients. The example showed the distribution of disease-specific AM EMF and healthy-specific AM EMF during the exposure to three different groups of cancer-specific frequencies in 21 patients.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

The embodiments of the present teachings described above are not intended to be exhaustive or to limit the teachings to the precise forms disclosed in the following detailed description. Rather, the embodiments are chosen and described so that others skilled in the art may appreciate and understand the principles and practices of the present teachings.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $1/10$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A system for prognosticating an outcome in a patient, the system comprising:
   an electrocardiogram monitoring system configured to detect an RR interval exhibited by the patient;
   a generator configured to generate a low-energy electromagnetic carrier output signal to which the patient can be exposed; and
   a processing system coupled to the electrocardiogram monitoring system and the generator, the processing system configured to:
   synchronize the electrocardiogram monitoring system and the generator, and receive, via the electrocardiogram monitoring system, a plurality of first RR interval values exhibited by the patient during a nonexposure period in which the patient is not exposed to the low-energy electromagnetic carrier output signal and a plurality of second RR interval values exhibited by the patient during or after an exposure period in which the patient is exposed to the low-energy electromagnetic carrier output signal, and determine the outcome associated with the patient based on a comparison of the plurality of first RR interval values and the plurality of second RR interval values.

2. The system of claim 1, wherein the outcome is selected from the group consisting of quality of life, survival, and hospital admission.

3. The system of claim 1, wherein the low-energy electromagnetic carrier output signal is configured to influence a cellular function of the patient.

4. The system of claim 1, further comprising an electrical sensor assembly coupled to the electrocardiogram monitoring system, the generator, and the processing system, wherein the electrical sensor assembly is configured to:

apply the low-energy electromagnetic carrier output signals to the patient; and receive an electrical response from the patient in response to the low-energy electromagnetic carrier output signals.

5. The system of claim 4, wherein the electrical sensor assembly is selected from the group consisting of an electrode belt configured to be worn by the patient and an antenna.

6. The system of claim 1, wherein the processing system is configured to execute a computational statistics model that has been trained to determine the outcome associated with the patient based on the comparison of the plurality of first RR interval values and the plurality of second RR interval values.

* * * * *